US012697512B2

(12) United States Patent
Pachoud et al.

(10) Patent No.: US 12,697,512 B2
(45) Date of Patent: Aug. 4, 2026

(54) Z-SHIELD™ FILTERED AIR PROTECTIVE SYSTEM

(71) Applicant: Zonit Structured Solutions, LLC, Boulder, CO (US)

(72) Inventors: William Pachoud, Boulder, CA (US); Steve Chapel, Iliff, CO (US)

( * ) Notice: Subject to any disclaimer, the term of this patent is extended or adjusted under 35 U.S.C. 154(b) by 968 days.

(21) Appl. No.: 17/222,867

(22) Filed: Apr. 5, 2021

(65) Prior Publication Data
US 2021/0322799 A1 Oct. 21, 2021

Related U.S. Application Data

(60) Provisional application No. 63/012,037, filed on Apr. 17, 2020, provisional application No. 63/005,343, filed on Apr. 5, 2020.

(51) Int. Cl.
*A62B 7/12* (2006.01)
*A61L 9/014* (2006.01)
(Continued)

(52) U.S. Cl.
CPC ............... *A62B 7/12* (2013.01); *A61L 9/014* (2013.01); *A61L 9/16* (2013.01); *A61M 16/105* (2013.01);
(Continued)

(58) Field of Classification Search
CPC .. A41D 13/1153; A41D 13/1184; A42B 3/12; A42B 3/28; A42B 3/285;
(Continued)

(56) References Cited

U.S. PATENT DOCUMENTS 2,688,962 A * 9/1954 Summers ............... A62B 18/04
128/201.15
3,181,532 A * 5/1965 Harris ................... A62B 18/04
2/416
(Continued)

FOREIGN PATENT DOCUMENTS

CN 201469929 5/2010
CN 201632173 11/2010
(Continued)

OTHER PUBLICATIONS

Communication pursuant to Rules 161(2) and 162 EPC, dated Nov. 15, 2022, issued in related EP Application No. 21783860.6.
(Continued)

*Primary Examiner* — Annette Dixon

(57) ABSTRACT

Personal protective equipment systems and methods of use are presented. In various embodiments, air enters the apparatus and passes through an optional pre-filter and through a one-way air "check" valve. The incoming air then enters a counter-flow heat exchange path and proceeds towards a heating chamber. The incoming air is heated to a desired temperature and exits via a return path. The air is cooled to a desired exit temperature suitable to be delivered to a user. The apparatus may be used in conjunction with a mask worn by a patient or an isolation chamber at least partially enclosing a patient, e.g., a patient room(s) or a tent erected over a patient gurney or bed.

31 Claims, 73 Drawing Sheets

(51) Int. Cl.

| | |
|---|---|
| *A61L 9/16* | (2006.01) |
| *A61M 16/10* | (2006.01) |
| *A62B 9/00* | (2006.01) |
| *A62B 18/00* | (2006.01) |
| *A62B 18/02* | (2006.01) |
| *A62B 18/08* | (2006.01) |
| *A62B 23/02* | (2006.01) |
| *B01D 46/00* | (2022.01) |
| *B01D 46/42* | (2006.01) |
| *B01D 46/58* | (2022.01) |
| *B03C 3/02* | (2006.01) |
| *B03C 3/34* | (2006.01) |
| *B63J 2/02* | (2006.01) |
| *F24F 7/003* | (2021.01) |

(52) U.S. Cl.
CPC ............. *A62B 9/00* (2013.01); *A62B 18/006* (2013.01); *A62B 18/02* (2013.01); *A62B 18/08* (2013.01); *A62B 23/02* (2013.01); *B01D 46/0032* (2013.01); *B01D 46/0043* (2013.01); *B01D 46/4245* (2013.01); *B01D 46/58* (2022.01); *B03C 3/025* (2013.01); *B03C 3/34* (2013.01); *B63J 2/02* (2013.01); *F24F 7/003* (2021.01); *A61L 2209/14* (2013.01); *A61L 2209/22* (2013.01); *B01D 2273/16* (2013.01); *B01D 2273/30* (2013.01); *B01D 2279/50* (2013.01); *B03C 2201/26* (2013.01)

(58) Field of Classification Search
CPC .......... A42B 3/286; A42B 3/288; A42B 3/32; A61B 90/40; A61F 9/068; A62B 17/005; A62B 17/04; A62B 18/00; A62B 18/003; A62B 18/006; A62B 18/04; A62B 18/045; A62B 18/082; A62B 23/02; A62B 29/00; A62B 9/003; B01D 25/24; B01D 25/26; B01D 35/06; B03C 5/00; B03C 5/024; F01M 1/10; F02B 1/04; F02B 3/06; F25B 21/02; F25B 2321/0212; F25B 2321/0251; G05D 23/1919; G05D 23/1931; Y10S 2/906
See application file for complete search history.

(56) References Cited

U.S. PATENT DOCUMENTS

| | | | | |
|---|---|---|---|---|
| 3,362,403 A | * | 1/1968 | Fleming ................. | A42B 3/288 128/201.24 |
| 3,529,594 A | * | 9/1970 | Charnley ............. | A62B 17/006 2/457 |
| 3,657,740 A | * | 4/1972 | Cialone .................. | A61F 9/068 128/205.25 |
| 3,736,927 A | * | 6/1973 | Misaqi ................ | A62B 18/006 128/201.25 |
| 3,822,698 A | * | 7/1974 | Guy ..................... | A62B 18/045 128/201.25 |
| 3,955,570 A | * | 5/1976 | Hutter, III ............. | A61B 90/40 128/863 |
| 4,185,329 A | * | 1/1980 | Sarazen .................. | A61F 9/061 2/428 |
| 4,280,491 A | * | 7/1981 | Berg ...................... | A42B 3/288 55/DIG. 35 |
| 4,620,917 A | * | 11/1986 | Nozawa ................... | B03C 5/00 210/748.01 |
| 4,648,394 A | * | 3/1987 | Wise .................... | A62B 18/082 351/154 |
| 4,676,236 A | * | 6/1987 | Piorkowski ............ | A62B 18/04 128/201.25 |
| 4,730,612 A | * | 3/1988 | Dampney ............. | A62B 18/045 128/201.24 |
| 5,009,225 A | * | 4/1991 | Vrabel ................. | A62B 18/006 128/202.19 |
| 5,125,402 A | * | 6/1992 | Greenough .......... | A62B 18/045 128/201.28 |
| 5,140,980 A | * | 8/1992 | Haughey ............... | A62B 17/04 D24/110.3 |
| 5,193,347 A | * | 3/1993 | Apisdorf ............ | G05D 23/1919 62/259.3 |
| 5,318,020 A | * | 6/1994 | Schegerin ............ | A62B 18/006 128/205.12 |
| 5,410,757 A | * | 5/1995 | Vienamo ................ | A62B 18/02 2/9 |
| 5,561,862 A | * | 10/1996 | Flores, Sr. ............ | A42B 3/286 2/422 |
| 5,575,278 A | * | 11/1996 | Bonhomme ........... | A62B 18/04 2/6.2 |
| 5,832,919 A | | 11/1998 | Kano | |
| 6,233,748 B1 | * | 5/2001 | Gieger ................... | A62B 29/00 128/205.27 |
| 6,497,753 B1 | | 12/2002 | Gutmann | |
| 8,973,173 B2 | * | 3/2015 | Elam ........................ | A42B 3/30 2/424 |
| 2005/0284470 A1 | | 12/2005 | Wei | |
| 2007/0102280 A1 | | 5/2007 | Hunter et al. | |
| 2007/0240716 A1 | * | 10/2007 | Marx ................... | A62B 18/006 128/204.21 |
| 2010/0305393 A1 | | 12/2010 | Akers et al. | |
| 2013/0071298 A1 | | 3/2013 | Tanimura et al. | |
| 2017/0312557 A1 | | 11/2017 | Schuller | |
| 2017/0361133 A1 | | 12/2017 | Yu | |
| 2018/0104517 A1 | | 4/2018 | Schuller | |

FOREIGN PATENT DOCUMENTS

| | | |
|---|---|---|
| CN | 103961822 A | 8/2014 |
| CN | 106512246 A | 3/2017 |
| CN | 208756733 | 4/2019 |
| WO | 9711750 A1 | 4/1997 |
| WO | 2020013907 | 1/2020 |

OTHER PUBLICATIONS

Issues with request for restoration, dated Dec. 5, 2022, issued in related NZ Application No. 794648.
Communication of European publication number and information on the application of Article 67(3) EPC, dated Jan. 18, 2023.
International Search Report and Written Opinion issued in International Application No. PCT/US2021/025818 mailed Jul. 27, 2021, 11 pp.
Extended European Search Report dated Apr. 3, 2024, EP Publication No. 4132661, 8 pages.

\* cited by examiner

GAITER

GAITER

FASTEST DESIGN TO MASS PRODUCTION
SIMPLIFIED PACKAGE

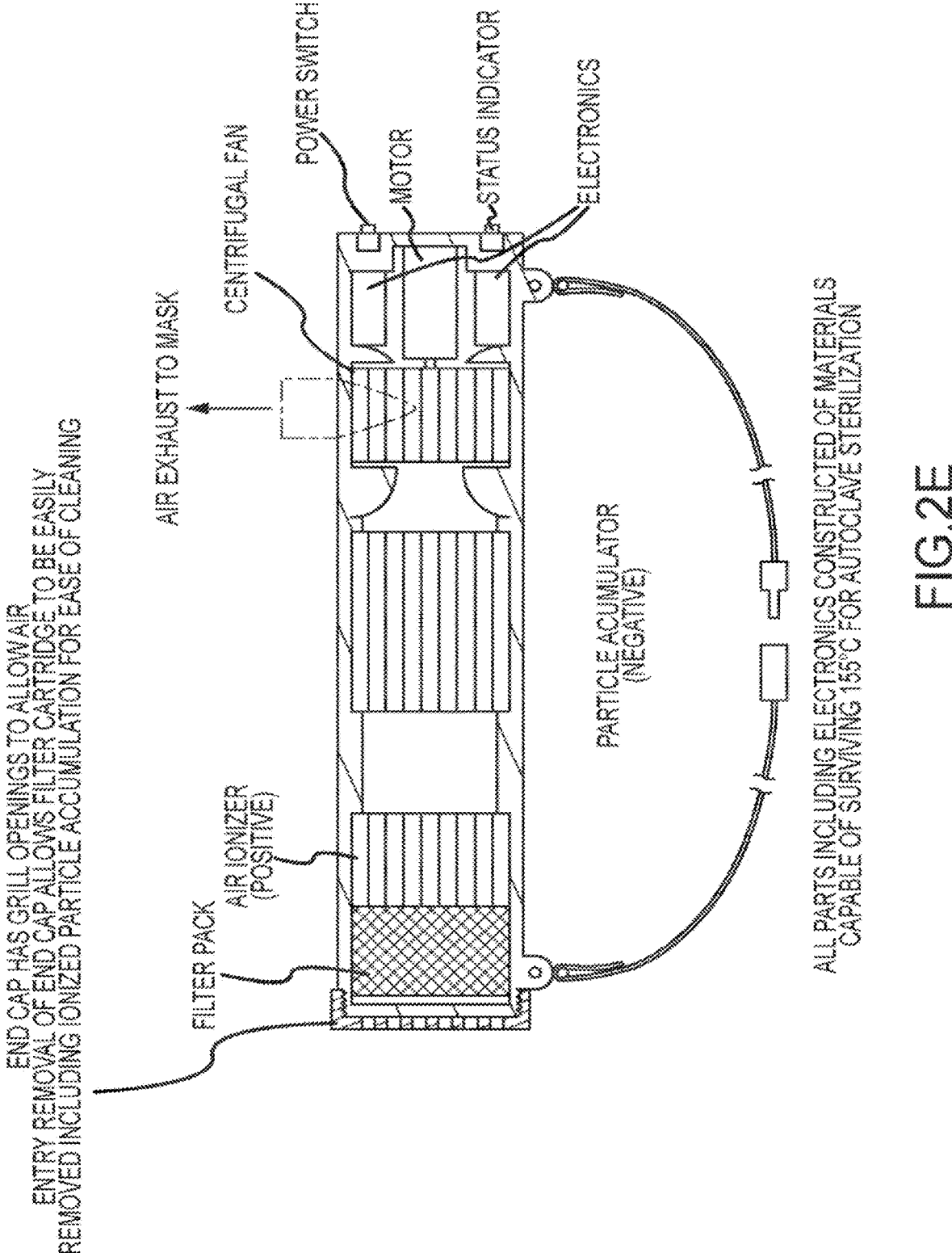

END CAP HAS GRILL OPENINGS TO ALLOW AIR
ENTRY REMOVAL OF END CAP ALLOWS FILTER CARTRIDGE TO BE EASILY
REMOVED INCLUDING IONIZED PARTICLE ACCUMULATION FOR EASE OF CLEANING

AIR EXHAUST TO MASK

POWER SWITCH

CENTRIFUGAL FAN

MOTOR

STATUS INDICATOR

ELECTRONICS

FILTER PACK

AIR IONIZER
(POSITIVE)

PARTICLE ACUMULATOR
(NEGATIVE)

ALL PARTS INCLUDING ELECTRONICS CONSTRUCTED OF MATERIALS
CAPABLE OF SURVIVING 155°C FOR AUTOCLAVE STERILIZATION

FIG.2E

"FANNY PACK"
FILTER ASSEMBLY

TO FACE MASK

SIMPLIFIED ELECTROSTATIC FILTER CARTRIDGE

POROUS CARBON BEADING FOAM

FOIL LAYER

AIR EXITS

CHARGED PARTICLES TRAPPED IN LATTICE

POWER SUPPLY

AIR IS IONIZED

AIR FLOWS THROUGH POROUS CARBON FOAM

REMOVABLE DISASSEMBLEABLE FILTER PACK

ELECTRONIC INVERTER POTTED INSIDE

OFF-THE-SHELF TISSUE PACK SIZE FILTER

PACK EASILY DROPS INTO FLOW CHAMBER

SURFACES CURVED FOR EASE OF DISINFECTING

TO FACE MASK

LIGHT WEIGHT AIR HOSE HIGH FLEXIBILITY

LOW VOLTAGE CENTRIFUGAL AIR FAN

AIR INLET SCREEN ON BOTTOM

DIRECT DELIVERY
TO STANDARD
POROUS FACE MASK

INTEGRAL AIR DIRECTOR DIRECTS
AIR FLOW ACROSS INSIDE SURFACE
OF CLEAR MASK TOWARDS NOSE
AND MOUTH, THEN DOWN AND AWAY

AIR DELIVERY FLIP
DOWN PROTECTION
MASK

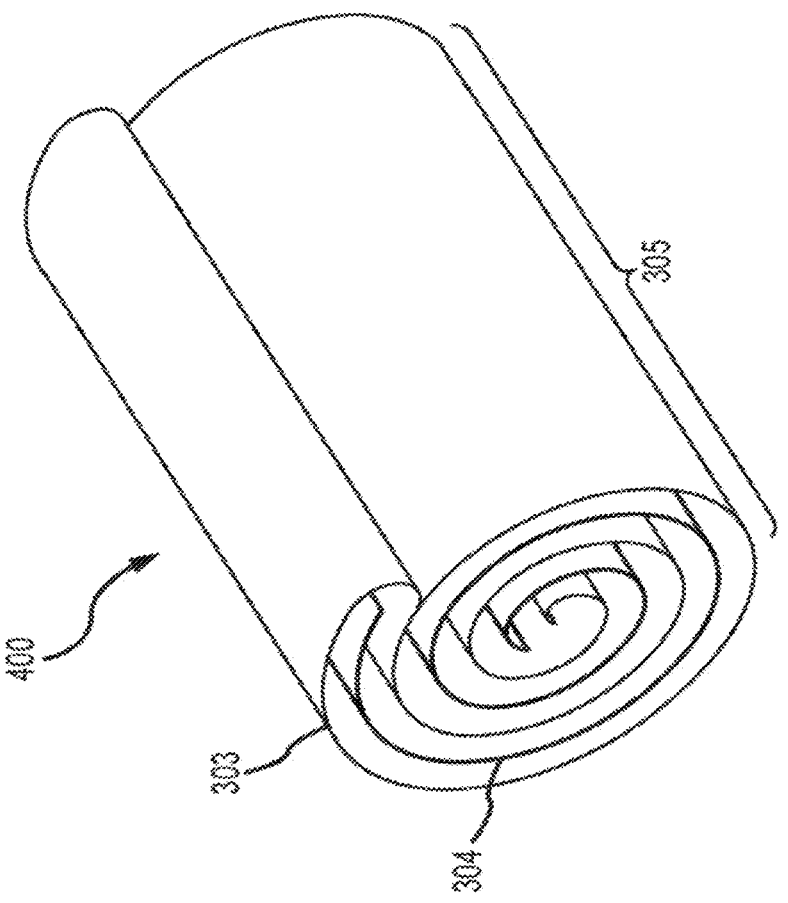
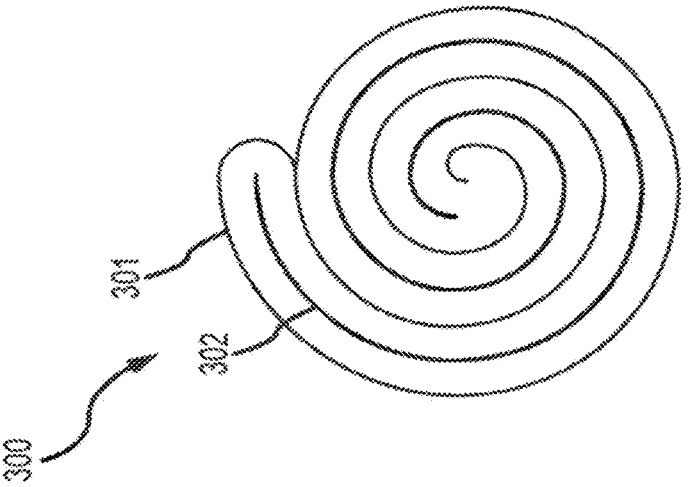
FIG. 5C

Collector plate unrolled
Stainless Steel

Total resistance of path ~.5 ohm

24 Amps @12 V = 288 W.
~1/2 second to 250 degrees C

VIRUS KILLED AIR
OUT TO MASK

200

21

22

23

VIRUS LADEN AIR
IN TO EXCHANGER

1200

1200

Z-SHIELD™ FILTERED AIR PROTECTIVE SYSTEM

CROSS-REFERENCES

This application is a non-provisional of U.S. Patent Application No. 63/005,343, entitled, "Z-SHIELD™ FILTERED AIR PROTECTIVE SYSTEM," filed Apr. 5, 2020 and U.S. Patent Application No. 63/012,037 filed Apr. 17, 2020, the contents of which are incorporated by reference herein as set forth in full and priority from this application is claimed to the full extent allowed by U.S. law.

FIELD

Embodiments of the present invention relate to the use of portable small form factor personal protective equipment in various contexts and providing innovative methods to allow them to be incorporated into the design of portable devices where space is limited the weight needs to be light and the wearer often needs to be able to move around and work in potentially contaminated indoor or outdoor air spaces. The invention also includes protective equipment for buildings and other spaces. For example, the contaminants can be either biologic (for example pathogens) or environmental in nature or both. Additionally, the invention needs to be able to very quickly be mass produced and take advantage of existing manufacturers and their products and thus be easily adaptable to many current manufacturing capabilities and processes. These types of issues arise in the design of products that are used in the medical, life safety and industrial fields, in particular, to devices used to protect health care workers and others against pathogens such as the pandemic COVID-19 virus.

We need a solution now. This can do the job needed.

BACKGROUND

The COVID-19 pandemic is reaching crisis proportions and a key fact that has emerged is that many health care workers have become infected, which greatly impacts the ability of health care systems worldwide to care for patients. We have learned that COVID-19 is not only spread via large droplet transmission but can survive in very small droplets for up to 2-3 hours. This means that rooms full of coughing COVID-19 patients will fill those spaces with a range of droplet sizes, some which will stay airborne, thereby enabling aerosol transmission. The current medical system has limited capability and equipment to protect health care workers against aerosol transmission. The equipment used for personnel working in full or partial isolation wards is expensive and hard to quickly manufacture. As a result, we can see that the protective equipment and protocols that are actually available and being used are inadequate to protect critically needed health care workers, resulting in their observed rates of COVID-19 infection, which have reached 30% in some Italian hospitals.

SUMMARY

The invention described herein can significantly reduce or solve the problem by providing methods and apparatus that can very quickly be mass produced and provide the needed protection. This is required immediately for the COVID-19 pandemic but also will be useful in a variety of applications and usage scenarios. Additionally, instantiations of the device can be built that are compatible with and can be used with existing masks used in the health care field, which may speed immediate adoption since the user can use already approved protection methods to conform to established guidelines and protocols then add a Zshield™ device for extremely effective protection. More generally, the invention can be used to purify air delivered to a user, purify air exhausted from a mask or isolation chamber, and/or to purify air delivered to or expelled from one or more chambers of a facility, e.g., as part of a ventilation system.

It can also be appreciated that the apparatus described in the various instantiations of the invention and other not described instantiations can be used in many other ways. For example, it can be used to protect patients from infecting other people around them both health care workers and patients. It can also be used in Heating Ventilating Air Conditioning (HVAC) systems in homes, buildings and other structures such as ships or planes to minimize the chances of contaminant particles affecting people in those environments.

In certain implementations, the present invention relates to providing methods to provide appropriately filtered safe or sterilized portable or stationary air supply to users in contaminated environments in various contexts, including in health care environments. This is a critically important issue worldwide as described earlier.

These objectives and others are addressed in accordance with the present invention by providing various systems, apparatus and processes that can be used to provide protection against airborne and other forms of contamination. Many aspects of the invention, as discussed below, are applicable in a variety of contexts. However, the invention has particular advantages in connection with health care applications. In this regard, the invention provides considerable flexibility in manufacturing devices that can be used to protect, patients, health care workers, and other people in hospital and other health care environments. It will be appreciated, however, that the invention can be used in other environments where purification of air is important, including residences, buildings, and ships.

The invention encompasses a number of aspects as generally set forth below. Each of these aspects encompasses inventive structure and functionality as will be understood from the description below.

In accordance with one aspect of the present invention, a personal protective equipment (PPE) system is provided. The system includes a facemask assembly extending over a nose and a mouth of a user to define a breathing space within an interior of the facemask assembly and a positive pressure air supply assembly. The positive pressure air supply assembly includes an air inlet, a conduit assembly extending between the air inlet and facemask assembly, and at least one air accelerator for forcing air through the conduit assembly from the air inlet to the facemask assembly. The system thus provides positive air pressure at the facemask assembly such that any communication of air between the interior of the facemask assembly and an exterior is substantially unidirectional. That is, the system inhibits or substantially prevents any leakage of contaminated air from the exterior into the interior of the facemask assembly. The system is useful for protecting users from exposure to contaminants that may be present in the air, including medical personnel and others.

In one embodiment, the facemask assembly includes fabric configured to extend over the nose and mouth of the user. The facemask assembly may further include a malleable member associated with at least one end of the fabric for conforming to a shape of a face of the user. For example, the malleable member may comprise a strip of malleable metal attached to or enveloped within the end of the fabric such that the facemask assembly can be formed (e.g., manually by the user) to match the shape of the user's face, e.g., the bridge of the user's nose. Alternatively or additionally, the facemask assembly may include a shield, formed from transparent, air impermeable material, configured to extend over a portion of the face of the user including eyes of the user. This shield may be mounted on headgear such as a headband or a cap (a hat, helmet, or other head covering). This shield may be movable between a first position, where the shield extends over the eyes of the user, and a second position where the shield is outside of a line of sight of the user. For example, this shield may pivot or flip between a deployed position where it covers the user's eyes and a stowed position where the shield extends outwardly from the user's face. The shield may be formed from flexible or rigid material and may be clear or tinted. In certain embodiments, the shield is formed from flexible material that may be readily shaped by attachment to contoured headgear or other structure of the facemask assembly. For example, this shield may be formed from 3D printable polycarbonate material.

The facemask's assembly may further include a gaiter for extending between one or more ends of the shield and a body of the user such that at least one of the shield and the gaiter extend over the nose and mouth of a user to define a breathing space within the interior of the facemask assembly. In certain embodiments, the gaiter is formed from flexible material such as fabric. For example, the gaiter may be formed from fabrics typically used for facemasks or from paper-based, cotton-based or other fabrics or materials. At least one end of the gaiter may be urged into close contact with the user's body by an elastic strap or other resilient member. The gaiter may be removably attachable to the facemask assembly, e.g., the shield or other structure of the facemask assembly, by Velcro, snaps, elastic bands or the like.

The positive pressure air supply assembly may be mounted on headgear, mounted on a body pack, or other structure. In any such case, the body pack may be interconnected to the facemask assembly by conduits, e.g., tubing formed from plastic or other material. The air supply assembly may include one or more filters for removing contaminants from the air. As used herein, "air" includes ambient air or other breathable gases. More than one filter may be provided. In this regard, multiple filters may be disposed in series in a single gas flow path or in parallel in separate air flow paths. Different filters may have different air filtering characteristics. A selector may be provided to select one or more filters. In certain embodiments, the one or more filters may include an electrostatic filter. The electrostatic filter may include an electrostatic element formed as a spiral of conductive material. The electrostatic filter may further include a filter medium formed from carbon impregnated mesh, steel wool or other material.

The PPE system may further utilize a power source. In this regard, the system may include a port for receiving power from an external source. Additionally or alternatively, the system may include mounting structure for receiving a portable power source such as a battery, e.g., a rechargeable battery or battery pack. The portable power source may be mounted on headgear, a body pack, or other structure.

The at least one air accelerator preferably provides a volumetric airflow sufficient to maintain positive pressure at the facemask assembly throughout a breathing cycle of a user. In this regard, the air accelerator may provide a volumetric flow rate of at least 85 L (3 cu. ft.) per minute and, more preferably, at least about 140 L (5 cu. ft.) per minute. For example, the air accelerator may comprise one or more fans. In certain embodiments, the air accelerator comprises a single fan having a diameter of no more than about 3 inches and, more preferably, no more than about 2 inches.

In accordance with another aspect of the present invention, a facemask system is provided. The facemask system comprises a shield and a gaiter. This shield is formed from transparent, air impermeable material, configured to extend over a portion of a face of a user including eyes of the user. The gaiter extends between one or more ends of the shield and a body of the user, wherein at least one of the shield and the gaiter extends over a nose and a mouth of the user to define a breathing space within an interior of the facemask assembly. The assembly further includes a connector for removably attaching the gaiter to the shield. The facemask system may be used with or without an air filtration system as described above.

In accordance with a still further aspect of the present invention, a filtered air apparatus is provided for use in connection with a PPE system. The system includes a facemask assembly extending over a nose and a mouth of the user to define a breathing space within an interior of the facemask assembly. The facemask assembly further includes an air inlet for providing air to the interior of the facemask assembly. The apparatus includes a filter for removing contaminants from air, a conduit assembly extending between the filter and the air inlet of the facemask assembly, and a fan for forcing air through the conduit assembly from the filter to the air inlet of the facemask assembly.

In accordance with another aspect of the present invention, an electrostatic filter is provided for use in connection with a PPE system. The PPE system includes a facemask assembly extending over a nose and a mouth of the user to define a breathing space within an interior of the facemask assembly and an air inlet. The electrostatic filter includes a cathode, an anode, and electrostatic filter element, formed from conductive material, configured as a spiral or parallel flat plates. The electrostatic filter is also comprised of an ionizer comprising fine wires, carbon impregnated mesh, steel wool or other material.

In accordance with a still further aspect of the present invention, a PPE system is provided. The PPE system comprises a facemask assembly and a filtered air supply assembly. The facemask assembly includes a shield, formed from transparent, air impermeable material configured to extend over a portion of a face of the user including the user's eyes, and air inlet for providing air to an interior of the facemask assembly, and a gaiter for extending between one or more ends of the shield and a body of the user, wherein at least one of the shield and the gaiter extend over the nose and mouth of the user to define a breathing space within the interior of the facemask assembly. The filtered air assembly includes a filter for removing and/or sterilizing contaminants from air, a conduit assembly, extending between the filter and air inlet of the facemask assembly, and optionally a fan for forcing air through the conduit assembly from the filter of the filtered air supply assembly to the air inlet of the facemask assembly.

Many of the aspects of the invention noted above have focused primarily on providing filtered or decontaminated air for inhalation by a particular user. However, the invention is applicable in other contexts. For example, the operation of these systems as described above can generally be reversed to decontaminate air including air exhaled by a user. This may be used in conjunction with a mask worn by a patient or an isolation chamber at least partially enclosing a patient, e.g., a patient room(s) or a tent erected over a patient gurney or bed (see, e.g., FIGS. 12A-12G showing a room filtration system, FIGS. 13A-13D showing gurney exhale filtration systems, FIGS. 14A-14I showing filter systems for tented areas, and FIGS. 15A-15B showing a portable room filter unit or R2D2 unit). Moreover, the present invention can be used in conjunction with ventilation systems to purify air delivered to or exhausted from one or more chambers of a facility such as a residence, building, hospital, or a ship such as a cruise ship, military ship, or other vessel.

Thus, in accordance with another aspect of the present invention, a protective equipment system is provided for decontaminating air exhausted from a facemask of a user such as a patient. In many cases, it is particularly useful to decontaminate air including air exhaled by a patient. If such exhausted air can be reliably decontaminated, that will reduce or substantially eliminate the need for others, such as healthcare providers in proximity to the patient, to wear personal protective equipment. It will be appreciated that this is particularly important in the case of an outbreak or pandemic where personal protective equipment may be scarce.

Accordingly, the inventive system includes a facemask assembly extending over a nose and mouth of a user and an air exhaust assembly. The air exhaust assembly includes an air exhaust, a conduit assembly extending between the air exhaust and the facemask assembly, and at least one air accelerator for forcing air through the conduit assembly from the facemask assembly to the air exhaust. A decontaminating assembly may be provided in fluid communication with the conduit assembly. For example, the decontaminating assembly may remove or neutralize viruses from the air exhausted from the facemask assembly. In certain implementations, the decontaminating assembly may include one of an electrostatic filter and a thermal treatment device.

In accordance with a still further aspect of the present invention, a decontaminating assembly may be provided in connection with an isolation chamber. The isolation chamber at least partially encloses a user. For example, the isolation chamber may include a room of a medical facility or a tent erected over a bed or gurney of a patient. The inventive system further comprises a decontamination assembly and a negative pressure air assembly. The decontamination assembly is operative to remove or neutralize viruses from air, e.g., to filter viruses from the air, kill the viruses, or otherwise render the viruses incapable of infecting available hosts. The decontamination assembly may include one of an electrostatic filter and a thermal treatment device. The negative pressure air assembly includes an air inlet in fluid communication with the isolation chamber, a conduit assembly extending between the air inlet and the decontamination assembly, and at least one air accelerator for forcing air through the conduit assembly from the air inlet to the decontamination assembly.

In accordance with another aspect of the present invention, a protective equipment system includes a facemask assembly and an air transport assembly. The facemask assembly extends over a nose and mouth of a user to define a breathing space within an interior of the facemask assembly. The air transport assembly includes an air port, a conduit assembly extending between the air port and the facemask assembly, and at least one air accelerator for forcing air through the conduit assembly between the air port and the facemask assembly. The air transport assembly may be used to deliver air to the facemask or exhaust air from the facemask.

In accordance with a still further aspect of the present invention, a protective equipment system is provided for use in connection with a ventilation assembly. The ventilation assembly provides ventilation for a facility and includes an air port, and air circulation element, and a conduit assembly for transporting air between the air port and one or more ventilated chambers. The decontamination assembly is in fluid communication with the conduit assembly and is operative for one of removing and neutralizing viruses from air. The decontamination assembly may include one of an electrostatic filter and a thermal treatment device.

In accordance with a still further aspect of the present invention, a protective system is provided. The system comprises a facemask assembly (or a hood) and a filtered air supply assembly. The hood can be increased in size to enclose whatever area is required, multiple patients, a tent, a room, etc. The facemask assembly includes a shield, formed from transparent, air impermeable material configured to extend over a portion of a face of the user including the user's eyes, and air inlet for providing air to an interior of the facemask assembly, air exhaust for taking the exhaled air and an optional gaiter for extending between one or more ends of the shield and a body of the user, wherein at least one of the shield and the gaiter extend over the nose and mouth of the user to define a breathing space within the interior of the facemask assembly. The filtered air assembly includes a one or more filters for removing and/or sterilizing contaminants from air, a conduit assembly, extending between the filter and the air exhaust of the facemask assembly (or hood), and one or more fans for drawing exhaled air through the air conduit assembly to the air inlet(s) of the filter assembly. The purpose of this instantiation is to protect health care workers and other people from an infected patient by filtering and/or sterilizing the air breathed and exhaled by the patient, so that it does not pose a threat. This instantiation has the advantage of isolating patients so that only health care workers who must come in close contact with them need their own PPS equipment. It can enable the use of much larger battery power sources, since patients are usually on beds or cots. Even when patients are moved they are usually on gurneys or wheelchairs that can support these heavy batteries, even when they are moved. Also, wall power can be used, were available, to run the devices and/or charge the larger batteries, since patients are mostly stationary in one location. We have all seen video footage of hospitals overflowing with COVID-19 patients, in every available space. This then requires that all hospital personnel be protected who must traverse common spaces, which lowers their efficiency and consumes valuable PPS resources that should be reserved for health care workers in close contact with infectious patients.

In accordance with a still further aspect of the present invention, a protective system is provided. The system comprises a heating/sterilization assembly which can also incorporate one or more filters of various types. The assembly could also be incorporated into traditional HVAC systems to add protection against a variety of contaminants. A sample instantiation of one such system is described below.

The invention disclosed can also be incorporated in a variety of apparatus, for example such as described in the following detailed description.

BRIEF DESCRIPTION OF THE DRAWINGS

The present disclosure is described in conjunction with the appended figures:

FIGS. 2A-2F show additional implementations of a filtered air system in accordance with the present invention;

FIGS. 3A-3L show embodiments of the filtered air system with the filter and air acceleration components deployed in a body pack in accordance with the invention;

FIGS. 5A-5F show alternative electrostatic filter implementations and the electrical configuration of a compact electrostatic filter in accordance with the invention;

Figure 1A:
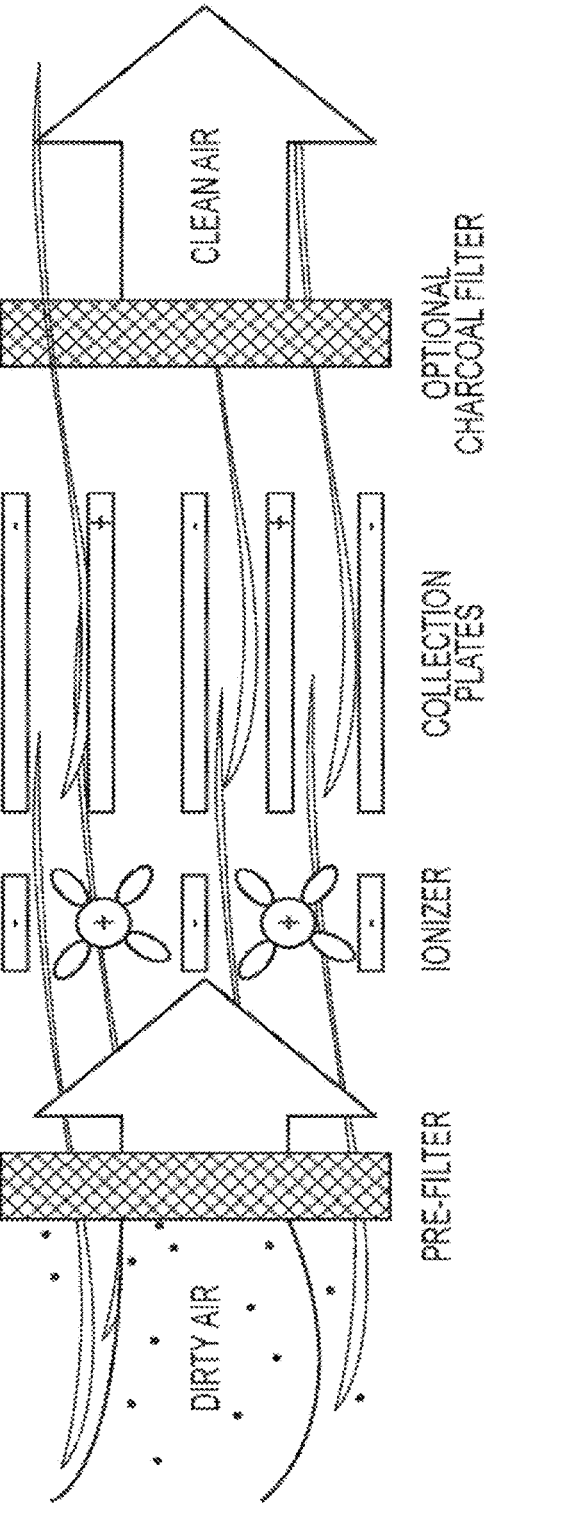
FIGS. 1A-1N show filter implementations and examples of a typical usage of several possible instantiations of the invention.
Figure 1B:
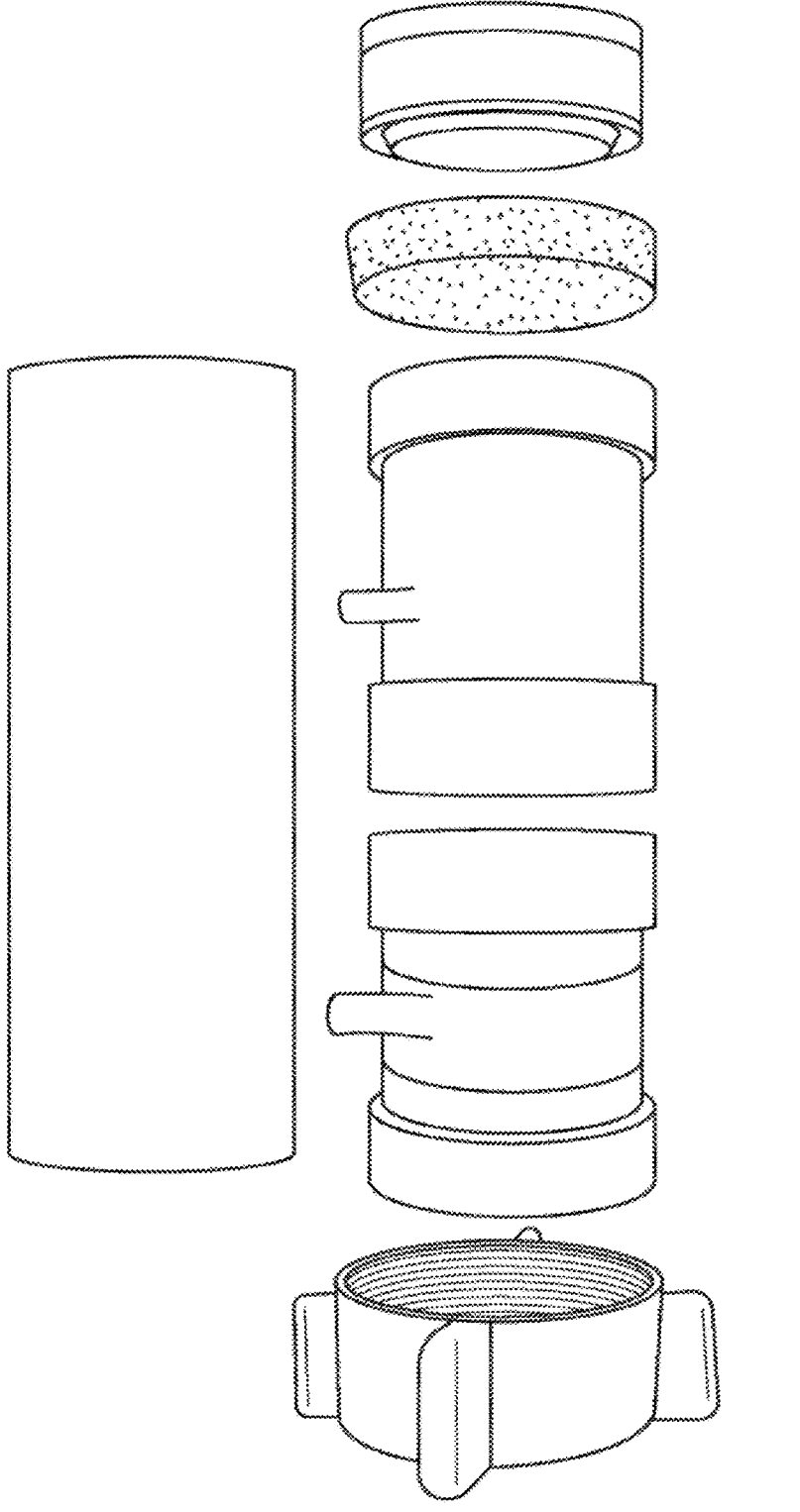

In the appended figures, similar components and/or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

DETAILED DESCRIPTION

The Zshield invention consists of the following functional modules (some possible instantiations can be seen in FIGS. 1A-6B).

I. Air Filtration Module ("Filtration Module")

The purpose of this module is to take one or more fans, one or more power sources, and one or more air filters to filter room or outside air and remove any desired contamination (for example pathogens and/or chemicals and/or smoke or other particles) and deliver the safe filtered air to the wearer so that they can breath it and are not exposed to unfiltered room or outside air. The fans and the filters can be replicated for increased reliability. Different and/or multiple filter types can be combined to provide filtering capable of removing any undesired kind of contamination from the input air. For example, a compact electrostatic filter (a novel design for such will be described later) can be combined with one or more traditional filter materials to achieve the desired result. Existing filter assemblies and cartridges can be used individually or in combination to help in quick mass-manufacturing of the module and lower costs. Each of the filter types used in the filtration module can be designed to be easily and quickly replaced or cleaned as needed. Low cost plastic adaptors can adapt a wide variety of manufacturer specific cartridge filters to the input port of the filtration module helping guarantee availability of the filter components. The fans used can be selected to provide the desired noise, efficiency, energy usage, pressure gradient, sealing or other characteristics needed in the application. The airflow device through the module can be shaped to provide the best characteristics such as minimal form-factor, weight, size, flow rate, flow characteristics, energy usage, sealing, noise control, or other characteristics as desired. An airflow and/or air pressure monitor and alert capability (for example visual and/or audible or other type of alert, such as sent to a cell phone via wired or wireless means) can be incorporated into the module to inform the user if there is a problem with the system, such as fan failure, filters becoming clogged or an inappropriate air leak.

The module can be implemented in a variety of ways, below are some possible examples:

a. Fan/filter/air outlet module ("filtration module") mounted on the back of a headband (which can be part of the face shield module described below), powered by an integrated or separate battery pack on a waistband or other convenient method of attachment to the body. Another possible power source for stationary users or users who are recharging the battery packs would be to use a cell phone charger or other suitable device as a power source for the module. Air from this apparatus is taken to the face shield via a flexible tube to an air input fitting on the face shield module or a face mask module. The air input can be located to allow the user to have the module on their front or back as is most convenient. Note that the face shield could integrate an air duct. In this instantiation, a high volume free-flow air supply fan can be utilized.

b. Fan/filter/air outlet module ("filtration module") mounted on the front or back of a waistband, powered by an integral or separate battery pack or other portable power supply mounted on the waistband or other convenient method of attachment to the body. Another option is to power the module via a suitable external power supply, such as a cell phone charger or other device, which can also act to charge an integrated or external battery pack. Filtered air is supplied via a flexible tube to a face shield module or a permeable mask. The air output of the filtration module and the air input of the face shield module can be located as needed and designed to rotate if desired to aid in locating the module on the body of the wearer as needed and optimizing routing of the air supply tubing to the face mask module. The flexible air tube can be attached to the wearers clothing via one or more suitable clips. Provision for the flexible air tube to be located as needed enables the wearer to apply outer clothing easily from either front closure or back closure variations.

The power source for the filtration module can either be or be designed to easily use many available off-the-shelf power sources, such as portable tool battery packs, rechargeable batteries, disposable batteries, cell phone chargers, etc., whatever is easily available. The battery pack can have adapters to incorporate one or more battery types as needed. The battery pack could be an existing power device that is compatible with the filtration module. The battery pack can adapt the output voltage to be what is needed and/or in a preferred instantiation the module can be designed to adapt the voltage and/or be designed to accept a range of input voltages. The connectors for the battery pack and module can similarly be designed to be used with commonly available connectors and cables. Simple secure connection methods, such as zip ties holding down power connection cables to tie-down loops on the devices can be used to insure that the battery pack does not accidentally become disconnected from the module. The battery pack can be equipped with visual and/or audible indicators and/or alerts to inform the user how much battery power is remaining and if it is nearing exhaustion. In addition, a variety of battery type adaptors can be supplied that simply adapt from an off-the-shelf battery of any voltage above 12 volts to the connection input of the filtration module. For example, the use of brand-name portable electric drill batteries could be used as well as auxiliary cell phone batteries, etc. The ability to utilize available resources is enabled by simply having a low-cost adapter.

The module in another instantiation can incorporate additional sterilization and/or medical capabilities, below are some possible examples:

a. One or more lights, (for example a Light Emitting Diode UV light) of one or more types (for example UV-C) can be integrated into the unit to sterilize the air drawn into the unit before filtering and or the filtered air before it is sent to the shield or mask modules. The sterilization can be done before, between two stages of or after filtering has been done. The light can be located within the unit such that it is not seen by or is dangerous to the user.

b. One or more chemical compounds in aerosol format can be injected into the air drawn into the unit. The injection can be done before, between two stages of, or after filtering has been done. The chemicals used may aid in or be integral to the removal of any contamination in the input air. The chemicals may work in conjunction with or activate one or more of the filters in the module. The chemicals may aid in preventing some or any effects of any contaminants from affecting or harming the user, regardless if the contaminants were reduced via filtration of the input air.

c. One or more medications in aerosol format can be injected into the air drawn into the unit. The injection can be done before, between two stages of or after filtering has been done. The medications may aid in preventing some or any effects of any contaminants from affecting or harming the user, regardless if the contaminants were reduced via filtration of the input air.

The module in yet another instantiation can incorporate additional sterilization and/or medical capabilities. We will now discuss an example of a thermal filter/sterilizer that can be used to sterilize viruses such as COVID-19 (and can sterilize or transform many other types of pathogens) and has other potential applications in accordance with the other described aspects of the invention. Virus molecules are comprised primarily of two components: 1) a nucleic acid genome and 2) a protein capsid that covers the genome. Together this is called the Nucleocapsid. A complete virus molecule is referred to as a Virion.

A protein capsid consists of several oligomeric structural subunits called Protomers. These Protomers are arranged in a specific pattern that essentially define the capsid. The intent of this invention is to expose the virion to sufficiently elevated temperature such that the Protomers Unfold, or simply fall apart. Hundreds of studies on a variety of virus examples demonstrate that virtually all examples experience unrecoverable molecular decomposition at temperatures above 100 degrees C. Most experience degradation or permanent damage at temperatures at or around 75 degrees C.

The intent of this aspect of the invention is to provide a means to efficiently expose an air volume necessary for safe human breathing to an assured thermal elevation necessary to guarantee all or substantially all target contaminant molecules (for example a virus) present in that air are permanently and irreversibly damaged such that the target contaminant is inactivated, killed or otherwise rendered harmless or changed such that it could conveniently be removed from the airstream via an appropriate filter type, for example a MERV, HEPA, activated charcoal or other appropriate filter type. This method of sterilization also works for many other pathogens, such as bacteria and some chemical components, which can be broken down by sufficient heat such that they are safe to breath or can then be safely filtered out via an appropriate filter type.

Generally speaking, a virus is most likely to be transmitted from one location to another in a liquid water container, or droplet. These droplets can exist in various sizes from visible down to only a few Microns in diameter. In larger particles the amount of latent heat in the water prevents the carried virus from immediate exposure to high temperature, temperatures needed to unfold the Protomer, or preferentially permanently alter the molecular arrangement. Thus, exposure to the necessary temperature must be maintained long enough for heat to be conducted through the water to the virus. An additional filter that insures that the size of any water droplets that pass through it are minimized, can be used upstream of the thermal neutralizer to increase the efficiency and effectiveness of the thermal pathogen neutralizer. There are many types of filters that will do this well, for example a very fine screen or an N95 material filter or other appropriate filter material.

Temperatures in excess of 100 degrees C. will essentially vaporize the surrounding water from the virus. However, the time necessary to evaporate that water will be dependent on how long it is exposed to the elevated temperature, and the associated turbulence of the surrounding air. As the water evaporates, it also absorbs some heat from the surrounding air, requiring that localized (with respect to the surface of the target water droplet) air must be replaced with heated air. Turbulence of the air is optimal for this. As the temperature of the air around the water is increased, the time necessary to boil off the water is shortened. When dealing with water droplet sizes in the 10 micron to 100+ microns, the exposure time necessary to evaporate the water away from the target virus becomes very short. Exposure time of less than 10 milliseconds will guaranteed total evaporation of water droplets of 200 microns or less in turbulent air when exposed to a minimum of 150 degrees C.

This invention is intended to expose certain potential contaminants, for example, virus or bacteria in water droplets, as well as unshielded virus or bacteria to the necessary temperature and for the necessary time to inactivate the contaminants or kill them. This system is also applicable to a wide variety of other potential containments including much larger bacteriological organisms.

Upon exposing the desired volume of air to the required temperatures necessary to inactivate the pathogen, that volume of air must be returned to a temperature suitable for human inhalation. That volume of air must also be isolated 100% from any other source of air to guarantee safe delivery to the user of pathogen free air.

Figure 9:
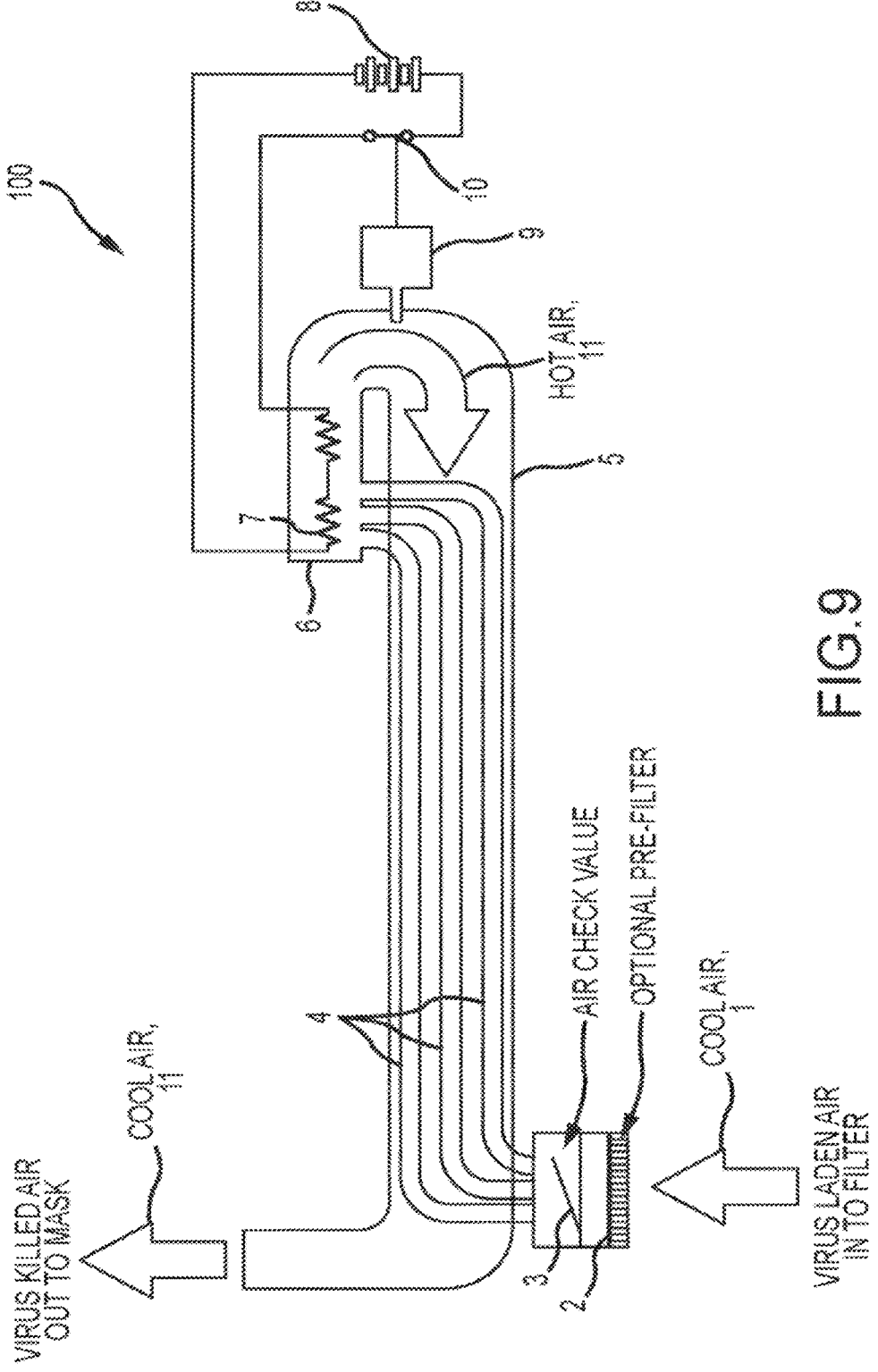
FIGS. 9-11B show thermal decontamination systems in accordance with the present invention.

The basic elements of this instantiation of the invention are shown in FIG. 9. Air 1 to the apparatus 100 enters and passes through an optional pre-filter 2 and through an one-way air "check" valve 3. This air is presumed to be at about ambient, or about 20 degrees C. The incoming air then enters the counter-flow heat exchange path 41 and proceeds towards the heating chamber 6. The counter-flow heat exchange path 41 can be tubes, flat plates, or any other suitable heat transfer material such as aluminum, copper or other suitable thermally conductive material. As the air proceeds from the input of the exchange path towards the heating chamber 6, it picks up heat that is above the input air temperature that is returning from the heating chamber 6 via the return heat exchange path 5. The air returning 11 from the heating chamber 6 is directly in contact with the opposing surface of the counter-flow heat exchange path 41, and thus transfers heat from the returning heated air to the incoming delivery air. This exchange of heat is occurring in the heat exchanger for the purpose of conserving energy, making the device more efficient and requiring less power. It is desirable to reduce the amount of heat added to the incoming air via heating elements 7. Recovering the heat accomplishes this.

As air enters the heating chamber 6, it immediately encounters heating elements 7. An electrical current through the heating elements 7 causes them to rise in temperature. The incoming air cools these heating elements, while at the same time increasing its temperature. Thermostat 9 senses the temperature of the air in the heating chamber 6 and disconnects the power source (battery) 8 via the switch 10 when the air temperature exceeds the desired temperature. It can be assumed that the thermostat can be adjusted or selected for any desired temperature that is greater than the ambient temperature. In the case of this invention, the initial target temperature is 400 degrees Fahrenheit, or about 200 degrees C. Due to the fact that little is known about the exact temperature needed for what amount of time to inactivate many specific contaminants, this temperature will most likely need to be adjustable. Also, the other applications described herein, may require different output air temperatures. This can be accomplished by various instantiations of the invention.

Upon encountering the heating chamber 6, the incoming air, which has been pre-heated by the exiting air, is heated to the desired temperature and exits via the return heat exchange path 5. Upon completing the path through the exit path for the air, the air is now cooled to the desired exit temperature, for example within a few degrees (preferably within 10 and, more preferably, within 5 degrees F.) of the incoming air, and is at a temperature suitable to exit 11 and be delivered to a user. This air may not have the virus removed from it, but the virus will be rendered harmless at this point. Additional filters both upstream and/or downstream of the thermal neutralizer assembly can be utilized as needed for the desired applications.

Figure 10:
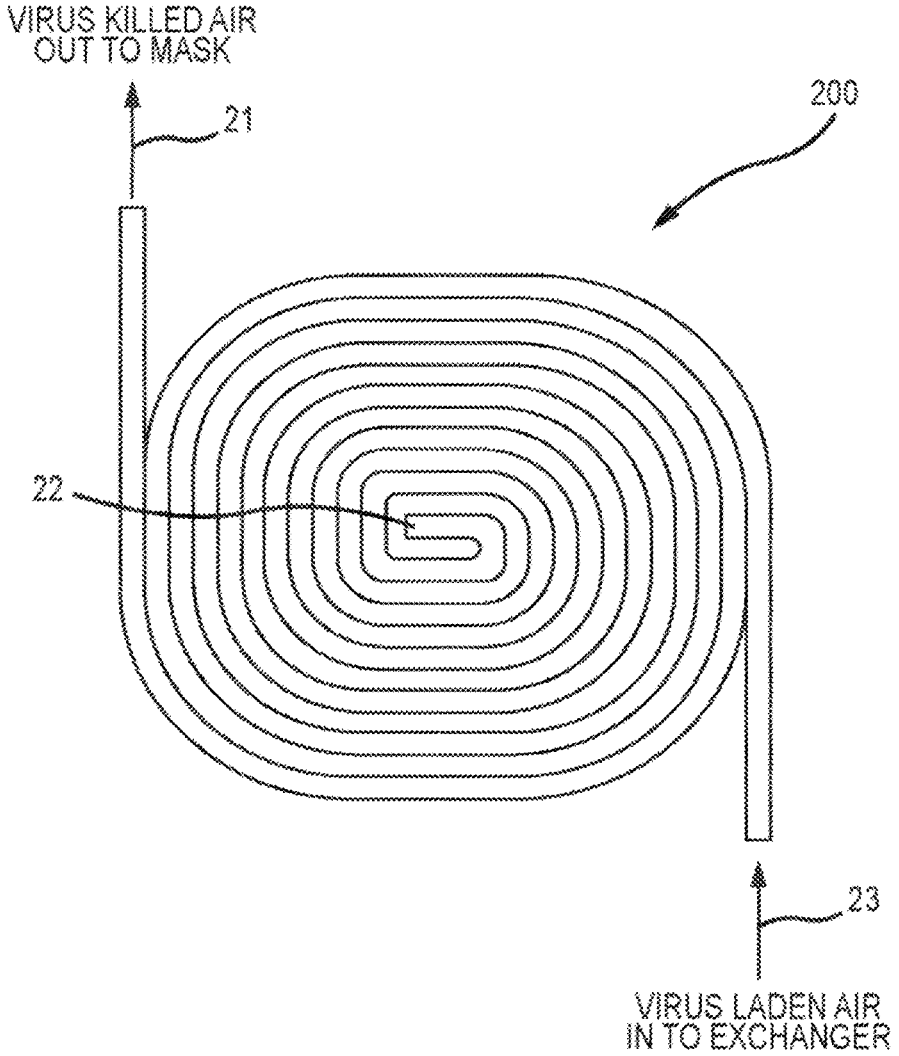

The heat exchanger example shown is a compact linear counter-flow design. The design is utilized because it is one of the most efficient of the simple to mass produce methods of air-to-air heat exchange. Other means of air-to-air heat exchange can be utilized if other features are desired. For example, FIG. 10 shows a similar heat exchanger 200, the liner counter-flow mentioned in FIG. 9, but in this case the air delivery path consists of a spiral shape set of plates or tubes. This configuration reduces the overall size of the heat exchanger. It also places the heating chamber 22 in the center of the assembly where lost heat is retained in the air path for the most part. Only the top and bottom of the heat exchanger must be insulated to minimize heat loss and insure that the filter assembly remains sufficiently cool to be worn on the body of a user. The use of this design makes the finished product more compact and improves portability. An additional gain is made because the air is constantly turning and therefore has more turbulence. This tends to improve the efficiency of heat transfer.

This design has the detrimental aspect of having greater resistance to flow, and thus places more burden on the lungs of the person drawing breath through this filter. To overcome this resistance, the size of the air path can be expanded accordingly, or supplemental air movement means may be provided such as a fan, or bellows. Many combinations of fans, or natural respiration, sizes and shapes of the heat exchanger are possible depending on the specific application and desired characteristics One preferred instantiation of this invention is a spiral configuration as shown in FIG. 10, without auxiliary air moving components. The design is preferred because of optimizing efficiency, ease of manufacture, and compact form-factor and lower power requirements.

Figure 11A:
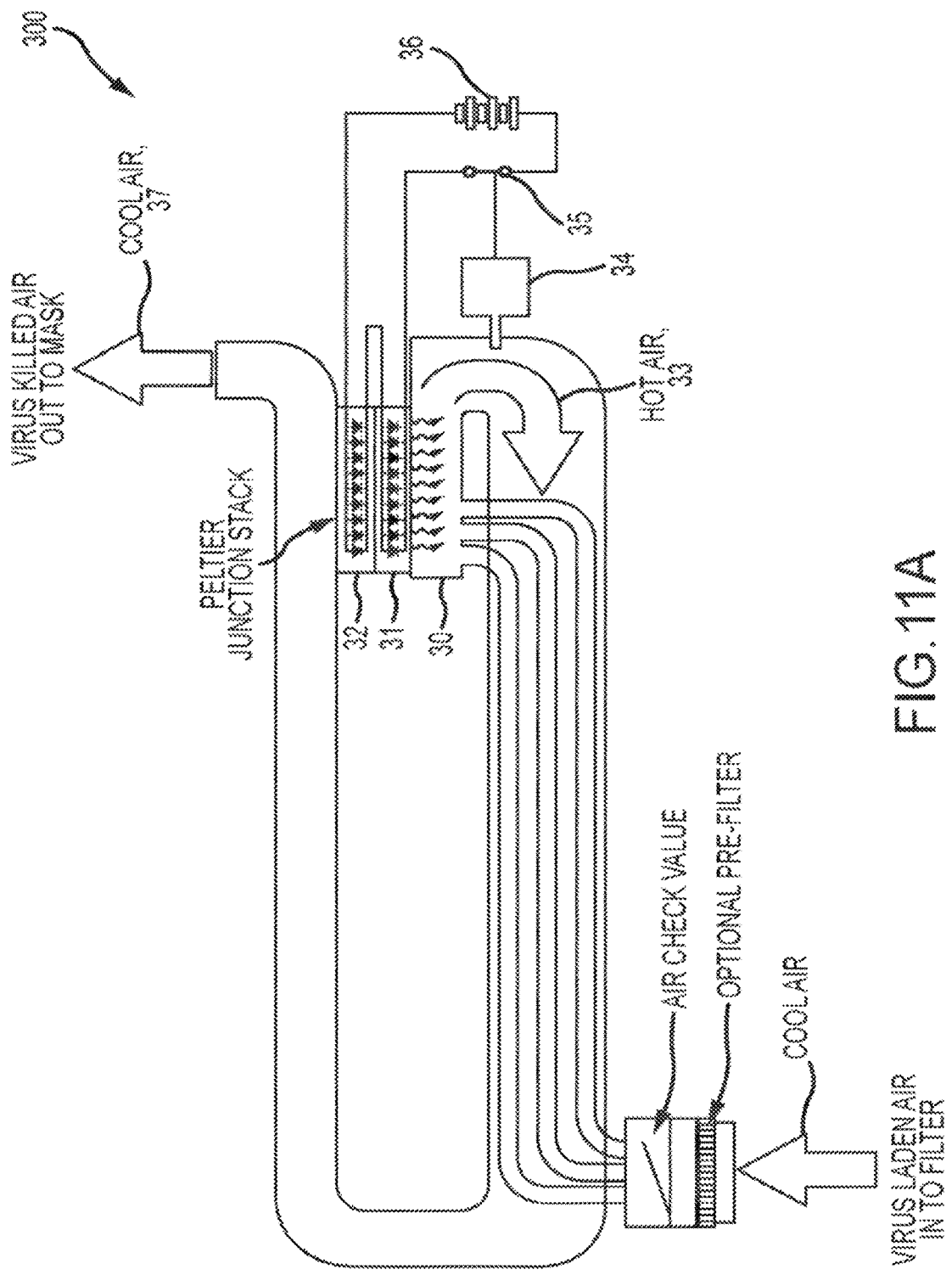
Figure 11B:
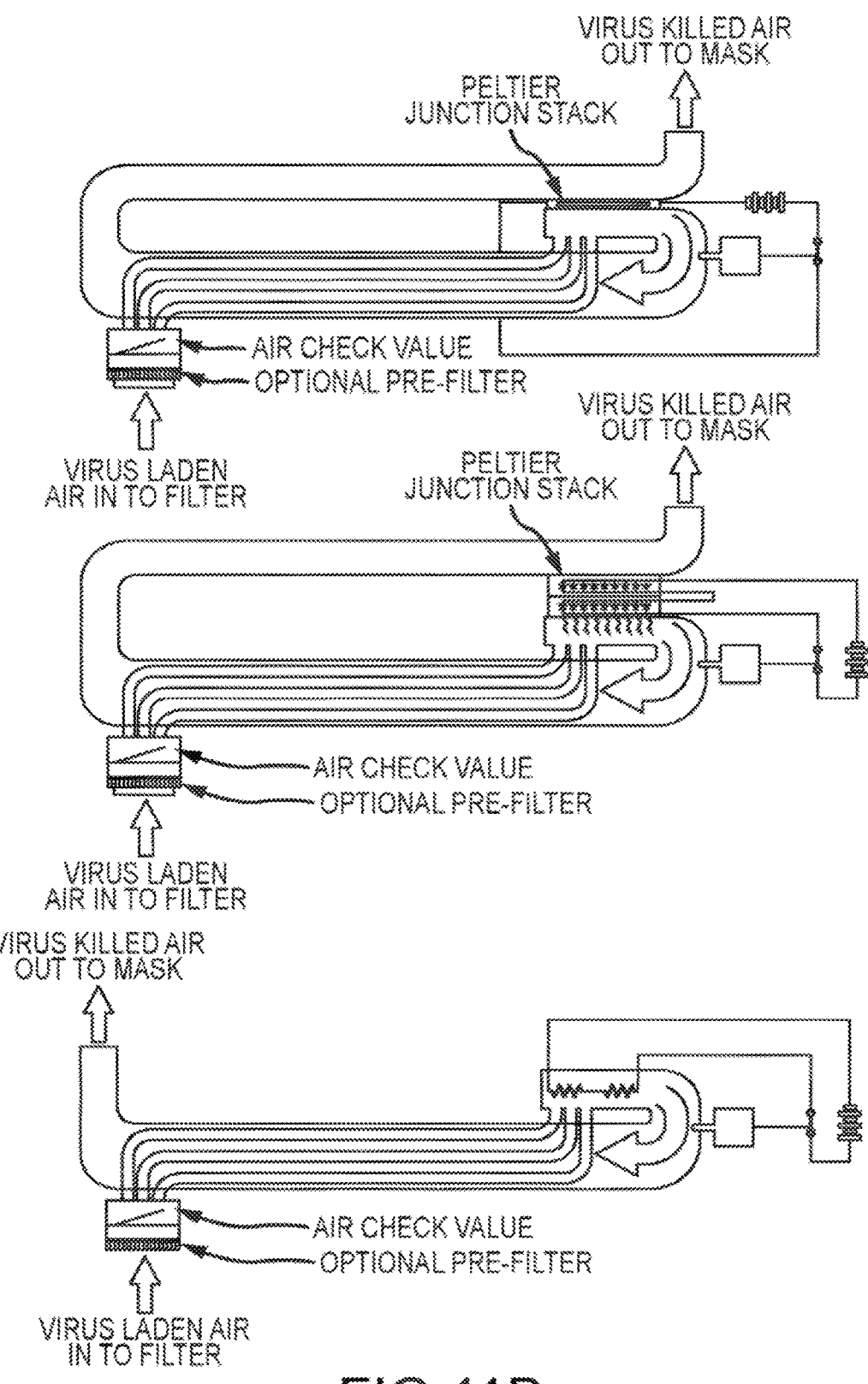

FIGS. 11A-11B show a similar schematic diagram as described in FIG. 9 with a modification to the heating chamber 30. Instead of resistive heating, the hot side of a Peltier Junction Thermoelectric Module 31 is placed so as to be thermally joined to the heating chamber 30 to heat it directly. The Peltier effect is the phenomenon that when an electrical potential difference applied across a thermocouple device, a temperature difference is generated between the junctions of the different materials in the thermocouple. The power used to heat the chamber is also moving heat from the exit air to the heating chamber simultaneously when utilizing a Peltier junction device as the heat source instead of pure resistance. The exit air is cooled even further than it had been in the heat exchanger by the incoming air. The desire is make the air delivered to the person to be as close to the optimum temperature for breathing and user comfort as possible or in other applications meet the required exit air temperature Utilizing the Peltier Module allows for an efficient way to heat the air as needed, but in the process, also improve the comfort of the user. The average humidity of the air passed through the filter module will remain approximately the same as the input air humidity, again making it comfortable to breath in most usage cases.

FIGS. 11A-11B also show a second Peltier Module 32 stacked on top of the primary Peltier Module 31. This secondary Peltier Module allows for increasing the total range of thermal temperature difference between the heated side and the cooled side. In this case, it is desirable to heat the heating chamber 30 to between 200-230 degrees C. The incoming air is likely to be about 20 degrees C. This "stacking" of Peltier arrays is not a new concept. It has been utilized for attaining higher temperature differentials in many applications. However, in the context of this invention an additional feature is observed. Because the Peltier Module connected to the heating chamber 30 has its hot side at or about 200 degrees C., then the module is specific to high temperature applications. It's "Cold side" is operating in the 100 degree C. range when the device is at its maximum efficiency. Thus, adding a different style Peltier Module that has a much better efficiency at only 40 degrees C. differential allows the total 200 or 210 degrees C. to be attained at relatively efficient levels. In the case of all Peltier devices, only about 5 to 7 percent of the input power can be attributed to actual cooling. In other words, when 100 Watts of power is used in the device, only about 5 to 7 Watts can be moved from the cold side to the hot side, or visa-versa. When effectively transferred between the Heating chamber 30 and the exhaust air 37 this 5 percent is a direct 5% improvement in the overall efficiency. Thus, the design criteria for the heat exchanger can be expanded via the greater efficiency attained. For example, its overall size could be reduced, which is important in some applications.

The filter/sterilization assembly described in this invention can be used in lieu of or in combination with the other types of filters already earlier.

Figure 15A:
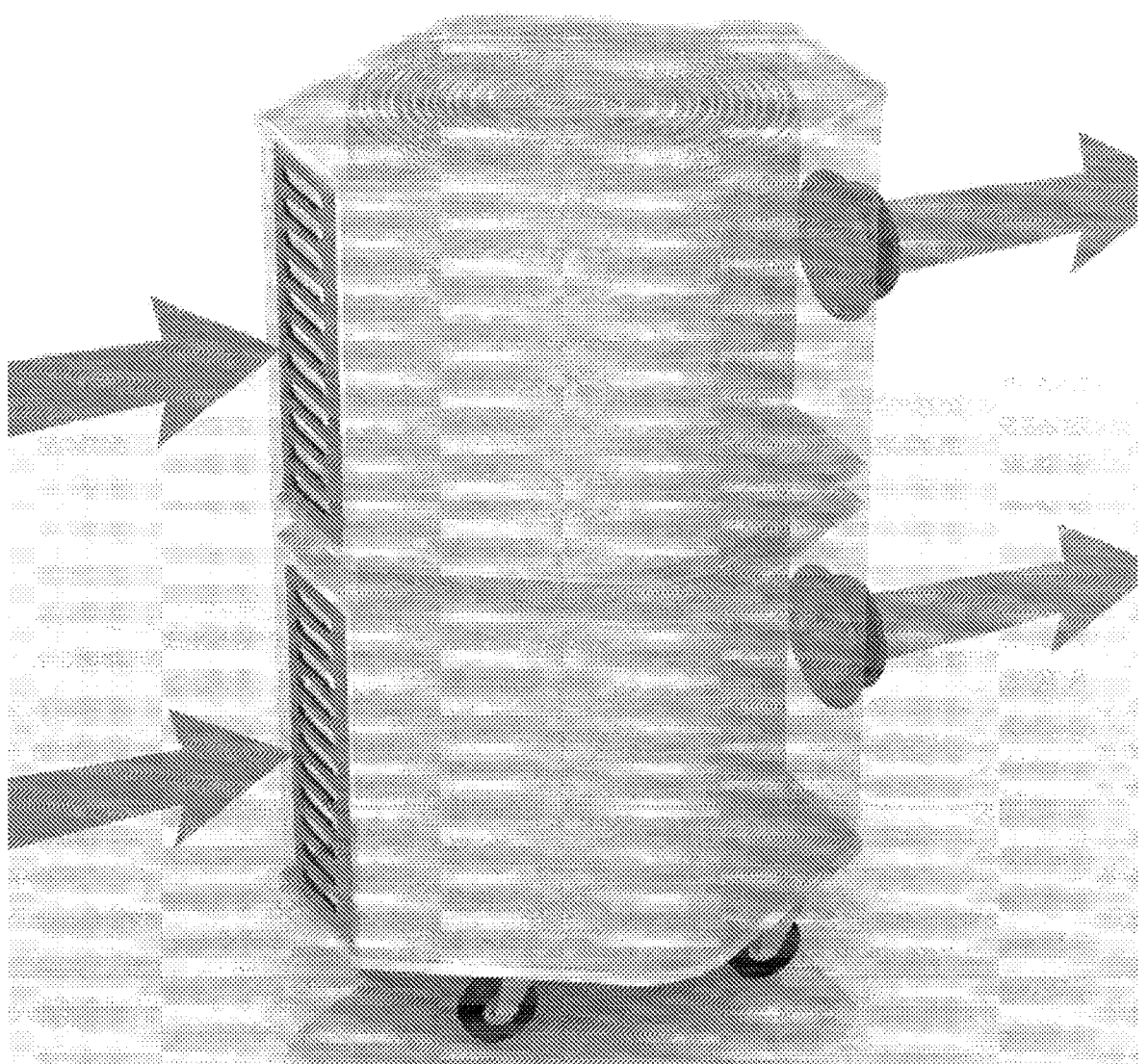
FIGS. 15A-15B show a portable room filter system in accordance with the present invention.
Figure 15B:
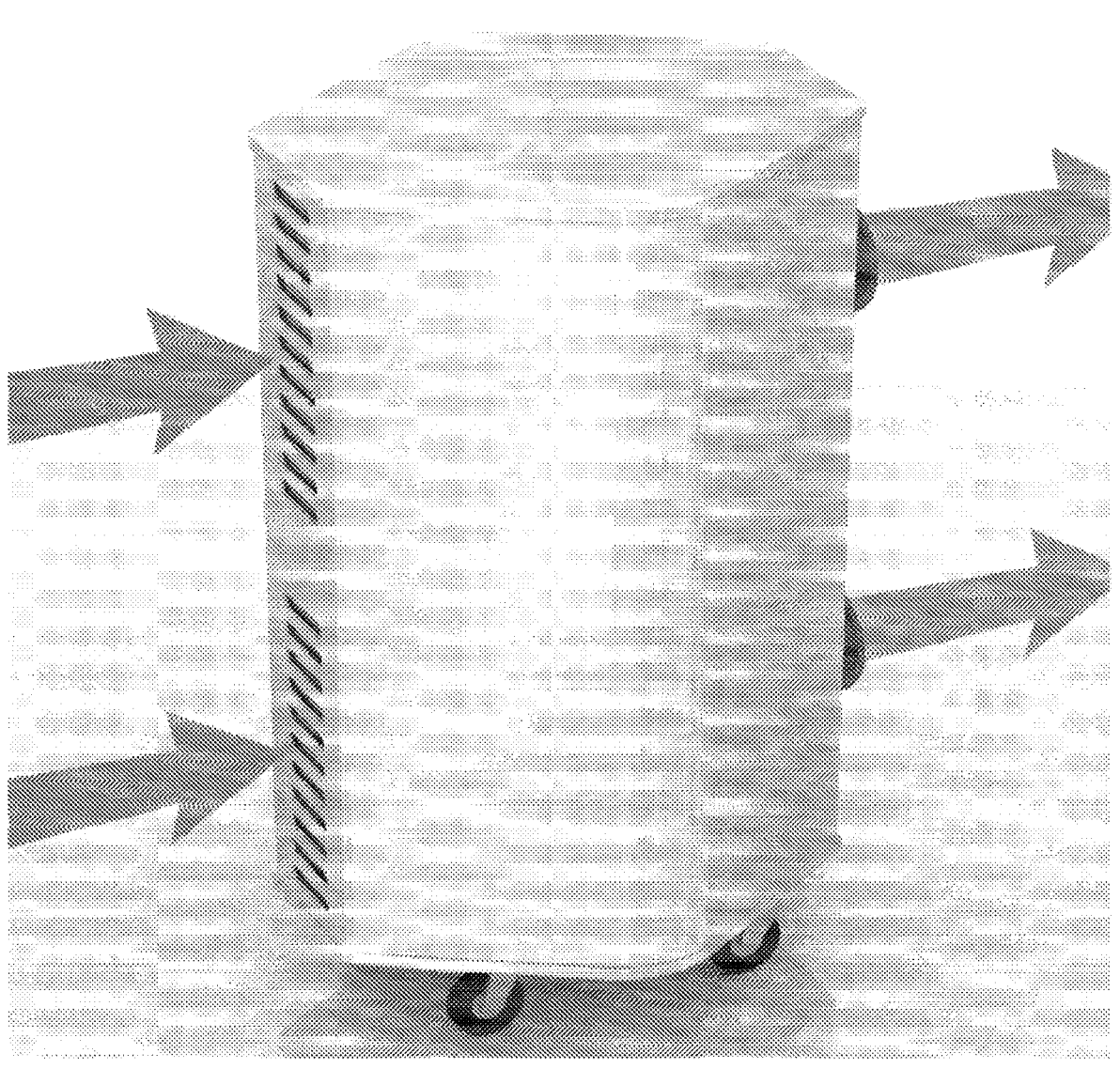

In other instantiations of the invention, these same technologies described herein can be scaled up to provide large area air purification for one or more contaminants, for example, viruses, biohazards, and other pathogens. The scaled-up system could be used to provide large volumes of safe air and could be used used in HVAC systems. Examples of this are illustrated in connection with a room filtration system (FIGS. 12A-12G), an exhale filter system for a gurney (FIGS. 13A-13D), a filter system for tented areas (FIGS. 14A-14I), and a portable filter unit for rooms or other areas (FIGS. 15A-15B). This invention, through the high efficiency methods as described herein, allows the effective removal or inactivation of pathogens from air, thus allowing the effective removal or inactivation of undesirable pathogens for those air spaces. The technologies described, once appropriately scaled, could be used in room air purifiers, homes, buildings, ships, airplanes and other structures to improve their safety via safe air quality. They can be used in two modes. In one, they could heat the air to a required temperature while making it safe to breath. In another, they merely make the air safe to breath. This flexibility helps make the invention more adaptable to retrofit to existing HVAC systems.

II. Shield & Mask Modules

1. Face Shield Module

The face shield is worn on the head with an optionally size adjustable headband. The joining method of the headband and face shield will usually not have any large openings. The air inlet can incorporate air routing features to properly direct the filtered airflow over the face of the user as needed. The face shield is equipped with one or more sets of suitable seals, (which need to restrict airflow, but do not need to be airtight, unless that is desired for the intended application) that contact the head, face and neck of the wearer as needed, for example on the forehead & sides of the face. These can be as simple as neoprene shaped strips or rubber gaskets or other suitable material that presses against the head and face. The bottom of the face shield can be equipped to have a neck gaiter made of a suitable permeable material or impermeable material with exhaust port, such port can incorporate a check valve if needed. The neck gaiter is attached to the bottom of the face shield then wraps around the neck and goes around the back of the neck of the user to insure the face shield constantly maintains a proper functional position. It can incorporate an elastic and/or elastic strap to perform this function. It can have a zipper, Velcro, button, secure latch or other suitable securing mechanism so that it joins at the back of the neck and can be separated to make the face shield easy to put on and take off, while not coming off accidentally.

The seals on the face shield can be constructed so as to prevent any openings between the edges of the mask, the seals and the head, face and neck area of the user. This prevents any outside air being drawn into the inside of the face shield and thus into the mouth and/or nose, while allowing the input air to flow over the face of the user and down the inside of the shield and out the neck gaiter. This also keeps the user from fogging the shield with their breath. It also allows the user to talk clearly and be understood. It also helps prevent the forehead and face of the user from sweating and potentially obscuring their vision.

The face shield module can incorporate differential pressure and/or airflow modes so that the pressure area that is over the wearer's face that they breath is at the highest pressure and/or airflow rate and the pressure and/or airflow rate between the sets of seals is at a lower level but is still greater than the unfiltered air surrounding the user. This feature can be used to make the probability of containments getting into the air that the user breathes much lower, since the containment would need to pass two sets of seals, not one. Various views of the face shield module are shown in FIGS. 1D-1E, 1G-1H, and 1K-IN.

2. Mask Module

Any suitable mask (preferably with an exhaust port w/a check valve, note that a preferred instantiation is an N95 mask) can be used instead of the face shield. If the mask is permeable, it does not need an exhaust port w/check valve. You put an air input fitting that is reasonably sealed through the mask (which is easy to retrofit to many existing masks, such as N95 masks) and connect it to a suitable instantiation of the fan/filter/air outlet assembly via a flexible air input tube. The location of the input fitting can preferentially be located so as to not affect proper functioning of the mask. The tube can be made of any suitable material, such as flexible plastic, flat self-inflating woven materials, or corrugated paper in disposable applications. The delivery tube is ideally very lightweight to prevent applying undesirable forces to the face mask. One preferred instantiation utilizes a corrugated thin wall polycarbonate tube. The mask is then operating under positive pressure and therefore any leaks in the mask due to poor fitment or knocking the mask ajar are either minimized or negated. The advantage of this approach is that you eliminate manufacture of the face shield assembly as a blocking point for mass production. It also makes many masks, such as N95 masks more comfortable to wear, since the constant flow of filtered air prevents humidity building up inside the mask, as often occurs. This helps prevent the softening and flow of mucus from the nostrils, which can make the mask more unpleasant and difficult to use.

Figure 1C:
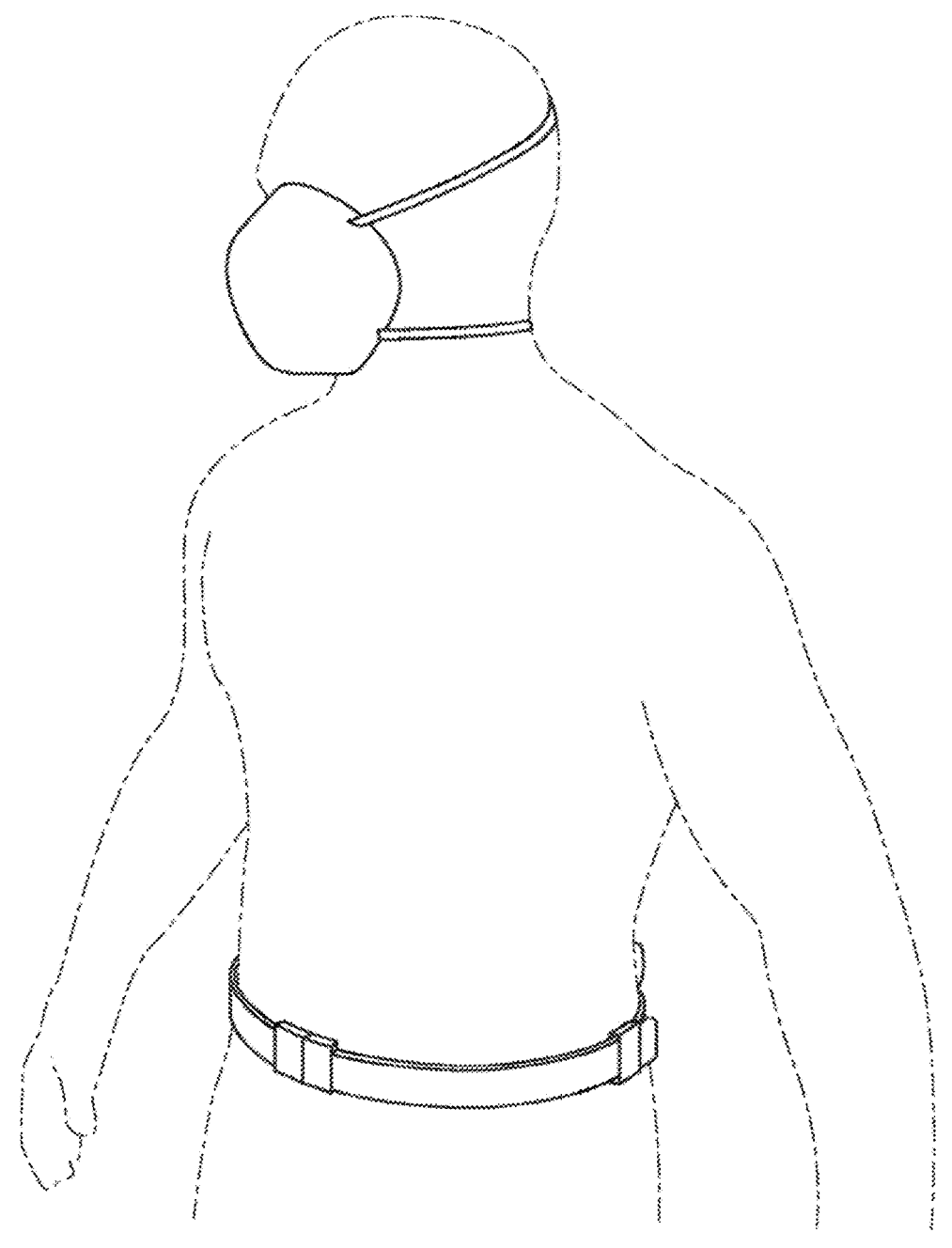
Figure 1D:
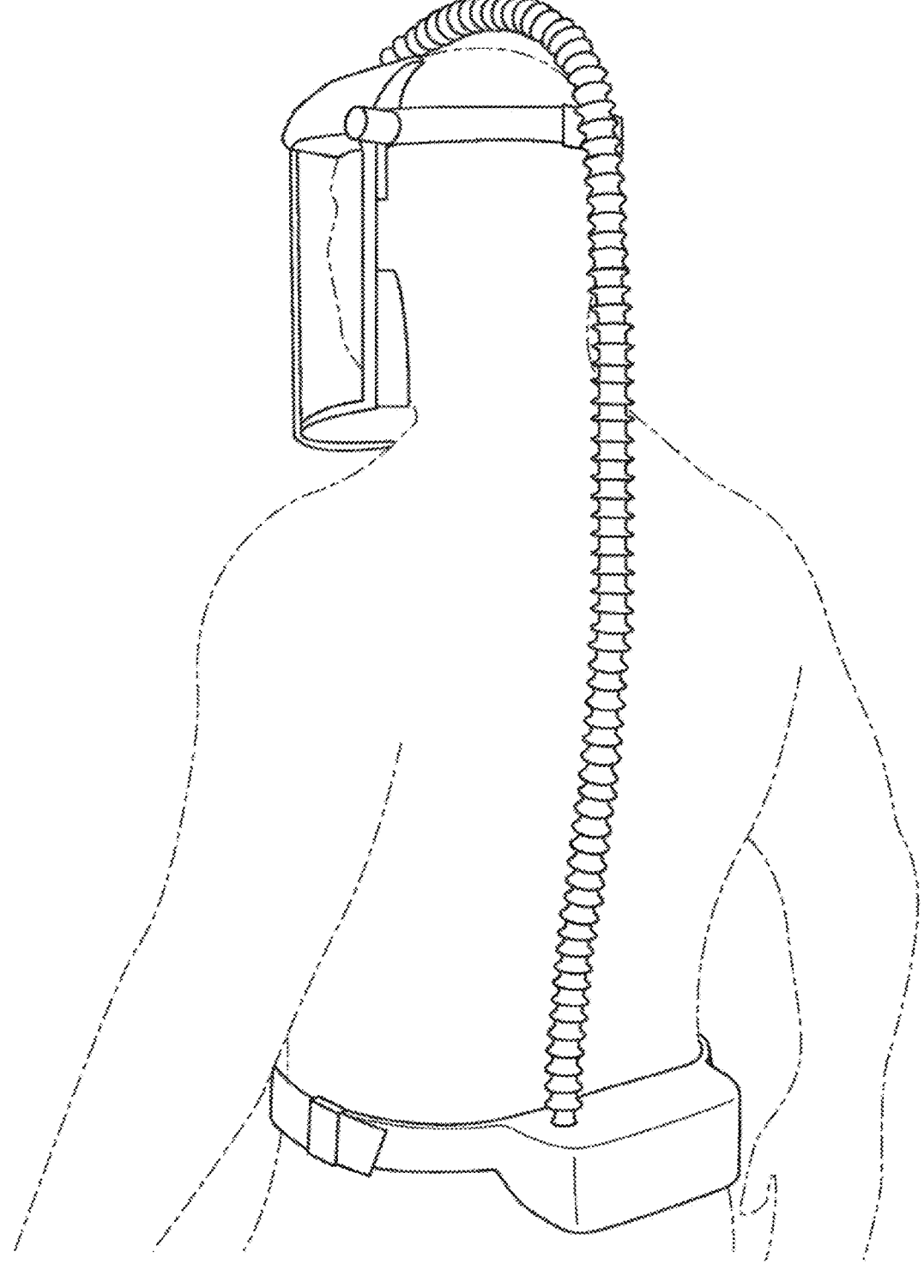
Figure 1E:
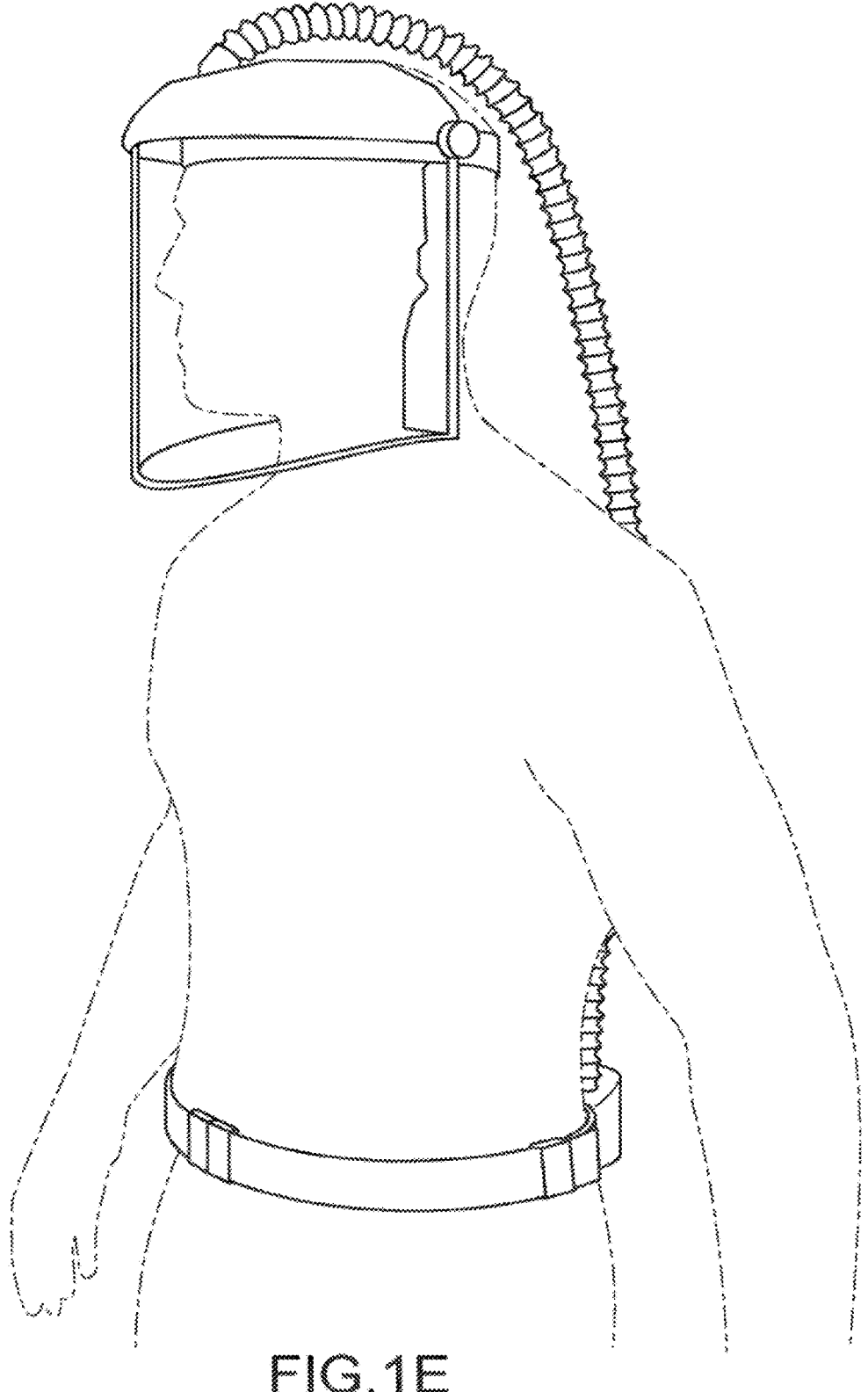
Figure 1F:
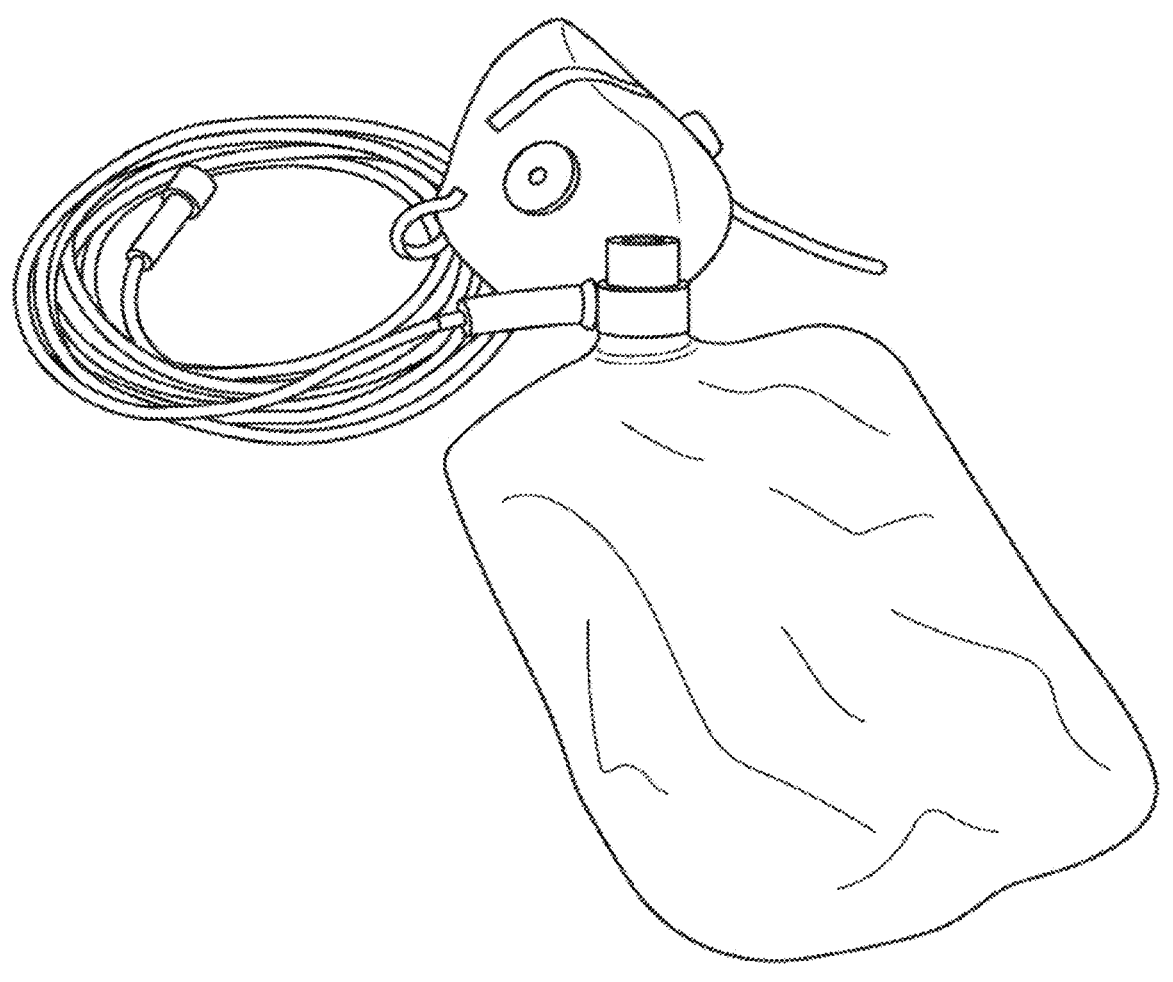
Figure 1G:
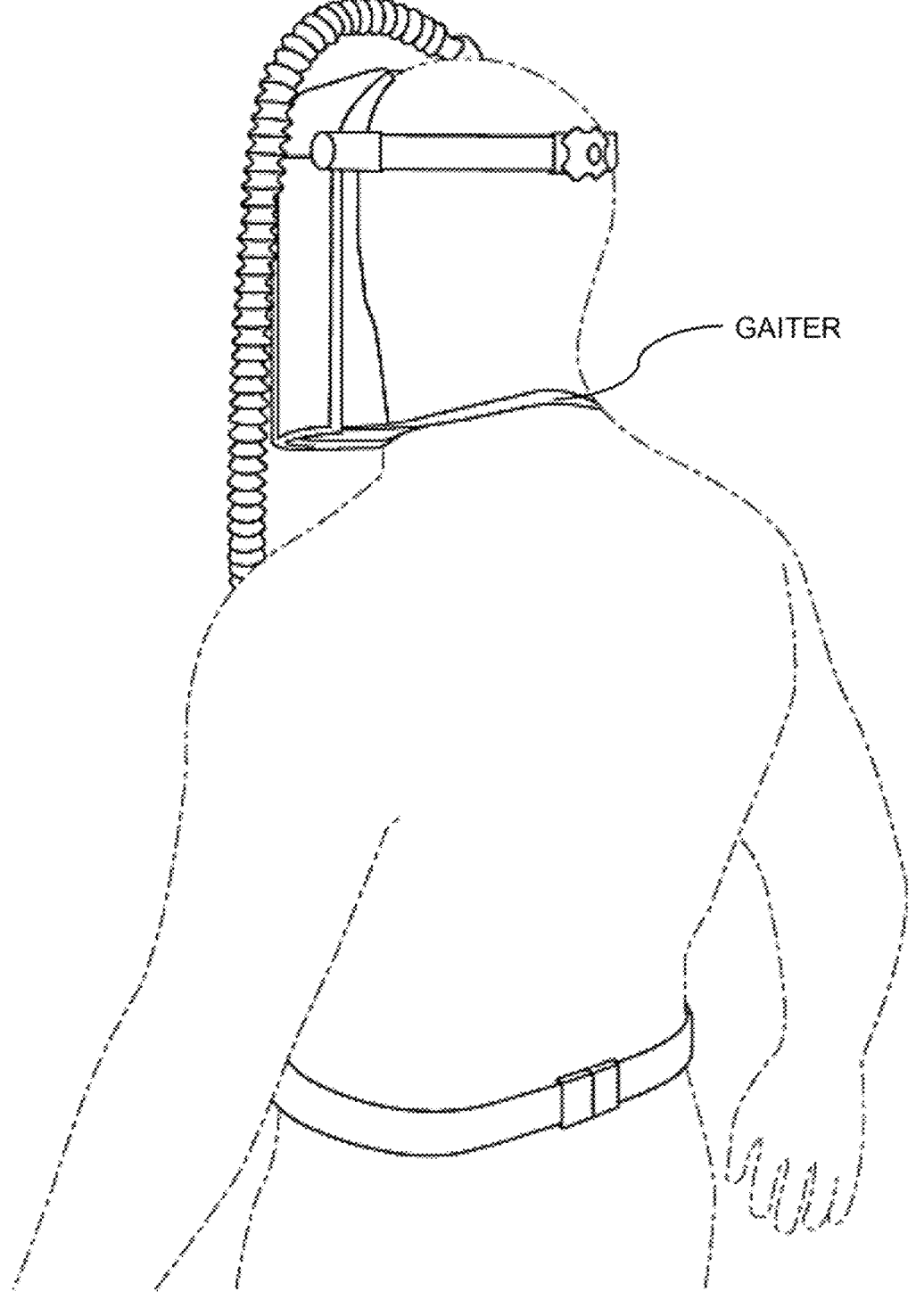
Figure 1H:
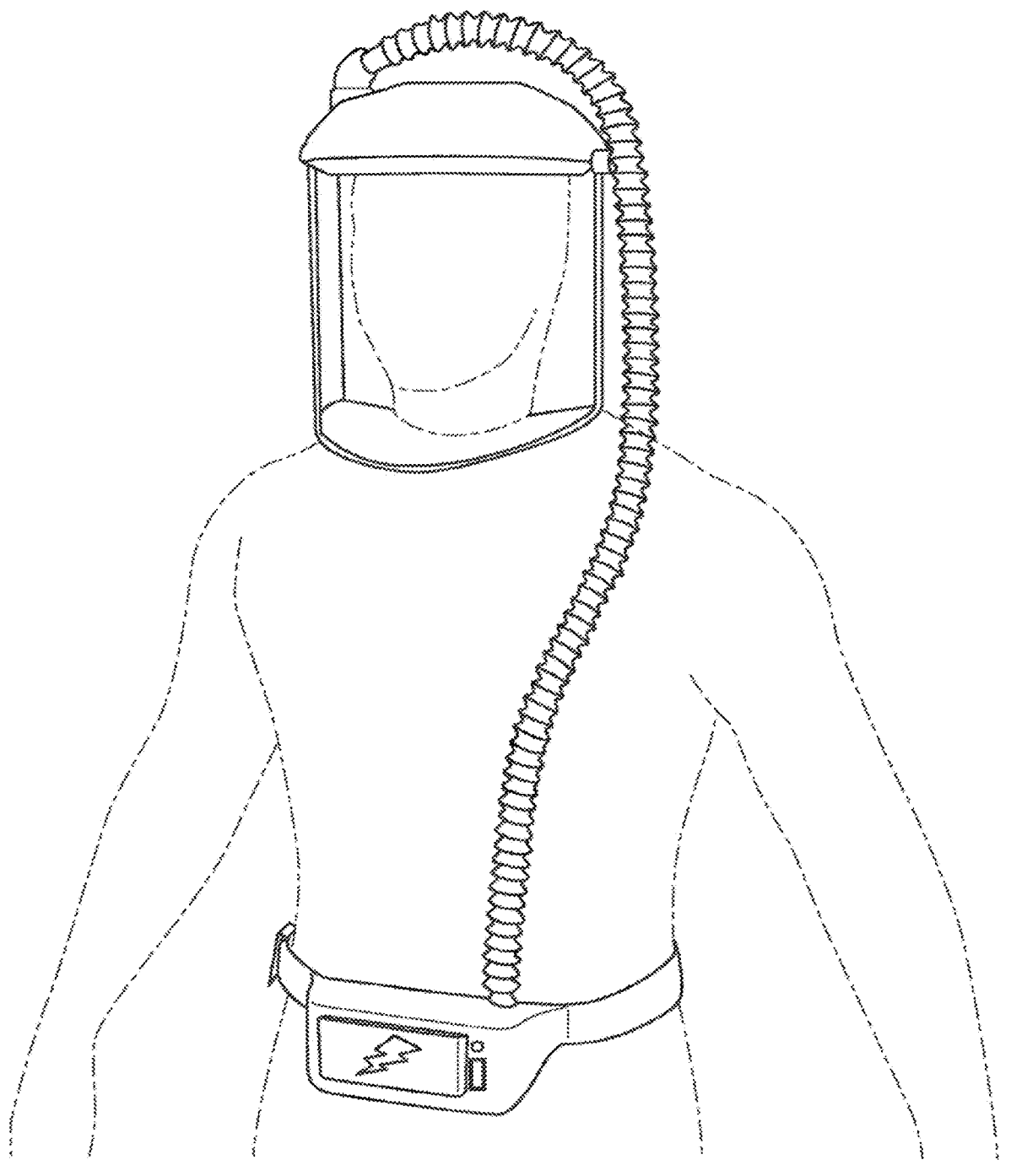
Figure 1I:
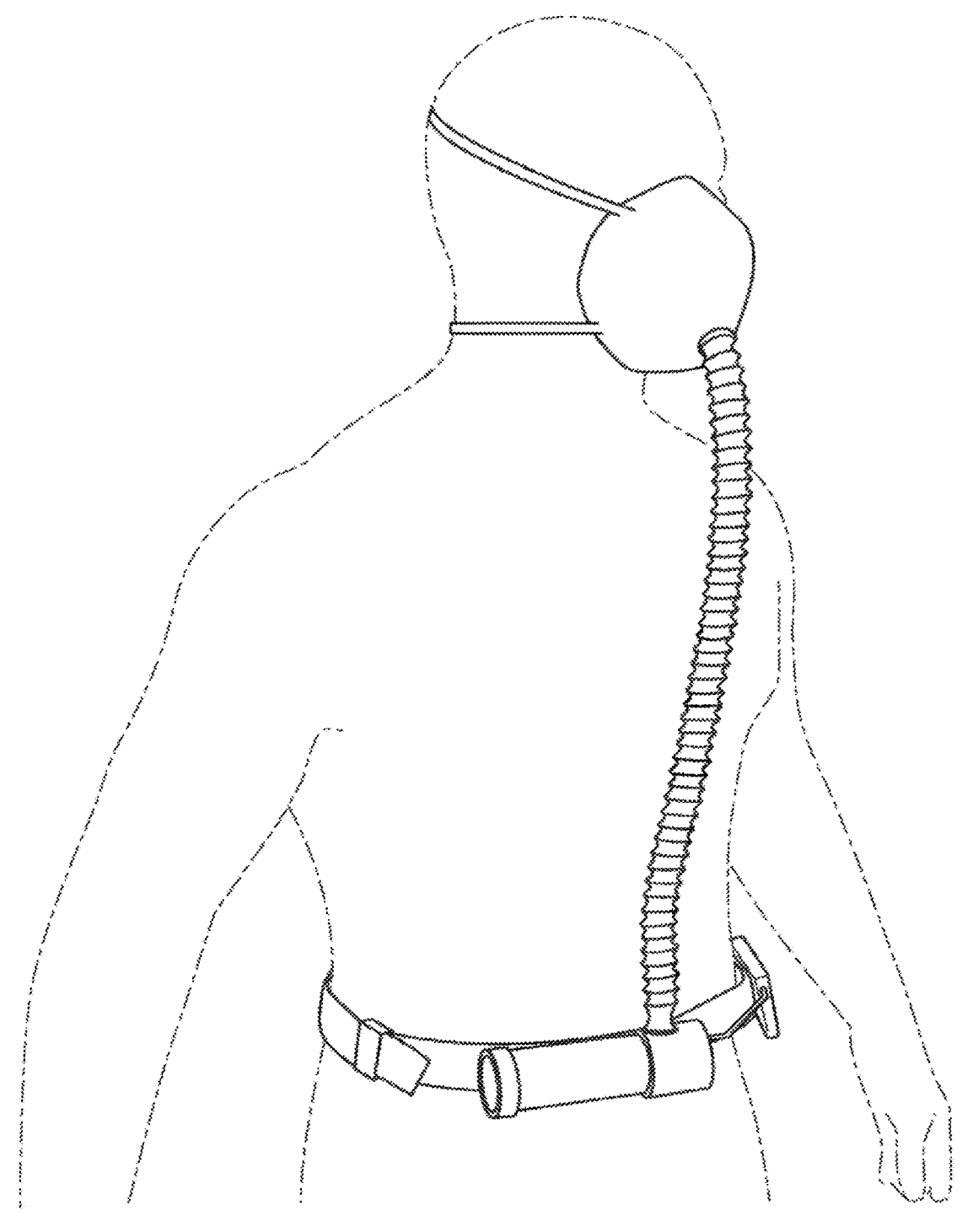
Figure 1J:
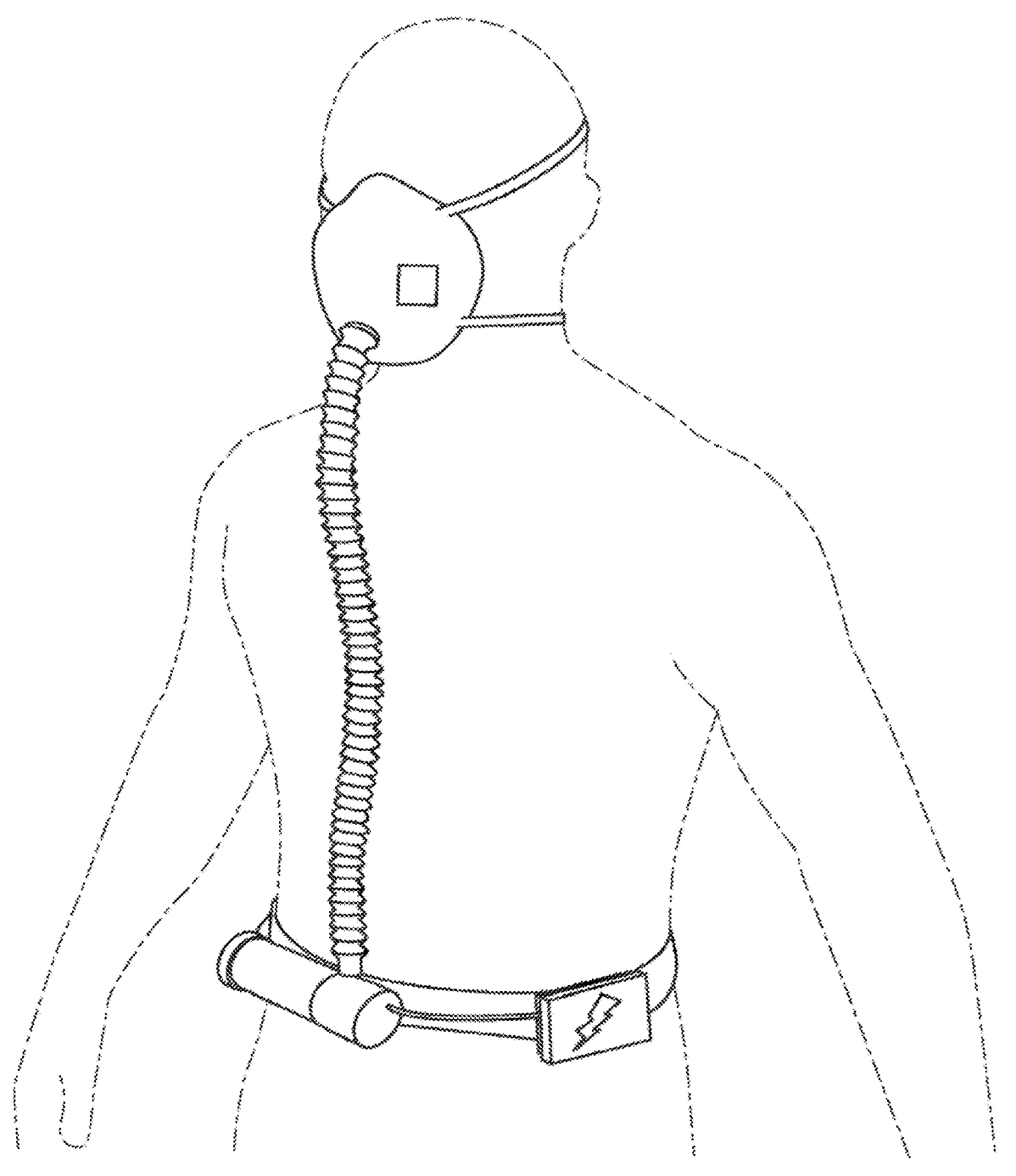
Figure 1K:
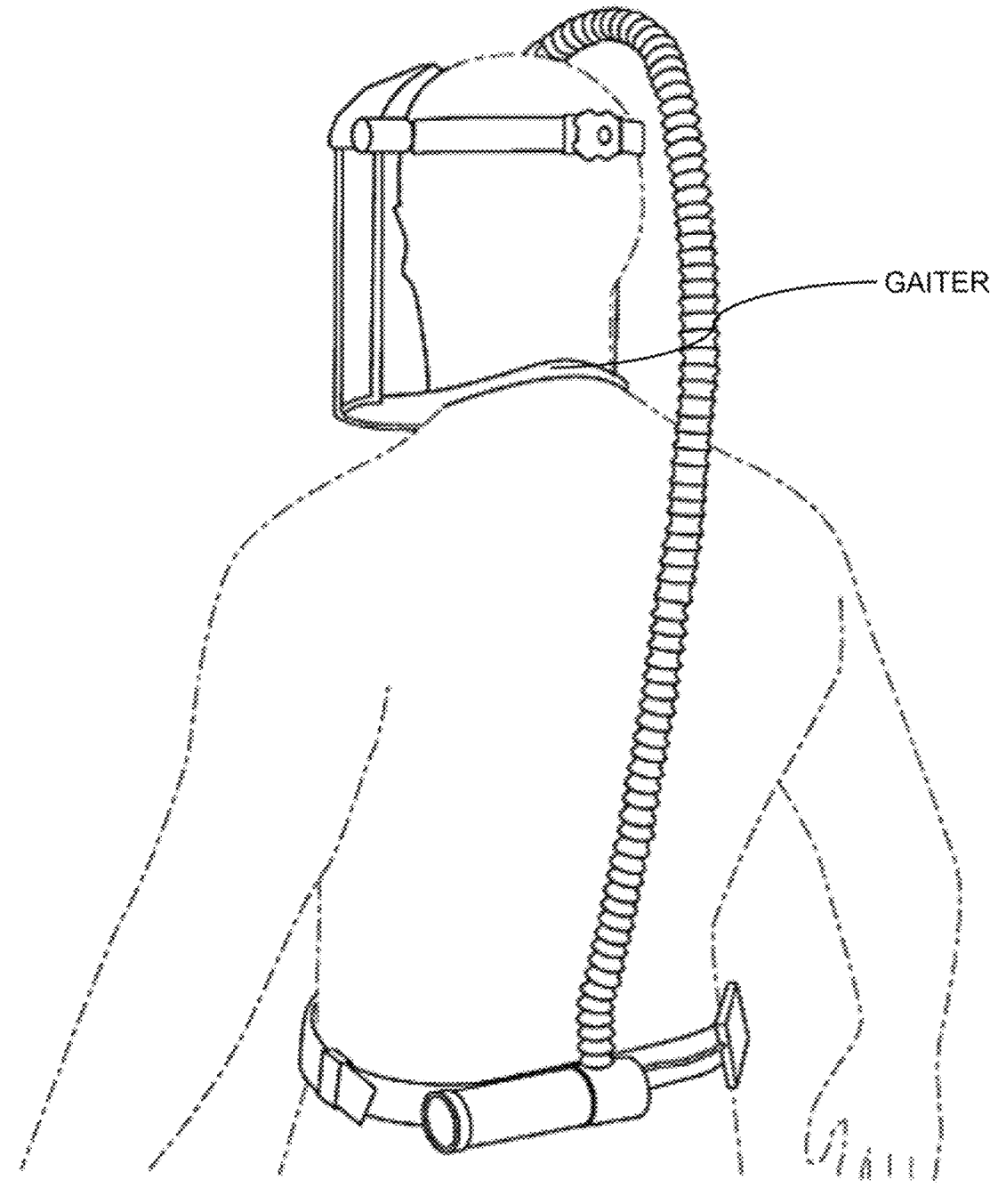
Figure 1L:
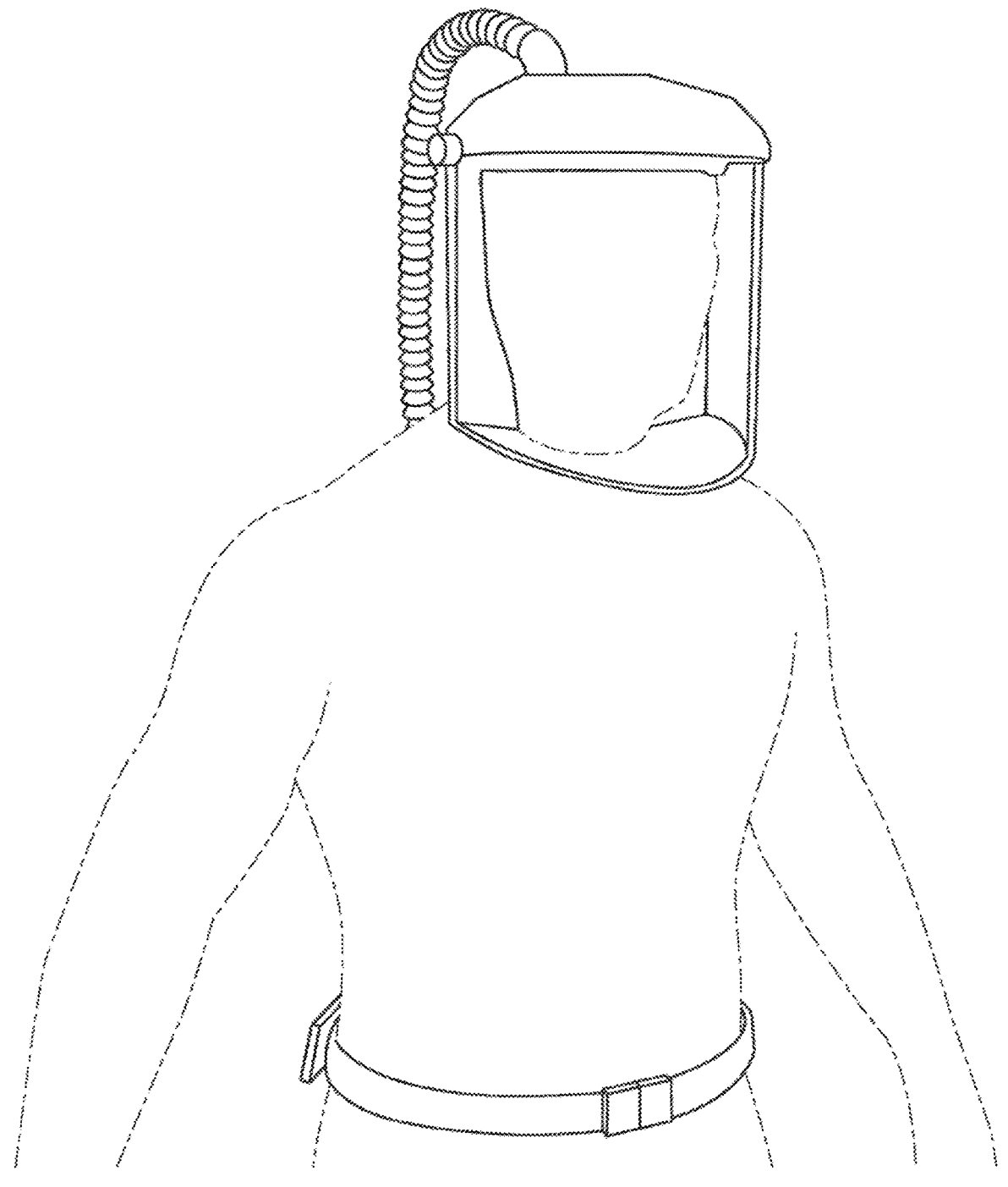
Figure 1M:
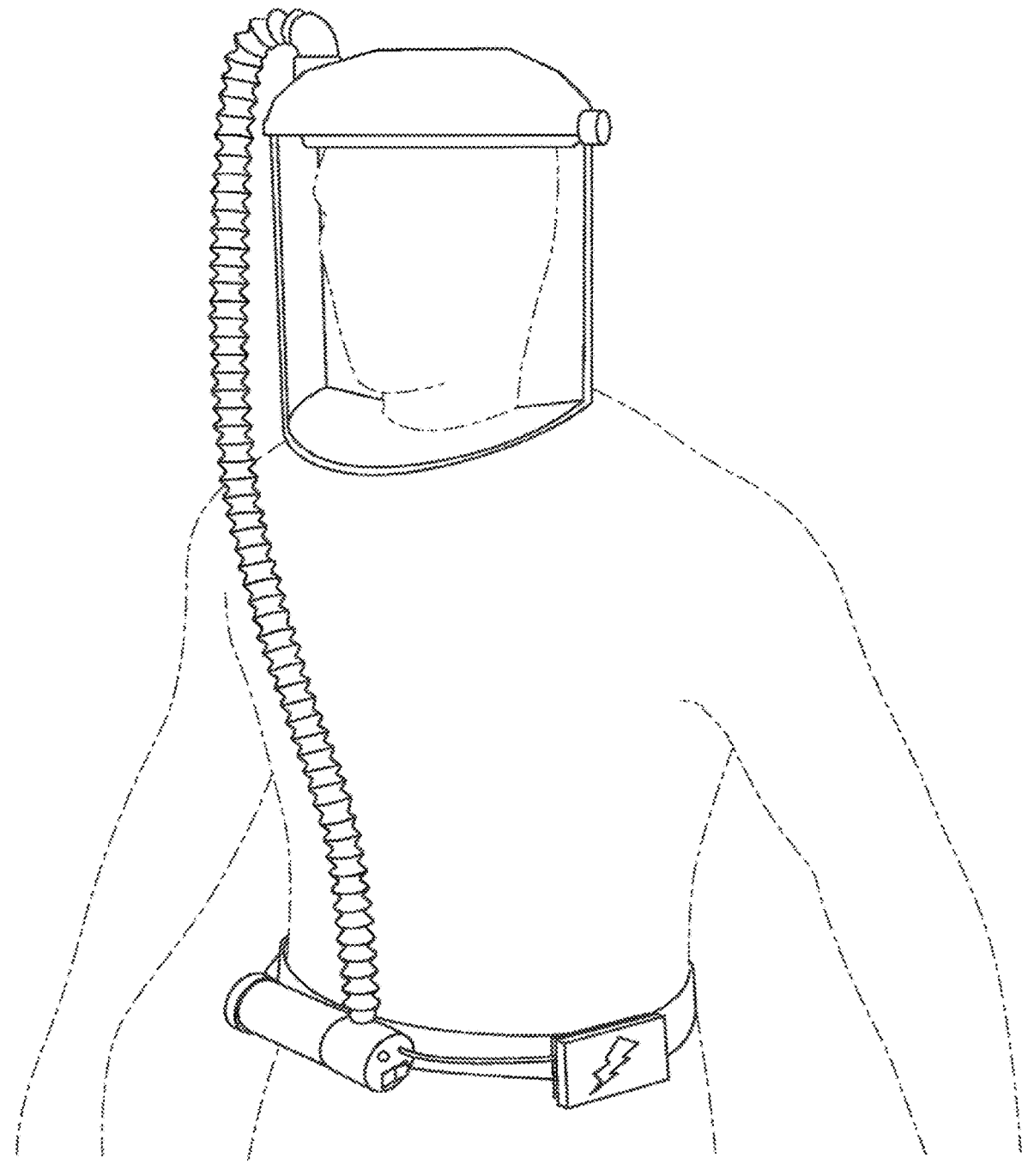
Figure 1N:
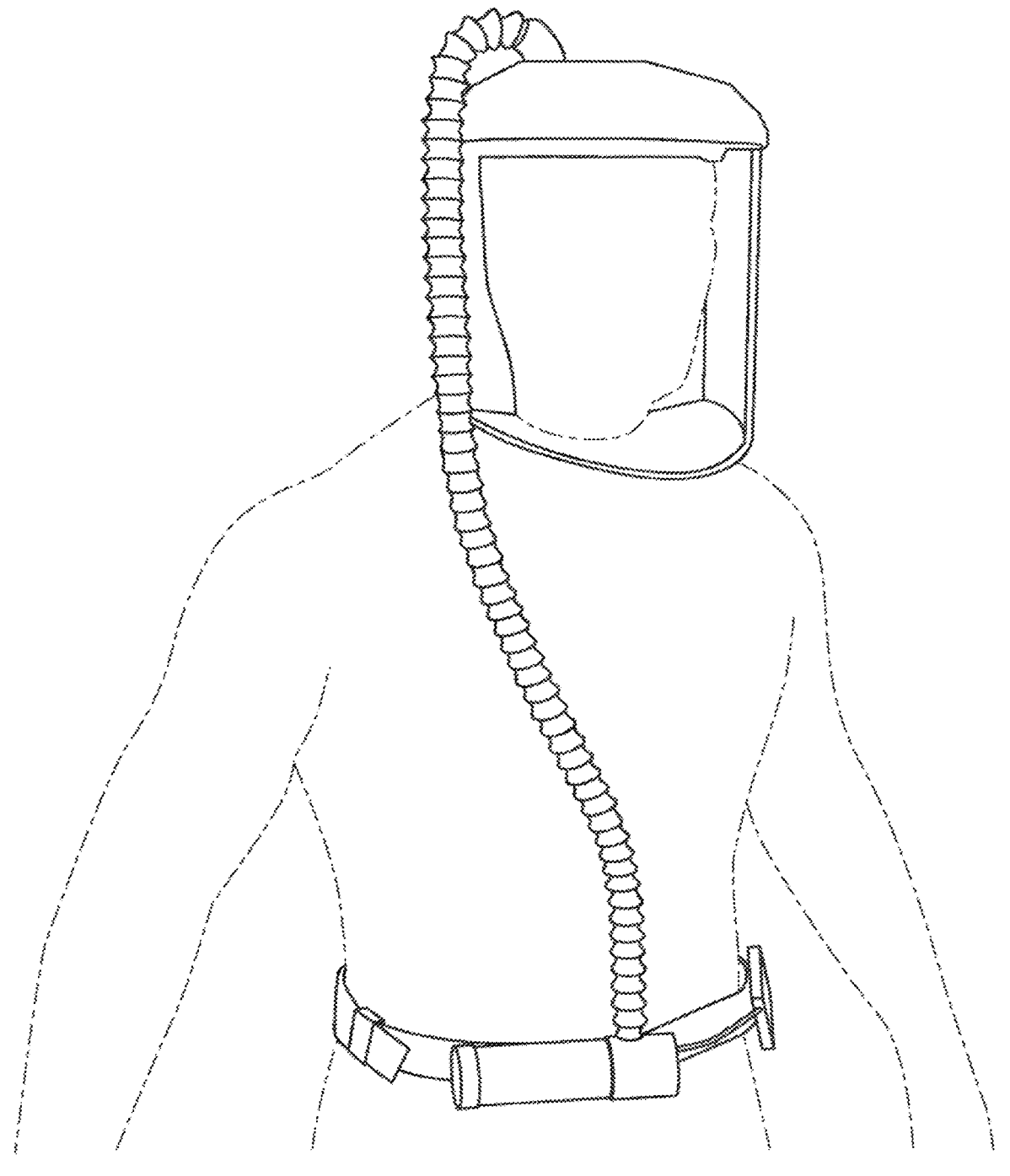
Figure 2A:
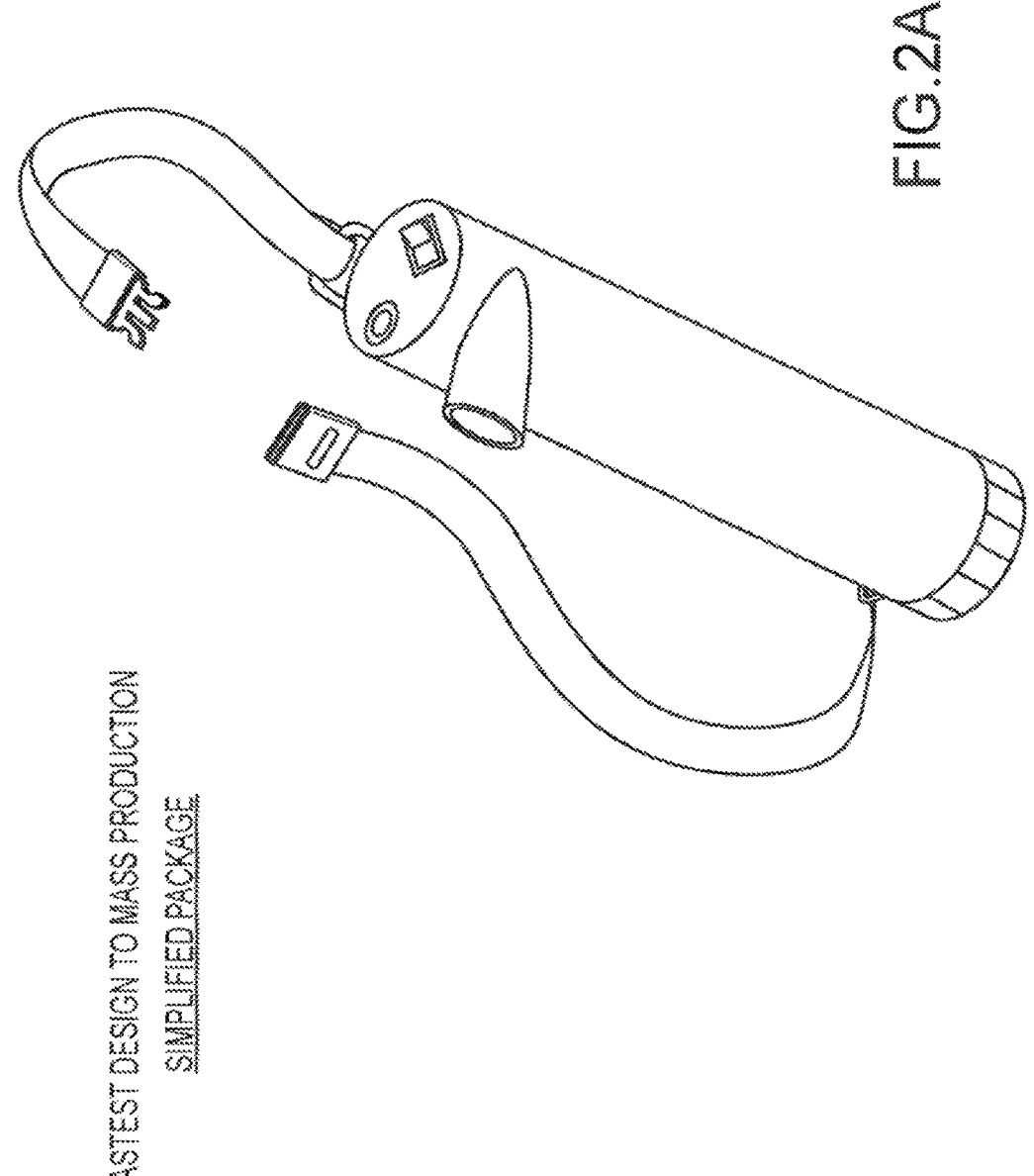
Figure 2B:
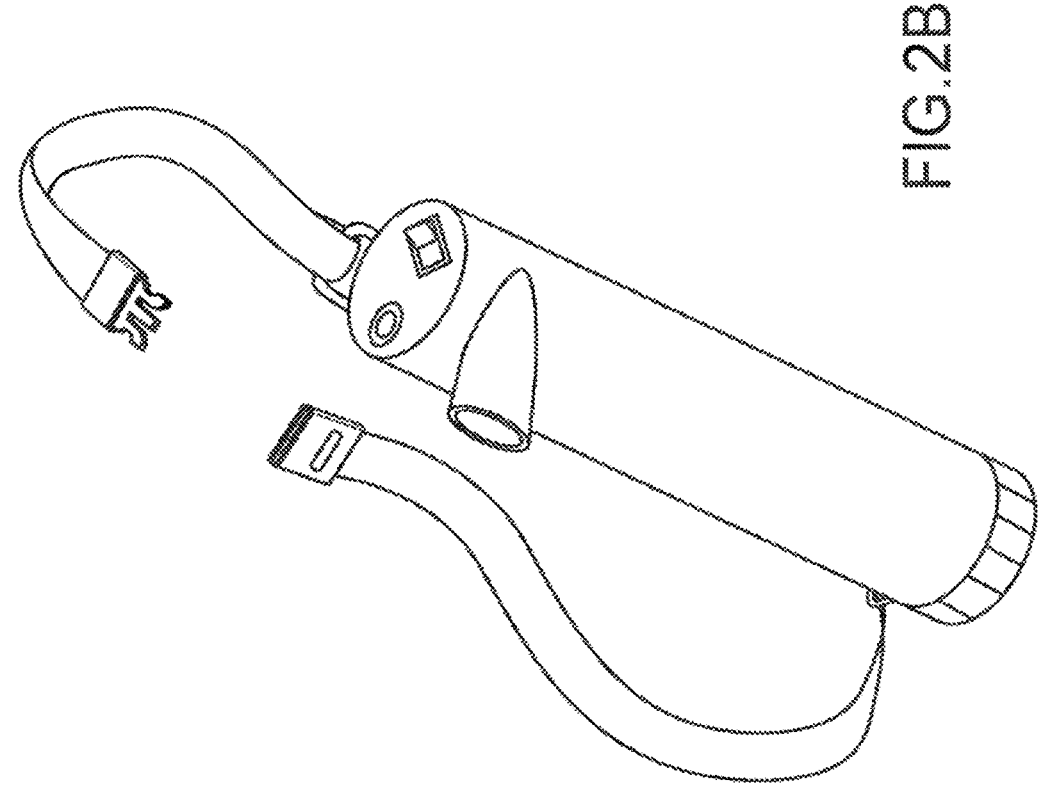
Figure 2C:
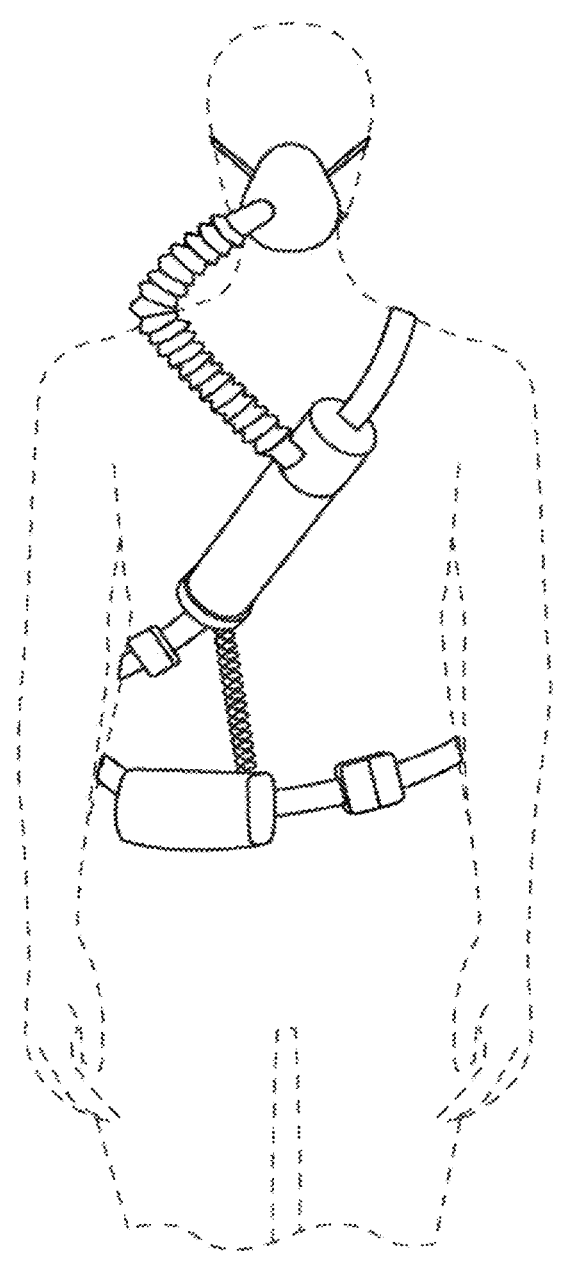
Figure 2D:
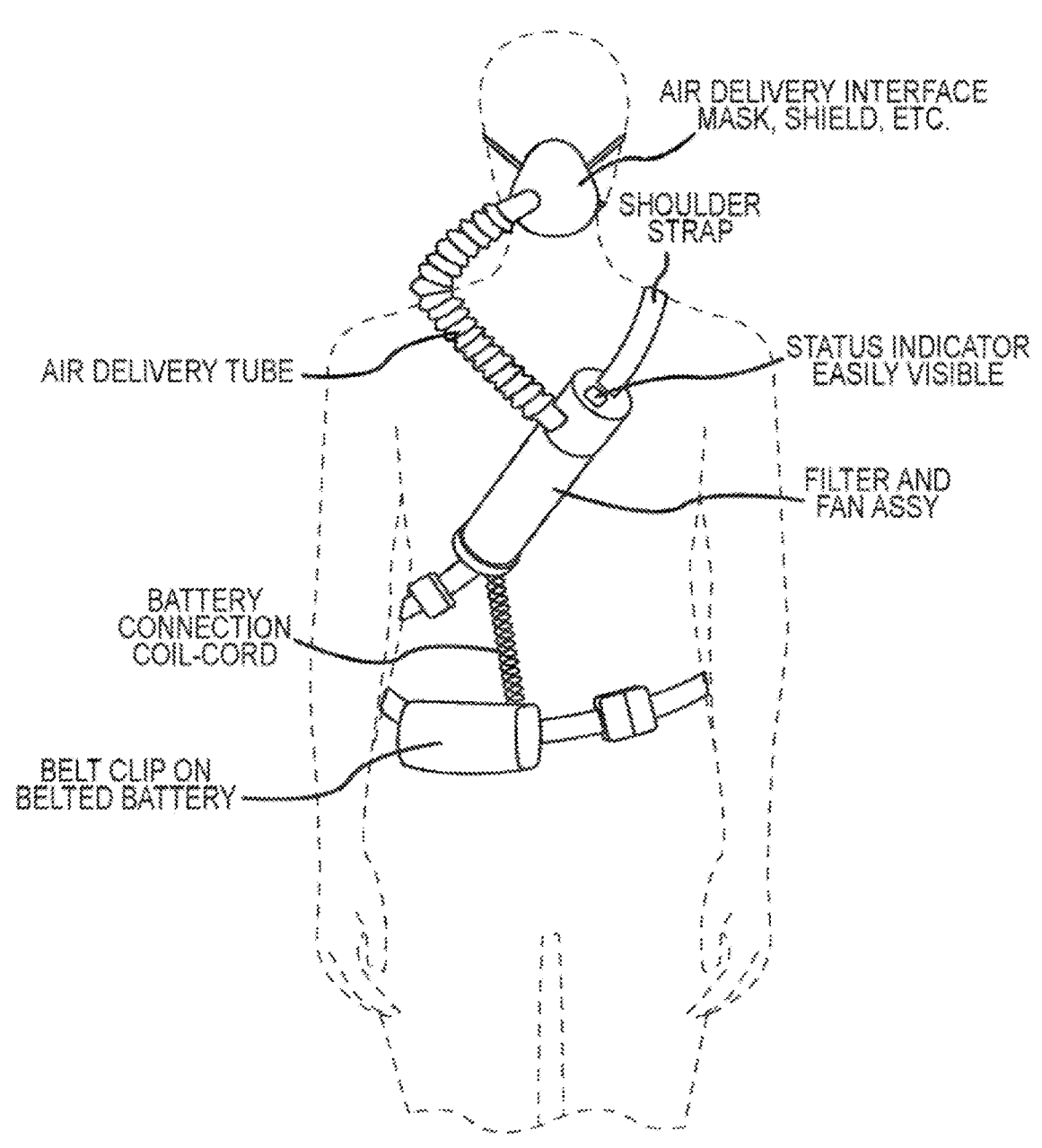
Figure 2F:
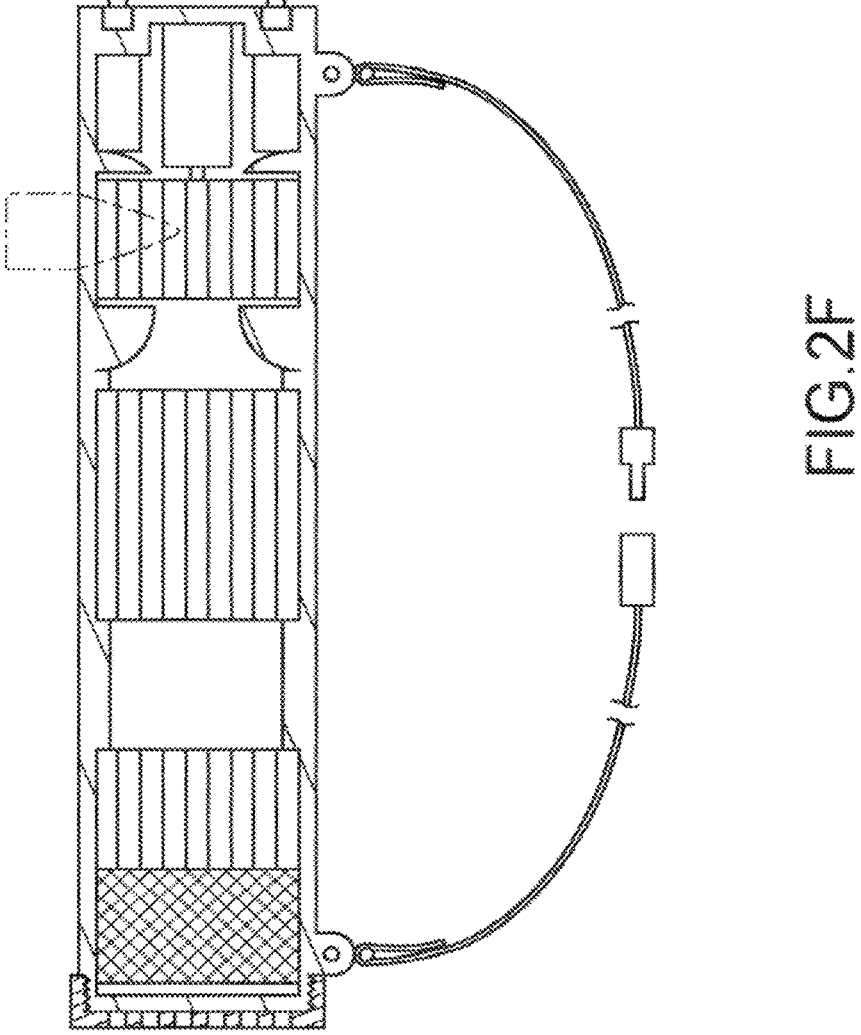
Figure 3A:
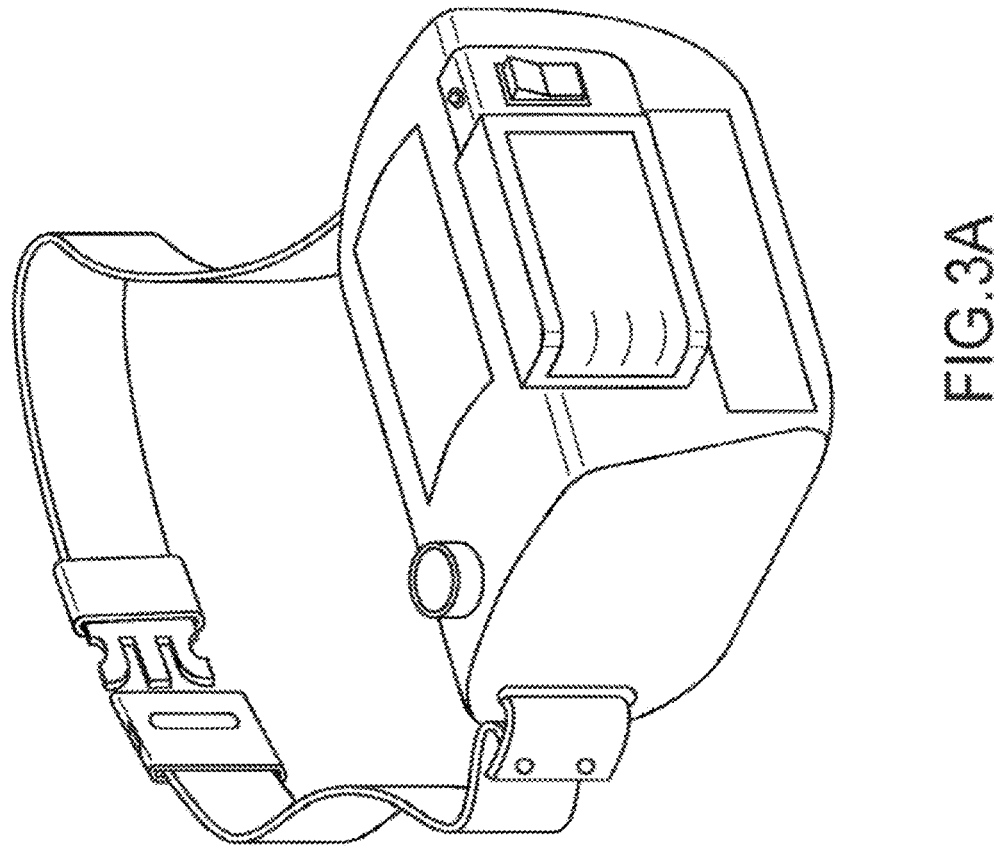
Figure 3B:
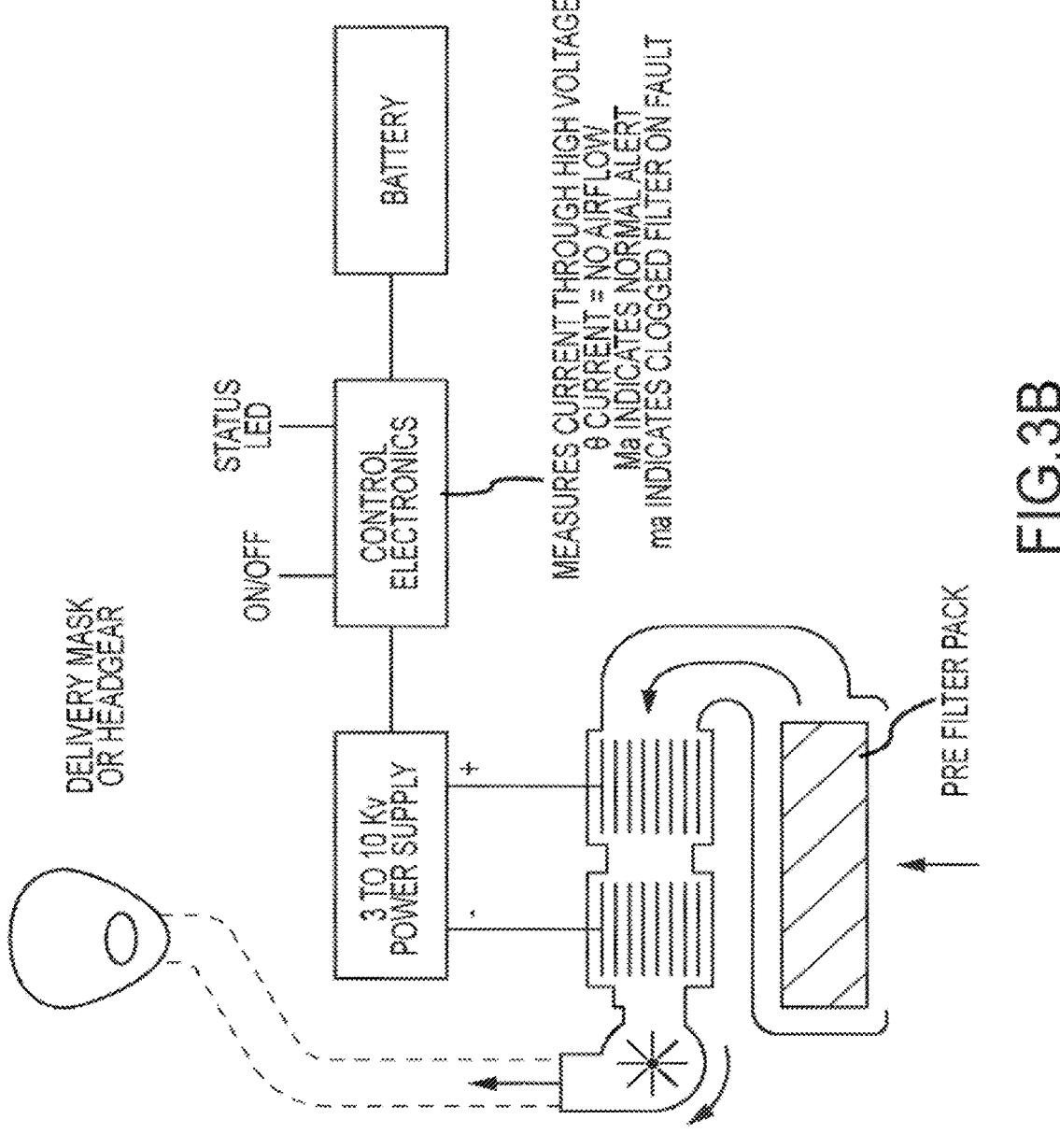
Figure 3C:
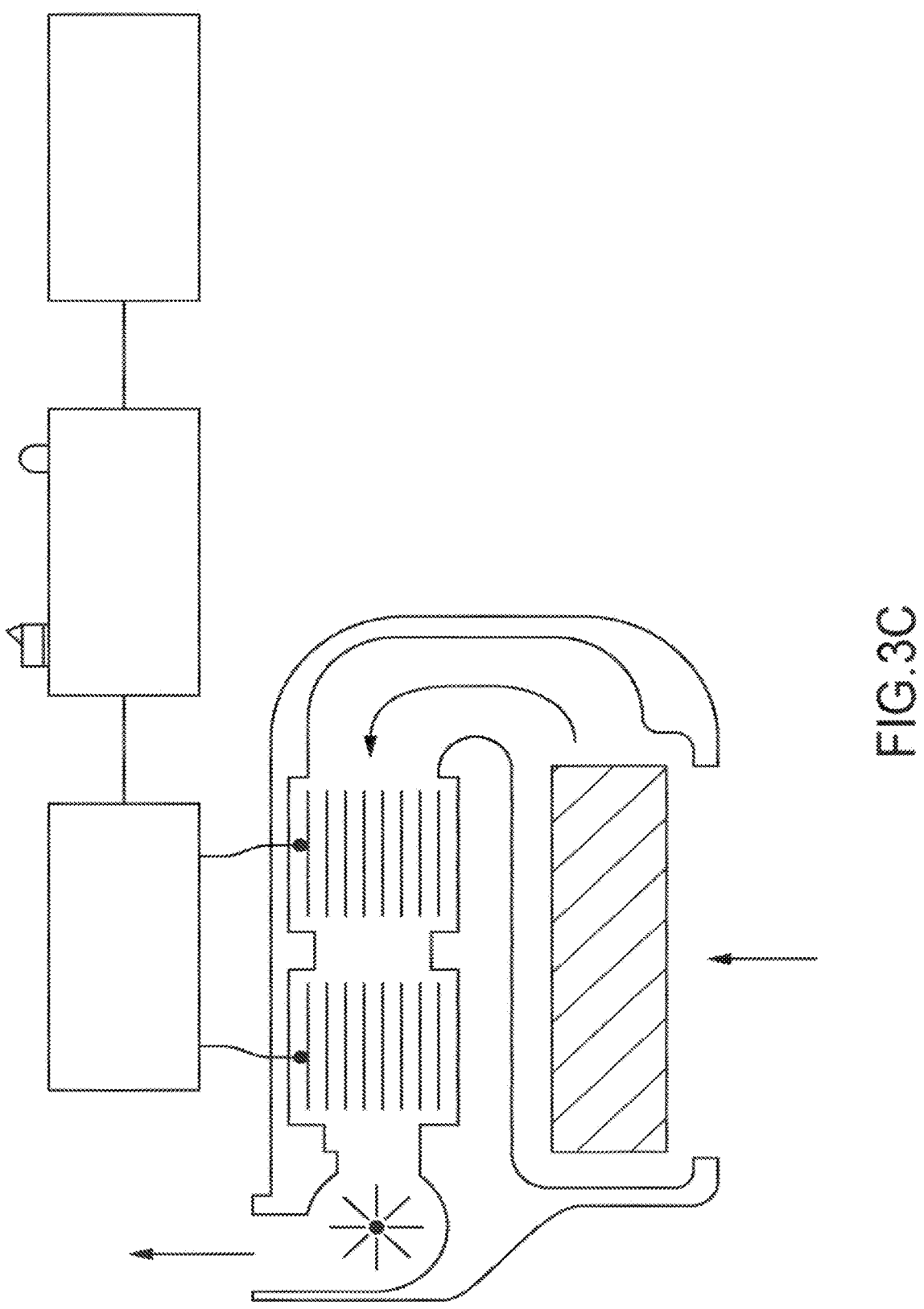
Figure 3D:
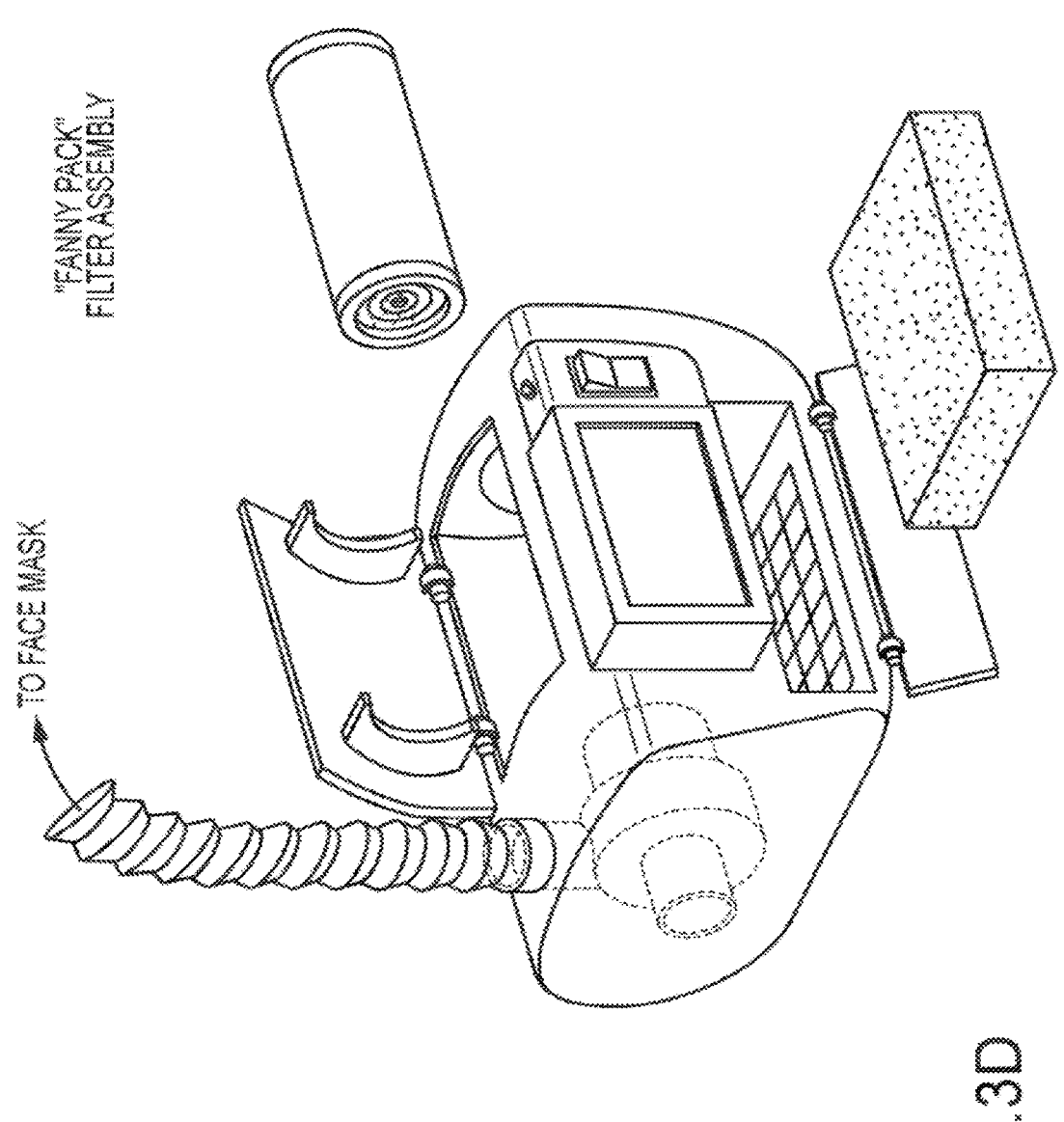
Figure 3E:
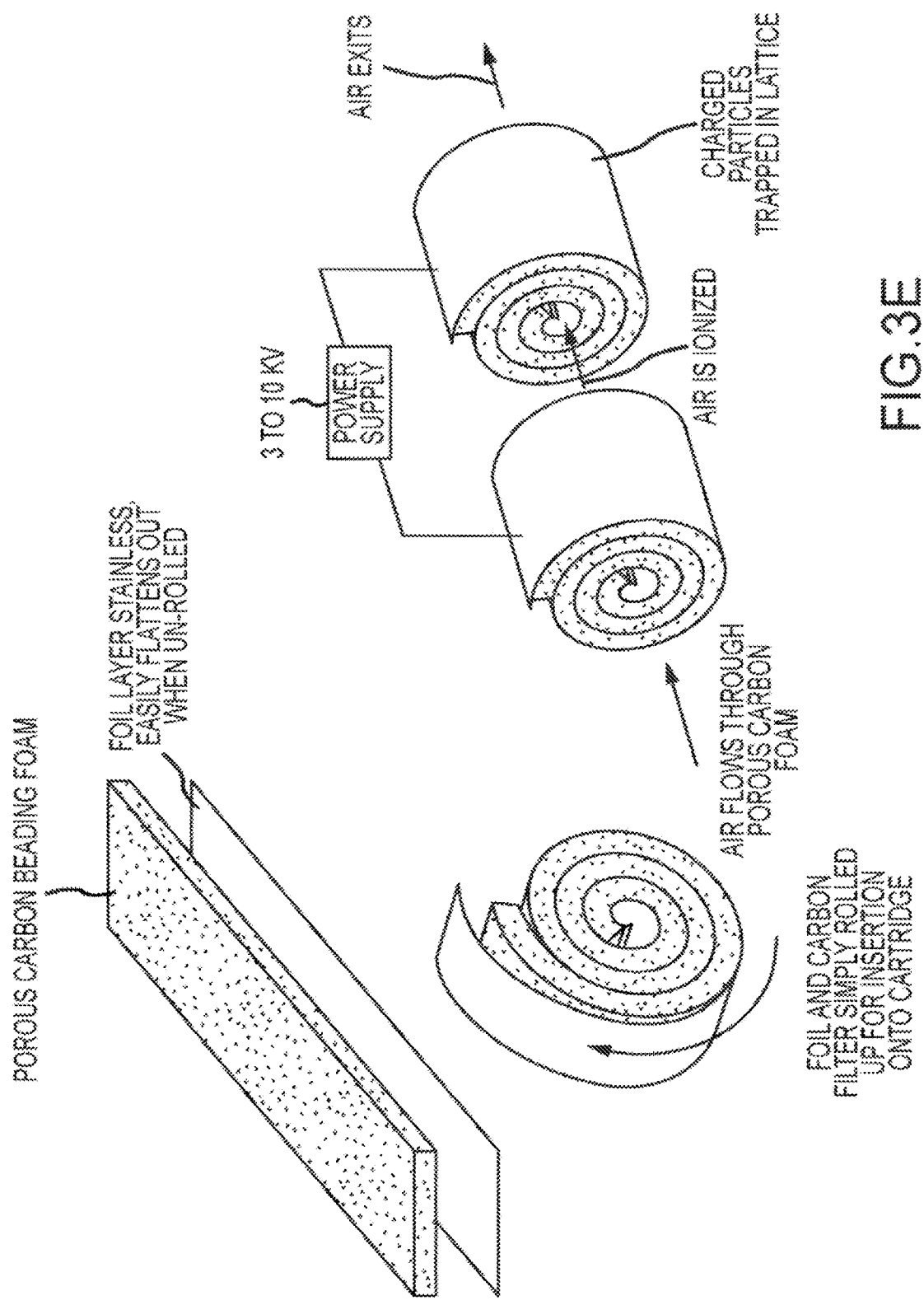
Figure 3F:
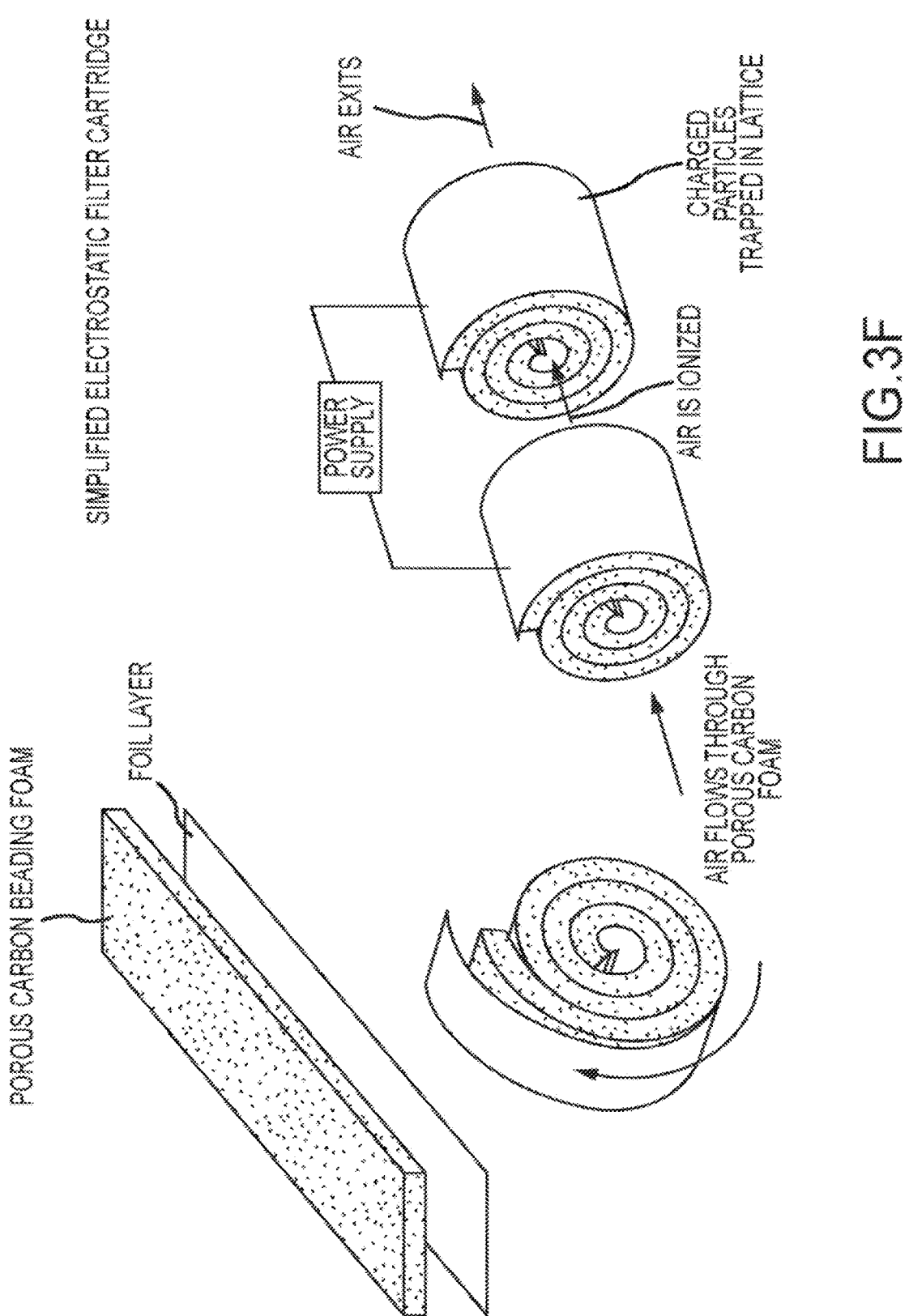
Figure 3G:
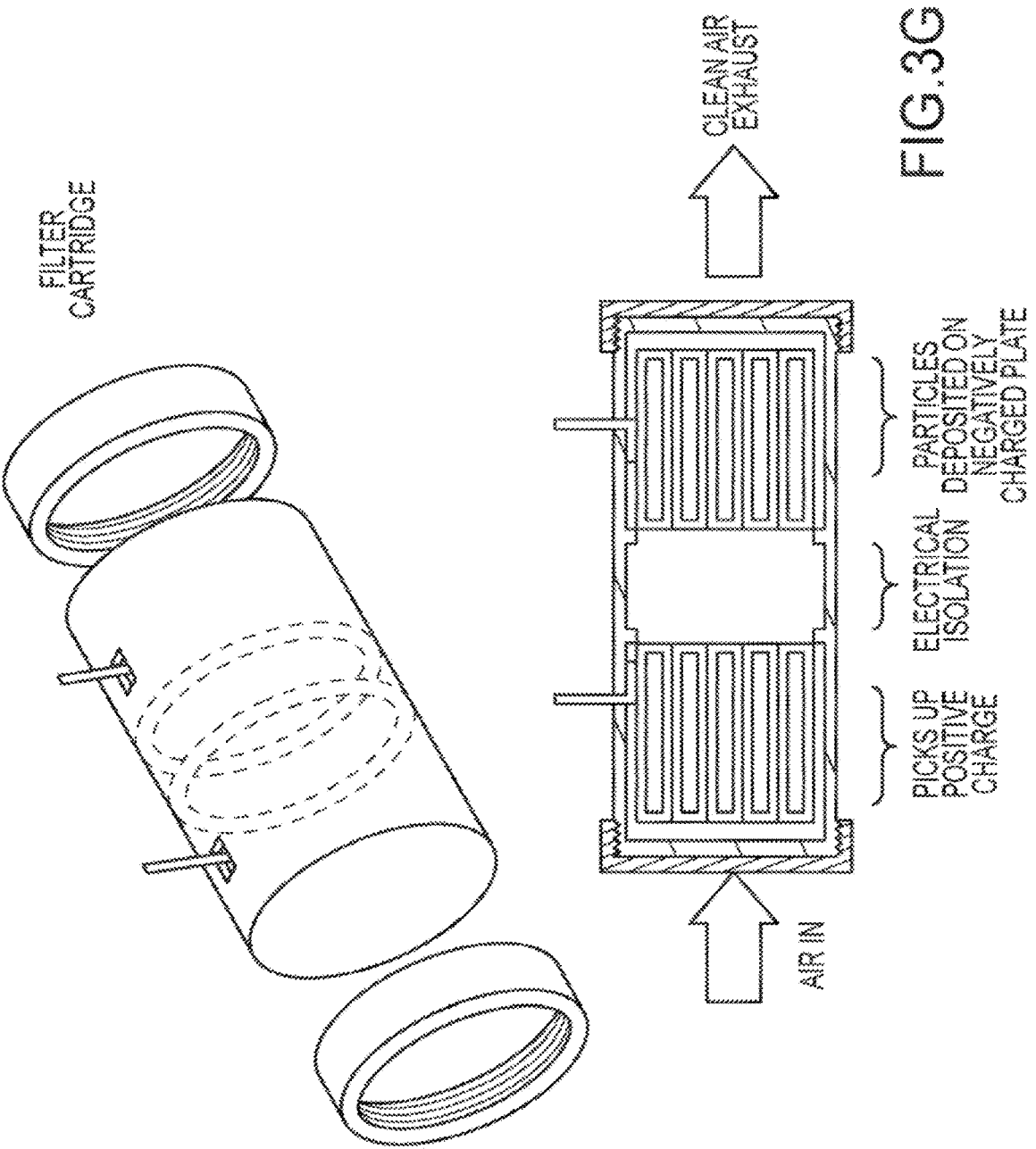
Figure 3H:
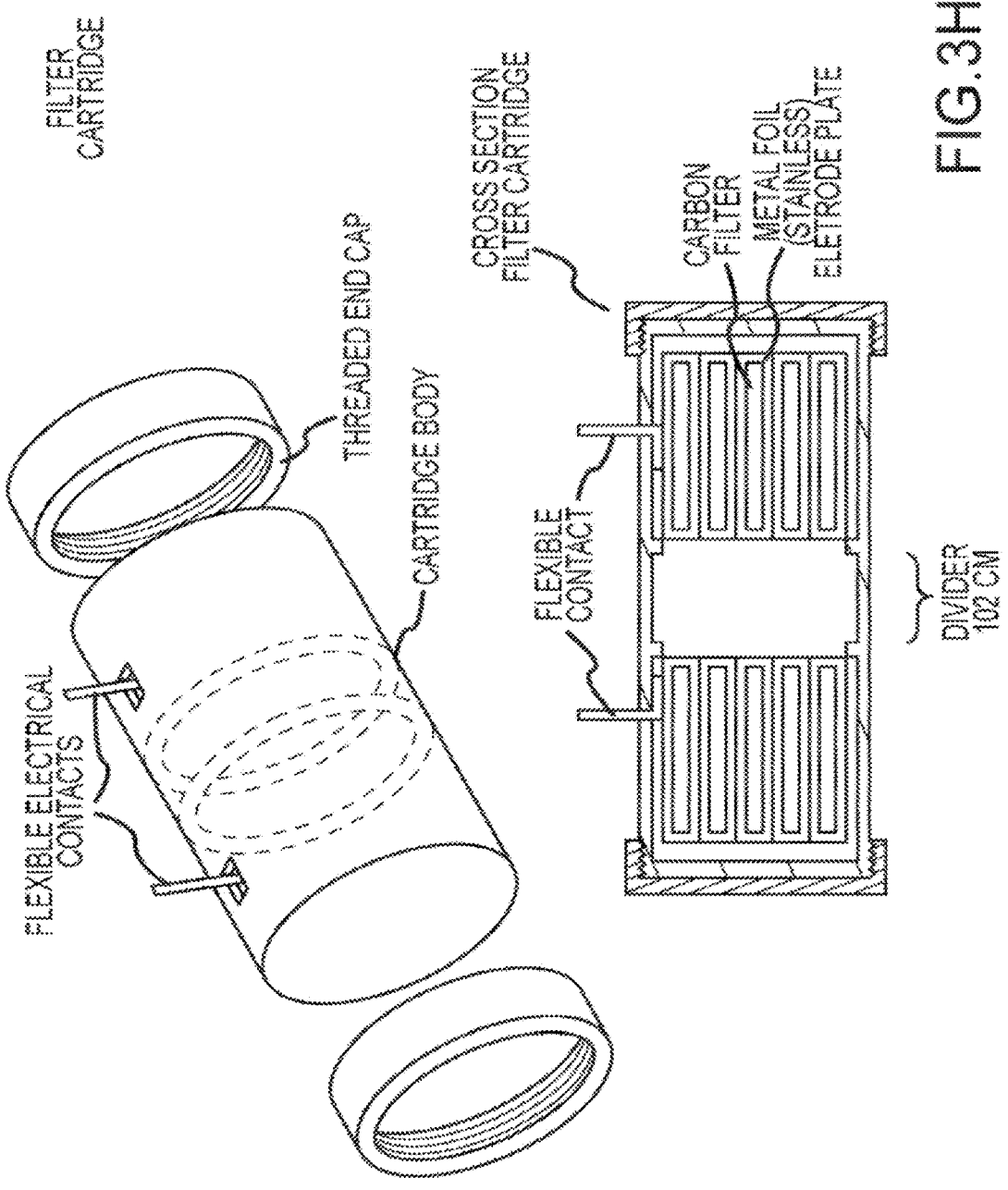
Figure 31:
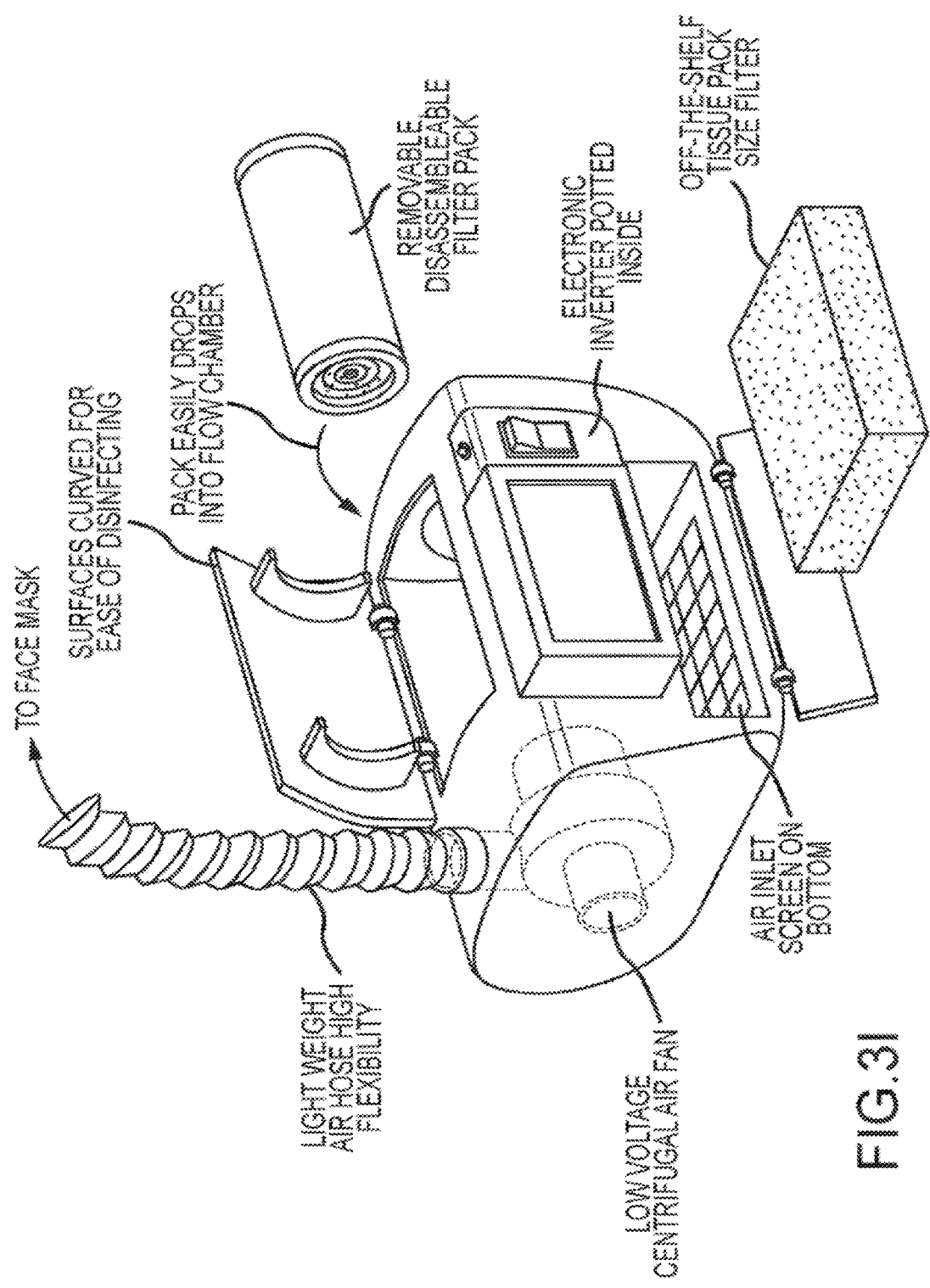
Figure 3J:
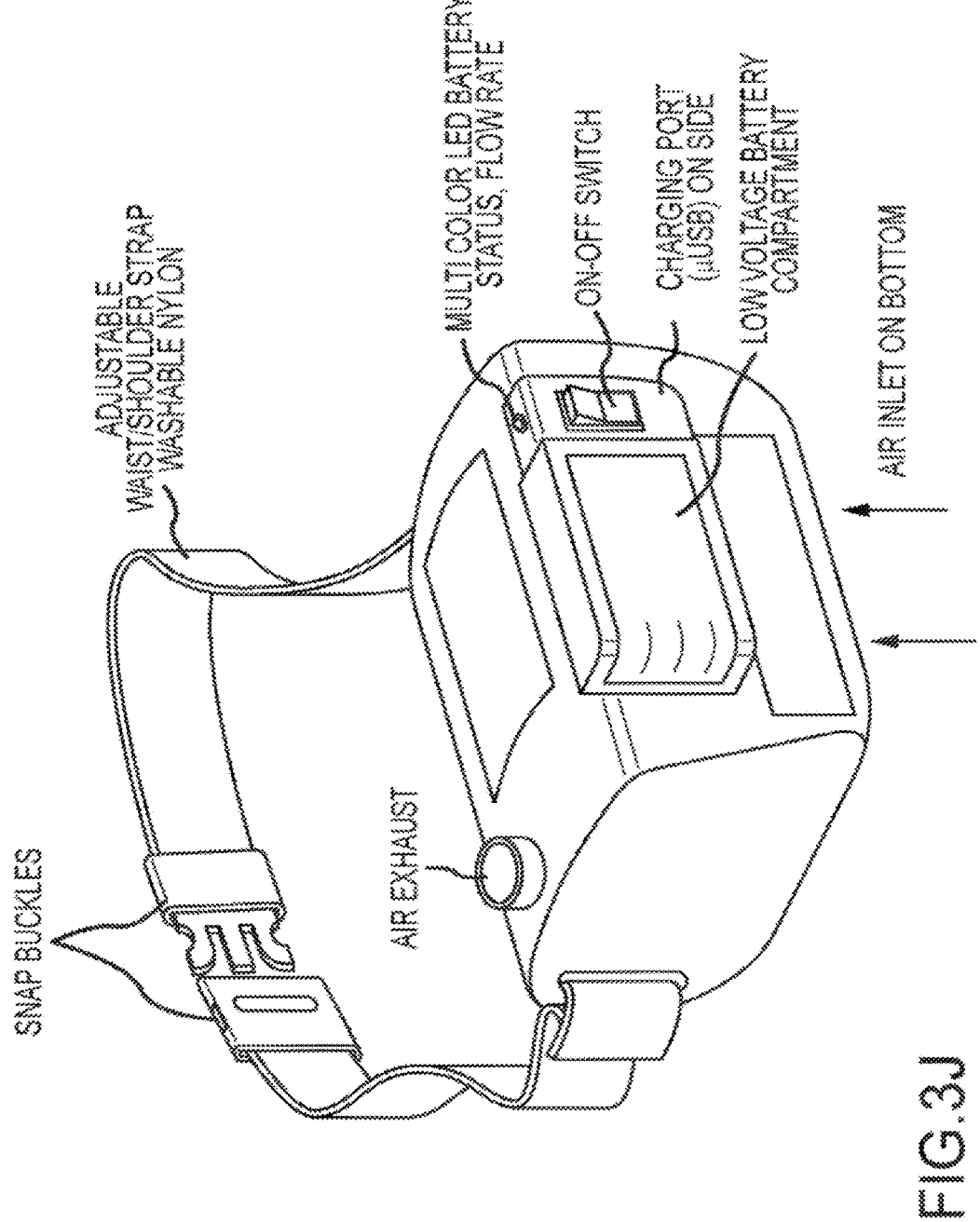
Figure 3K:
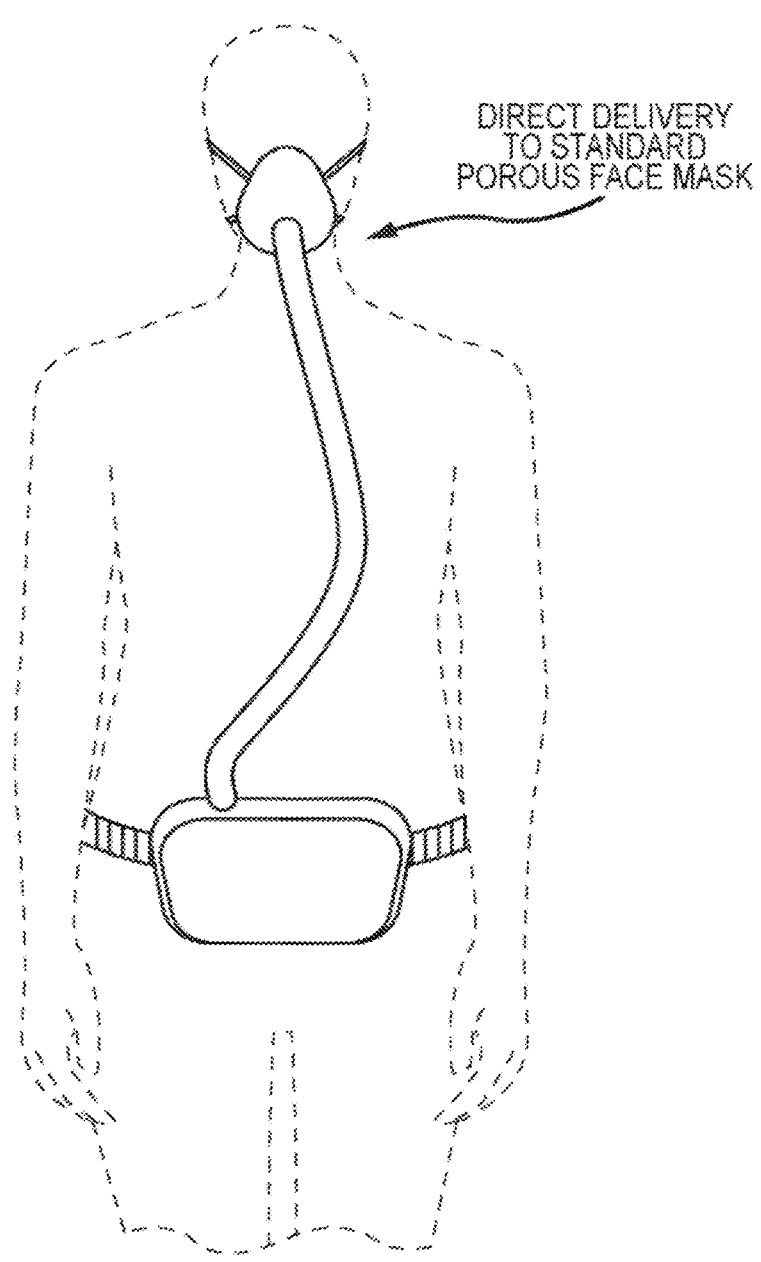
Figure 3L:
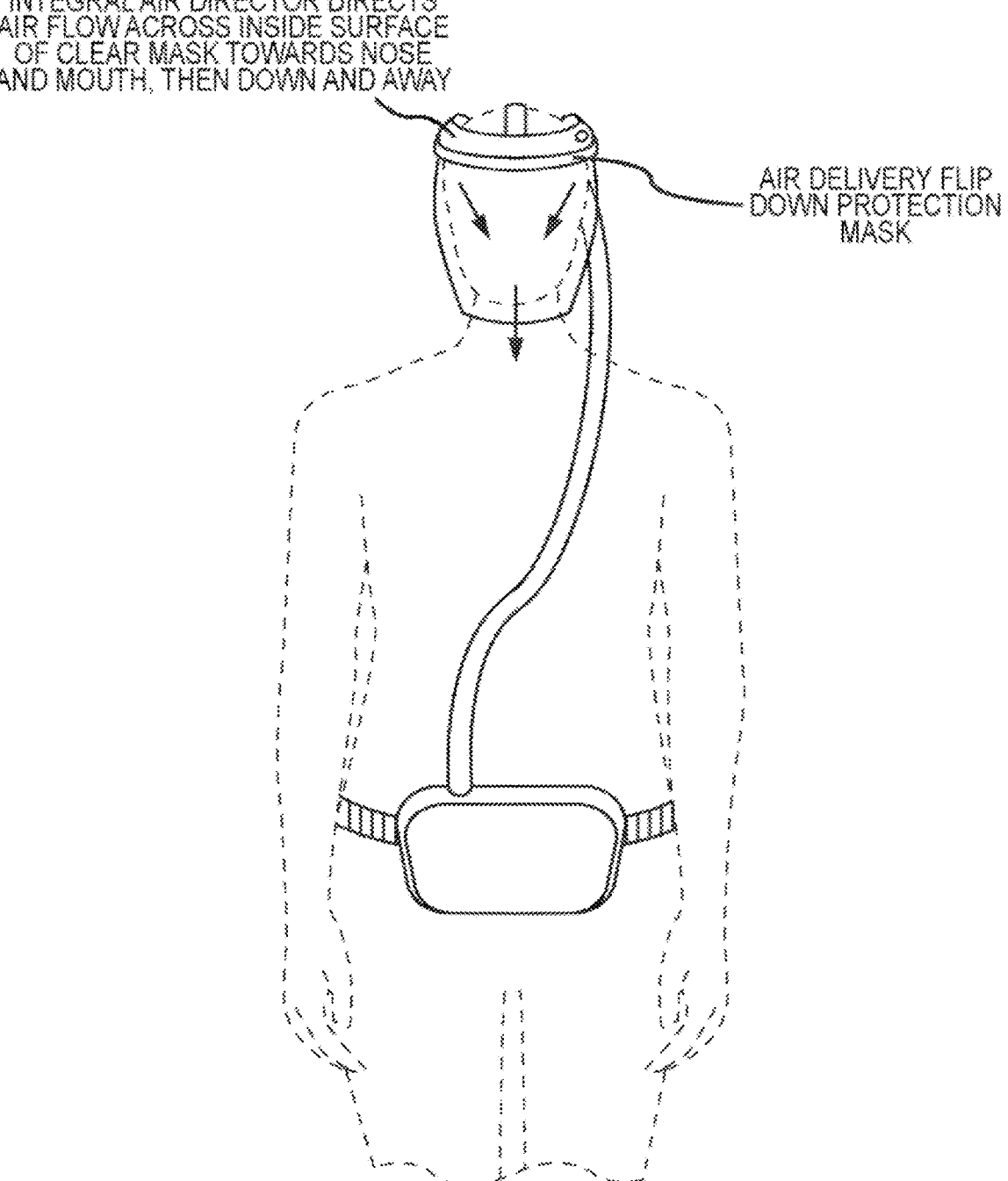

FIG. 1C depicts an example user wearing one possible instantiation of the mask module in accordance with the present invention. It should be noted that various form-factors in this size category are possible, and this representation is not restricted to this exact combination of size and dimensions. Observing FIG. 1C, the dimensions of the package can be observed and envisioned as miniature with respect to many available protective suits or other equipment that provide safe air supplies that are on the market. These instantiations also have the advantage that they are much more comfortable and convenient to work in than "gas mask" style air filtration devices and less intimidating to patients. In one possible instantiation, the overall package size of about 4-6 inches high, 4-6 inches wide, and defining a cupped depth of about 3-5 inches, and thus defining a volume of no more than about 180 cubic inches, is in the very compact size for this level of protection. Additional depictions of mask modules in accordance with the present invention are shown in FIGS. 1I-1J.

3. Filter Module

Figure 5A:
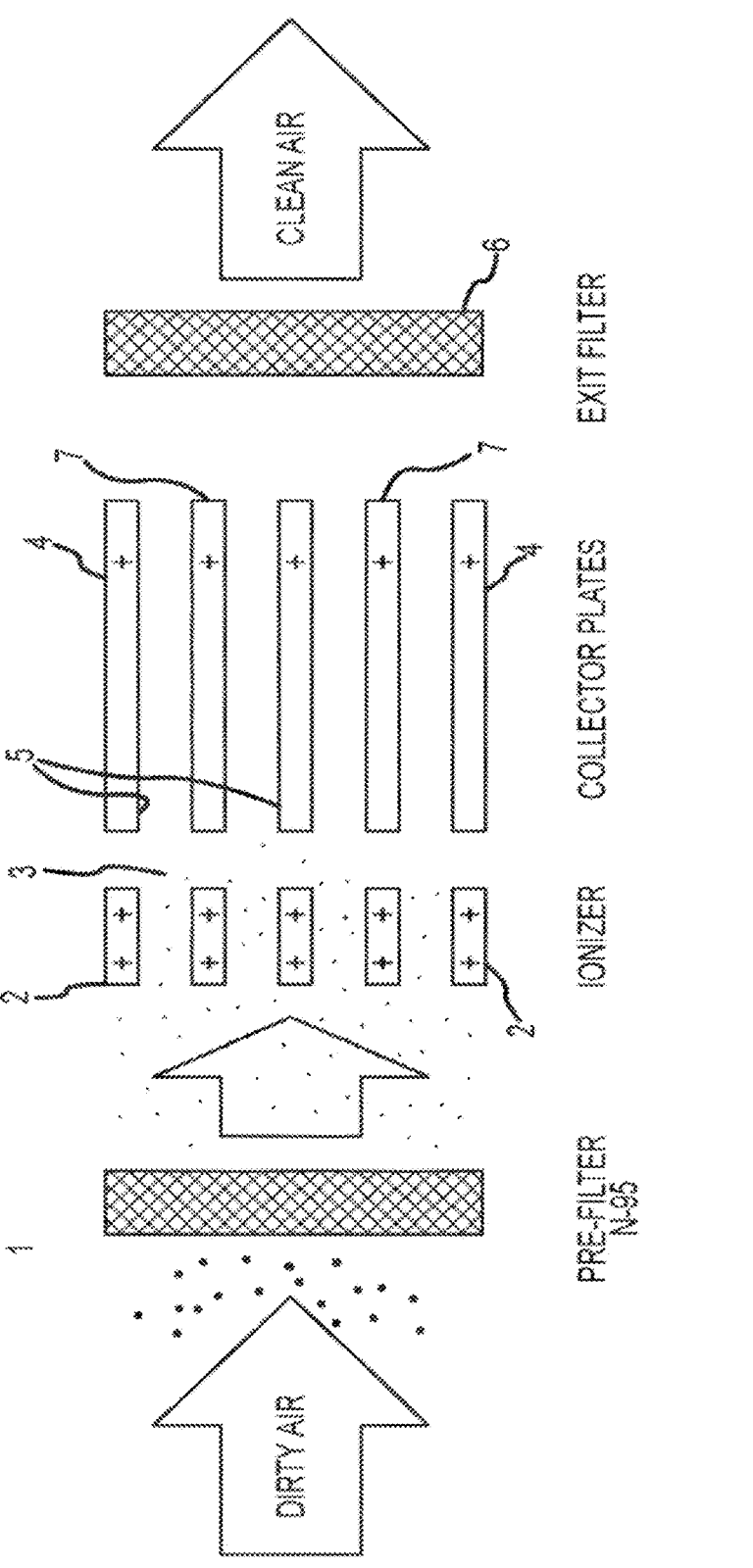

FIGS. 1A and 5A are schematic diagrams applicable to several possible instantiations of the invention and the function of the modules.

Electrostatic filters are already proven to be effective against many types of contaminants, both biological, chemical and physical particles. They are also long-lasting and can be designed to wash and reuse the filter element(s). The problem is that traditional electrostatic filter technology is much too large for portable wearable applications as are described herein. The following components of a suitable filter must all be sufficiently small and energy efficient to work in the invention:

a. Power Supply—Ideally to achieve the desired filtration, a voltage in the 3-10 kV range is required. One instantiation of a power supply that can deliver this required voltage and is preferentially less than 2 cubic inches in size and can be built quickly with commonly available parts is shown in FIGS. 1I-1N.

b. Filter Geometry—A key issue in designing a suitable filter is managing airflow on both a macro and micro level. You need to get the air with the particles of interest to flow predictably next to the charged surfaces of the ionizer (usually positively charged, but not always) to best ionize them and then later pass in a laminar flow next to the oppositely charged surfaces of the collector to trap them. Note that the collector is usually negatively charged but not always, also that in some instantiations the collector could be at ground potential for safety reasons. The voltage difference between the ionizer and collector is what is a key design factor. Air that tumbles tends to prevent the particles in the airflow (in the COVID-19 case these are very small water droplets containing viruses or viruses floating, often with some water molecules on their surface) from properly ionizing and later being collected and may also knock collected particles loose, freeing them, which can defeat the filter. At the same time sufficient airflow volume through the filter is needed to insure that the user has sufficient air to breathe properly and that sufficient positive pressure and/or airflow is maintained to prevent outside air from reaching the nose and mouth of the wearer. The design elements that must be balanced are size, weight, fan capacity, energy usage of the fan(s) driving the air, volume of and flow characteristics of the air plenum(s) and number and arrangement the of chambers and filters through the module, geometry of the charged surfaces of the ionizer and collector, operating voltage, sufficient and complete ionization of the target contaminants, airflow dynamics both macro and micro and the geometries of the module and filter(s) construction that optimize these variables to achieve the desired result.

FIGS. 2E-2F, 3A-3J, 4A-5E, and 6A-6B show the configurations of possible instantiations of an electrostatic filter in accordance with the invention. The geometry of the filter surfaces can be optimized on a macro level to maximize both ionization of target contaminants and available surface area in a small space to maximize smooth airflow. It can be optimized on a micro level by adding scratches or other features in a suitable pattern and/or shape that act to more effectively perform ionization and collection of the contaminant particles. This is very easy to do with many materials (for example aluminum or copper). For example, the COVID-19 virus is relatively large for a virus with an average size of 60-140 nm, which is less than 1 micron. Appropriately sized scratches act like a canyon to particles of the right size. For example, in one preferred instantiation of the invention, a total surface area of about 750 square cm is available. Utilizing 200 grit sanding will produce microscopic furrows in the surface in the 10-50 μm range. Assuming a reasonably uniform distribution of these microscopic grooves, in excess of 1 trillion COVID 19 viruses would only fill those grooves to about half full. The advantage of having a group for the particle to fall in is that it will be electrostatically bonded to the surface at two points rather than a single point, greatly increasing the cohesive force in helping ensure that particles are more attracted to the collector and once attached that no particle escapes. The particles in the grooves are then surrounded on several sides and this works very well to both ionize and then trap the particles in the collector. Note that instantiations of these features can be optimized to work best with the target particle size range and multiple filters that each are optimized for a specific particle size range can be combined. This can make the filtration module much more effective against a particular target contaminant particle, such as COVID-19. Another feature that can be employed is to divide the filter(s) into chambers and or sub-sections that act to moderate the airflow velocity to maximize (or minimize) both the time it takes for a target containment particle to pass through a section of the filter (longer can be better) and areas (more can be better) of the filter(s) that have laminar vs. turbulent airflow. A large-scale example of such a device is a snow fence. It acts to reduce air velocity of the air passing over and through it and thereby collects snowflake particles. Note that this is an example of one type of geometric airflow management feature that can be used on both a macro level and a micro level. In the macro level, the airflow is managed to be both laminar and velocity controlled, to maximize particle fallout. In the micro level it can be used to maximize ionization and collection by getting more surfaces closer to the contaminant particles. The usage of filter or filter chamber shapes, geometries, materials and treatments of those materials that have advantageous characteristics to accomplish this at either the macro or micro level can be incorporated as a feature of the invention. The length of each filter chamber and the materials used to separate each filtration element and/or chamber can also act to manage the air flow characteristics as needed. All of these features can be combined as needed to help achieve the necessary collection of the contaminant particles.

Figure 4A:
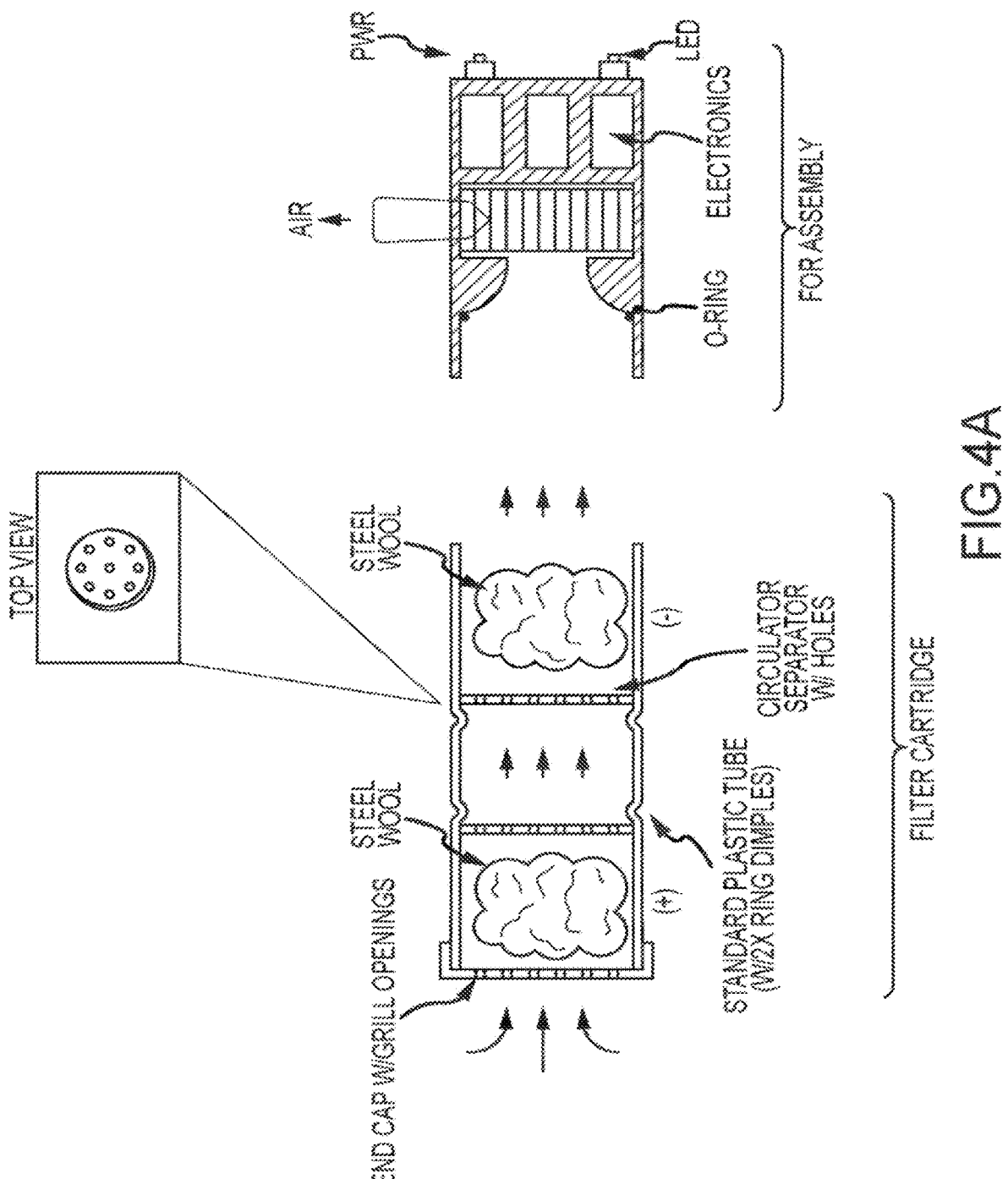
FIGS. 4A-4C illustrate an alternative implementation of a filtered air supply module in accordance with the invention.
Figure 4B:
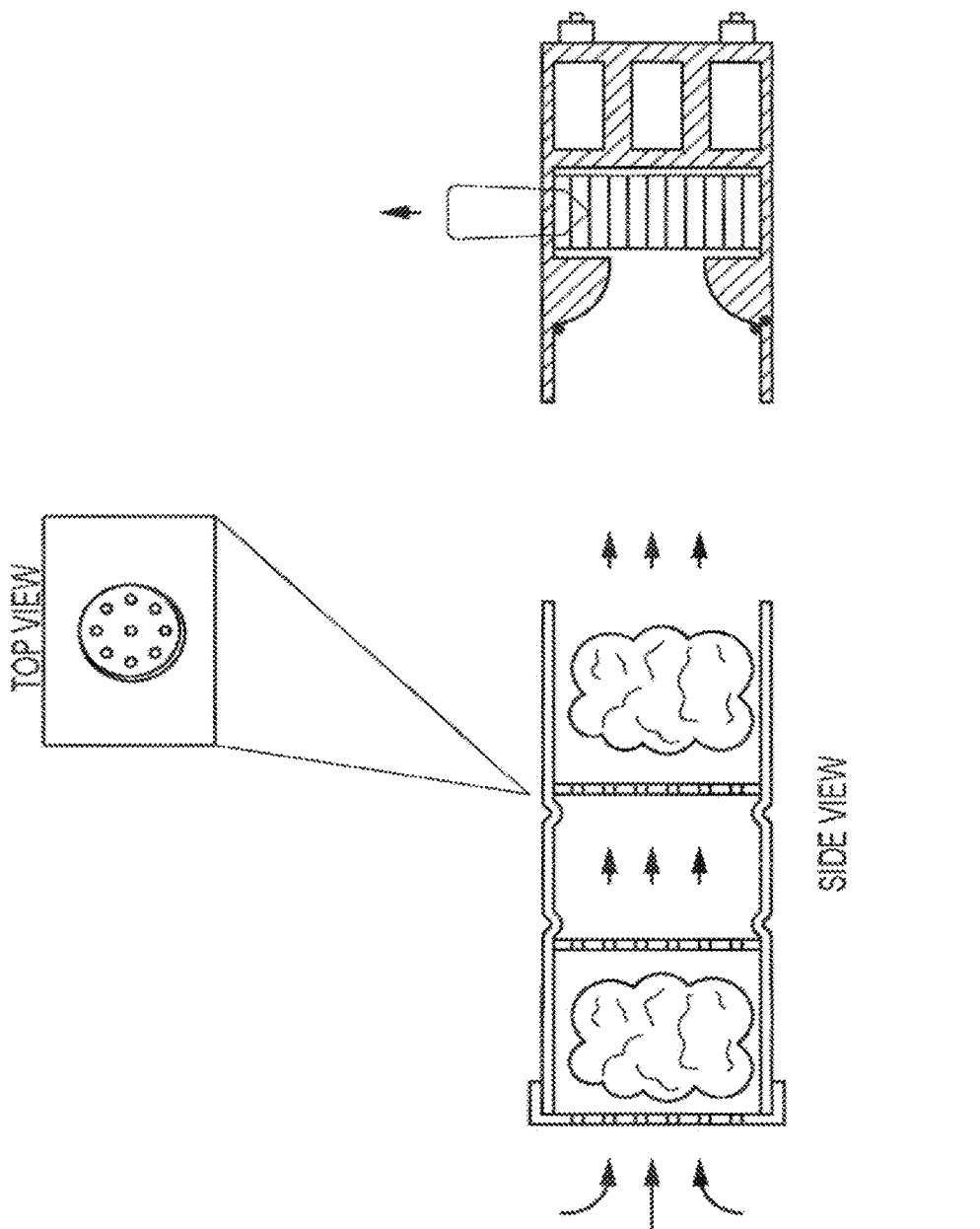
Figure 4C:
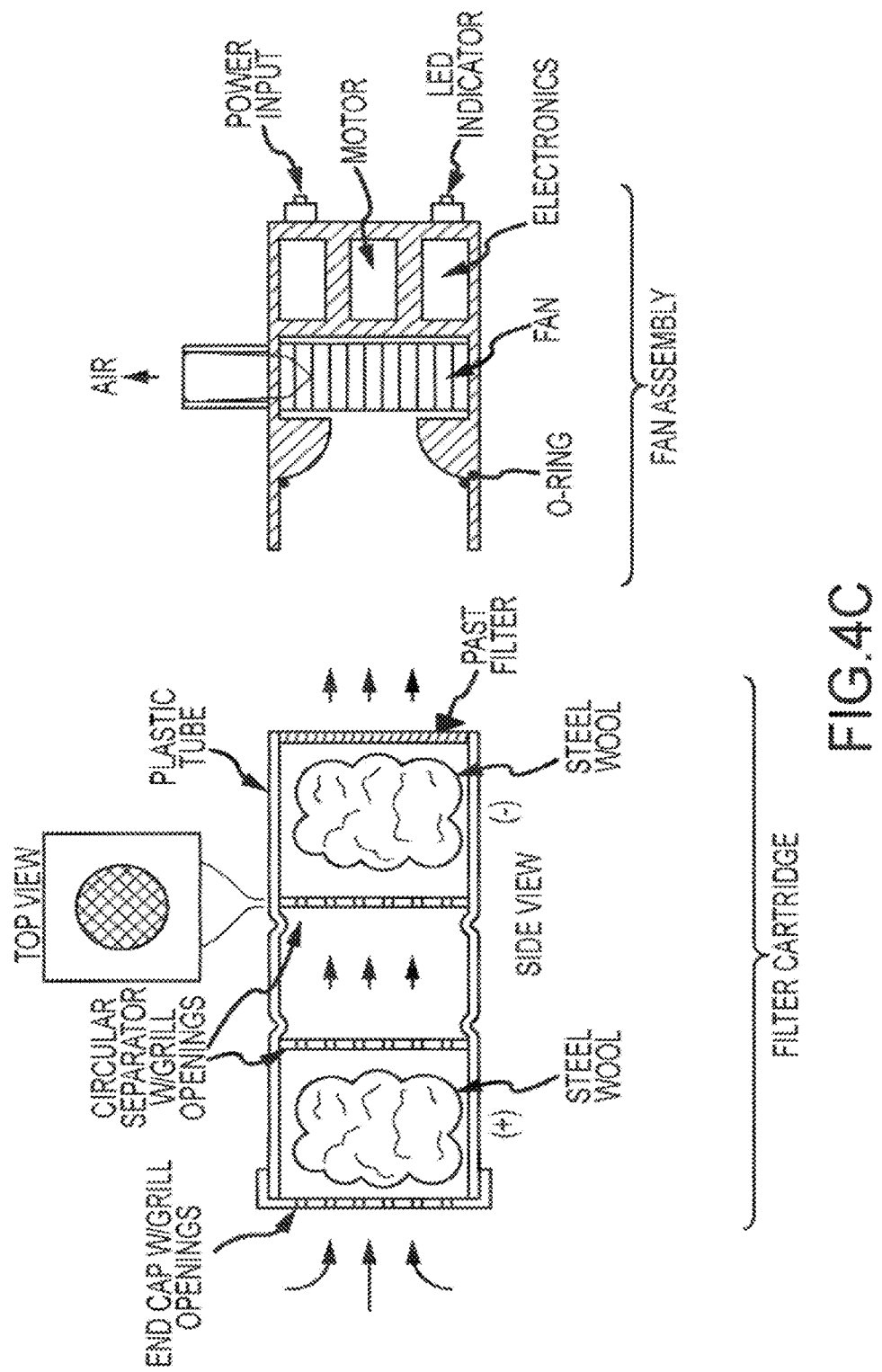

FIGS. 4A-4C depict the configuration of another possible instantiation of the invention. The filter is designed as a set of chambers. Each chamber is filled with stainless steel wool, which forms a spaghetti-style 3D matrix of conductive fibers. The filter can be divided into chambers that act to moderate the airflow velocity to maximize both the time and areas of the filter that have laminar vs. turbulent airflow. The length of each filter chamber and the materials used to separate each chamber can act to manage the air flow characteristics as needed. This helps achieve the necessary ionization and then collection of the contaminant particles. Steel wool could be used as a filtering medium in either the ionizer (+) or collector (−) portion of the electrostatic filter, or in both. One advantage is the readily available and economical nature of steel wool. Additionally, no complex manufacturing processes would be required, rather the manufacturer would simply insert a predetermined volume of steel wool into the filter chamber(s). This would also allow easy servicing and replacement in the field.

In addition to the electrostatic filtering of particulate, chemical and organic compounds, steel could also provide mechanical filtering by collecting debris and particulate as air passes through. In this way, if steel wool were utilized in the ionizing portion of the electrostatic filter, it would serve a dual purpose of both ionizing the incoming stream as well as collecting particulate, thus acting as a pre-filter and ionizer simultaneously.

A cotton pad, or other suitable filtering material or mechanism (for example a fine screen that is washable) could be utilized as a post-filter to any steel wool-based electrostatic filter to prevent small pieces of debris, residual from steel wool manufacturing, from leaving the filter cartridge and entering the other elements of the filtration module and/or its output air.

An additional benefit of steel wool as an electrostatic filtering medium is that it could be easily packed into filter chambers of any geometry, potentially allowing for more ergonomic or compact instantiations of the module.

FIG. 4 depicts the configuration of another possible instantiation of the invention. It describes a filter designed specifically for removing particles of less than 1 micron in diameter, including most common viruses or virus carrying droplets. This filter instantiation can be incorporated into the filtration module described above.

The Filter design includes the following features:

1. Effective filtration of virus molecules without requiring consumables.
2. In other words, it can be cleaned and re-used repeatedly with little or no degradation to the filter.
3. Ease of manufacture. This Invention is designed with common materials found in generic manufacturing processes worldwide.
4. Low cost. The deployment of this is intended to be accomplished on a very short timeline and with minimum costs. Use of common materials and components enables rapid deployment of supply lines necessary for extremely rapid production
5. The invention must be lightweight and compact. It is intended to be worn or carried on the body of the individual. This may be up to many hours at a time.
6. The invention must be reasonably quiet. Excessive noise will interfere with hospital and medical care operations.
7. The invention must be safe to use. Hazardous voltages must be fully contained and insulated from the user in all conditions including wet and volatile gasses, alcohol fumes, etc.
8. The invention must not radiate electrical radiation that would interfere with sensitive hospital and medical equipment or communications devices FIGS. 5A-5E describe the basic operation of an active electrostatic, or so-called electronic air filter.

Dirty air enters and is pre-filtered. Shown in FIG. 5A is an equivalent N-95 filter 12 to remove particles down to as small at 1 micron. This reduces the content of filtration necessary in the electronic section and prevents large particles from entering that could disrupt the operation of the electronic air filtration section. Many other pre-filter combinations are applicable, but all preferably filter all particles and debris that is in excess of approximately 0.1 mm.

The input air passes over the ionizer array 17 which is generally a set of fine wires arranged in the path of the air flow with air guide and charge barrier fins between the ionizer wires. Many combinations are used in industry to accomplish the ionizing stage. Some include arrays of sharp points. In the case of this invention, two novel methods are disclosed, one is the traditional fine wire separated by grounded plates, and the second is the use of fine stainless-steel wool, commonly available and washable. The steel wool is not as good at ionizing the air as the other methods, but the reduced ionization characteristics of the steel wool is compensated for by elevating the ionization potential of the charged steel wool. The advantage of the steel wool is ease of manufacture and immediacy of availability.

After the air has been ionized with a charge potential of about 5000 volts, it exits the Ionization section where the airborne particles 40 are also charged with 5000 Volts charge, or essentially, had a lot of electrons removed. These particles are now seeking electrons to balance out the atoms. They will be attracted to anything with a surplus of electrons. As the air carrying the electrically charged particles approaches one of the negatively charged collector plates 4 the positively charged particles are attracted to the plate and will attach to the plate by "static cling". The plate and the particle are now sharing electrons and the particle is attached electrostatically to the plate.

Simultaneously, particles with trajectories that would send them away from the negatively charged plate will encounter positively charged plates 45 with a charge field of even more positive charge than they have, and the particles in these cases are repelled away from those more positively charged plates 45. The particles are directed away from these highly positive charged plates 45 and towards the negatively charged collector plates 4 which they are attracted to and then electrostatically attached to. The air is physically pushed through the assembly and exits via an exit filter 44 which removes any detritus located inside the filter assembly. The exit filter 44 can also be an activated charcoal filter that can help reduce sub-micron aerosols and some gasses. In this invention, the exit filter is a coarse filter only to remove large particles that may be present from manufacturing or left behind from cleaning and handling operations during use.

This is a generally accepted method of electrostatically removing particles from an air stream, and many patents reference this technology in a wide variety of applications. This patent describes how this technology is applied to the specific purpose of removing particles from 0.5 micron down to 0.01 micron from the air stream. In the past, electronic air filters were intended to remove relatively large particles, dust, pollen, etc. from the air stream for improving the air quality from a physical and sensory standpoint. Residential, commercial and industrial applications abound. And these electronic air filters do in fact remove a significant percentage of sub-micron size particles. But they are big, expensive bulky and generally not portable. In addition, existing designs are not specifically intended for removal of virus size particles as the primary function, they are general purpose. The invention discloses unique methods and apparatus that can be used to target specific sizes and types of contaminate particles and combine them as needed to achieve the desired filtration result in the form-factor(s) required with portability. It should be noted that the control electronics for the filtration module can be designed to shut down the fan before powering off the power to the electrostatic filter(s). Each electrostatic filter will retain a static charge that would tend to prevent trapped particles from floating free. Upon restart, the control electronics can apply power to the electrostatic filter before powering up the fan(s), again to minimize the chances of trapped particles being freed. Also, electrons sharing results in collected particles tending to stay attached to the collector through on/off cycles.

Another way of dealing with collected contaminant particles is to add a self-cleaning cycle, which is compatible with the other methods described earlier of ensuring collected contaminant particles do not escape the filtration module. When the power is shut off to the unit, a self-cleaning cycle can be initiated that connects the battery to the collector plate electronically. This current can be left on for a predetermined time or could be shut off after plate reaches a temperature adequate to kill all viruses.

The power requirement is not great. In this example shown in FIG. 8 the heating of the metal strip is estimated to require 288 W for a minimum of one half second. Leaving the heat on for a minimum of four seconds is more than sufficient to kill any viruses. This period of time represents a load of 96 amp seconds. Most batteries are rated in amp hours, at the rated voltage of the battery pack. In this case, we are applying current from one of the many batteries discussed above. Of those, one of the smallest is a cell phone battery. These are generally in the 5000 ma hour range, and this would be at the lower end of the off-the-shelf consumer grade LiOn batteries in the marketplace now. The 5000 ma (5A) hour battery in the example thus has the equivalent of 5 A for 3600 seconds (one hour). Dividing the 96 amp seconds by the amps results in a ratio of 19.2. Dividing the 3600 by that, 19.2 results in 187.5, the number of times that a four second burst could be performed on a fully charged cell phone battery. It is less than 1% of the battery's capacity to perform the cleaning cycle.

This feature can easily be added to guarantee that the trapped viruses are destroyed each time the unit is shut down. An electronic battery monitor would warn the user when the battery capacity was getting down to a point that might endanger to clean cycle, prompting the user to replace the battery or find plug-in power.

Figure 8:
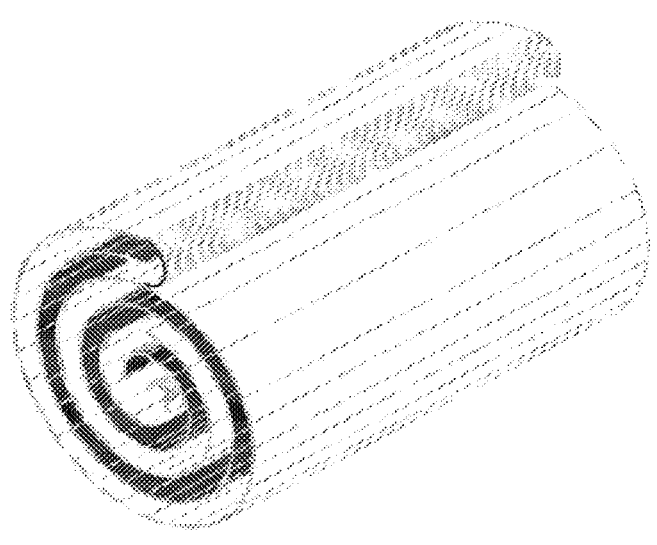
FIG. 8 shows a method of fabricating the collector plate of the filter section in accordance with the present invention.

FIG. 8 shows a method of fabricating the collector plate of the filter section such that a path resistance of 0.5 ohm is achieved. Other resistances can be selected simply by how the material is subdivided. The spacings on the intercut slits can be made very small so as not to significantly interrupt the laminar flow of air over the surface when in operation.
1. Collector Plate Design.

Figure 5B:
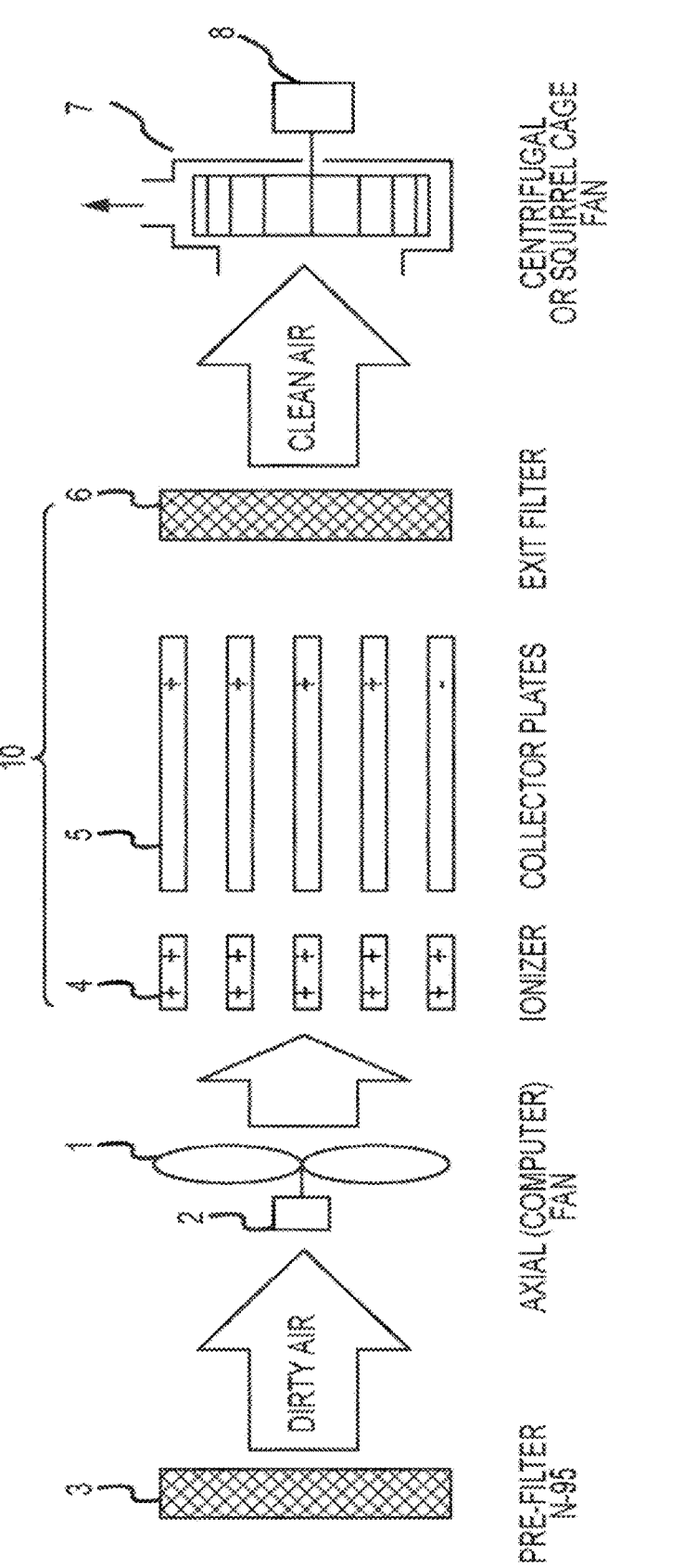

FIG. 5B shows how air is moved through the filter assembly 15. Air can be pushed through the filter assembly 15 with a small and efficient axial fan 13 such as is found commonly in the computer and electronics industry. The motors are often a convenient 12 VDC, and the efficiencies have been pushed to the maximum by sheer volume of trial and error and good design. Billions are produced each year. This fan type is quite well suited for the application described in this invention. It satisfies many of the requirements. The fan in this invention employs a central motor 18 that is cooled by the incoming air and has very high reliability associated with the design. This is an off-the-shelf solution nearly ideal for the application in this invention. However, these fans are limited in how much pressure they can generate. In general use of this invention, there is little restriction to the flow of air, so these fans will work for many applications. However, in some variations of how this filter is utilized, there may be more restriction, e.g., back pressure, that the fan must overcome. FIG. 5B also shows an exit side fan 46 pulling the air through the filter assembly 15. This fan can be of a centrifugal design or a so-called squirrel cage design. Both types are better at delivering air against some resistance, especially the centrifugal design. The squirrel cage design is often the quietest. Thus, depending on the application requirements for this filter, a fan type can be selected to meet those requirements. A combination of fans can also be employed (as shown in FIG. 5B) to achieve the desired pressure and flow rates for multiple application requirements.

Traditional electronic air filter ionizer and collectors were and are comprised of multiple flat plates separated with insulators made of plastic, glass phenolic and other dielectric materials. The spacing between those plates must be maintained carefully. If the plates are too far apart, then some particles can slip between the plates on the journey through. If the plates are too close together, the electrical charge difference between them may cause an arc to form and discharge the plates, thus releasing captive particles. Thus, the distance must be kept reasonably accurate between differently charged plates and conductors.

The traditional manufacturing process is probably too complex to apply to the rapid deployment requirement of this invention. A simpler method of building the plate assembly is described in FIGS. 5C-5D. Shown in these figures is a spiral arrangement instead of the traditional multiple flat plate method. The intent of this design is to provide a means of manufacturing the plate assembly so it will fit in a circular (tube) housing, be lightweight, of commonly available materials and easy to assemble.

FIG. 5C shows an end view of the spiral configuration of the collector plate. Component 300 is the negatively charged "collector plate" 301 and the separating plate 302 shown is the high voltage repeller plate that pushes the charged particles towards the collector plate 301 as they progress through the space between the two plates carried by the air entering one end and exiting the opposite end. The length of the accumulator plate is determined by the flow rate expected to be necessary for the application. A plate length of 100 mm is a preferred instantiation for this embodiment, but other lengths are easily adapted depending on differing needs. In one preferred instantiation of this invention, a total diameter of the collector assembly can be less than 50 mm.

Figure 5D:
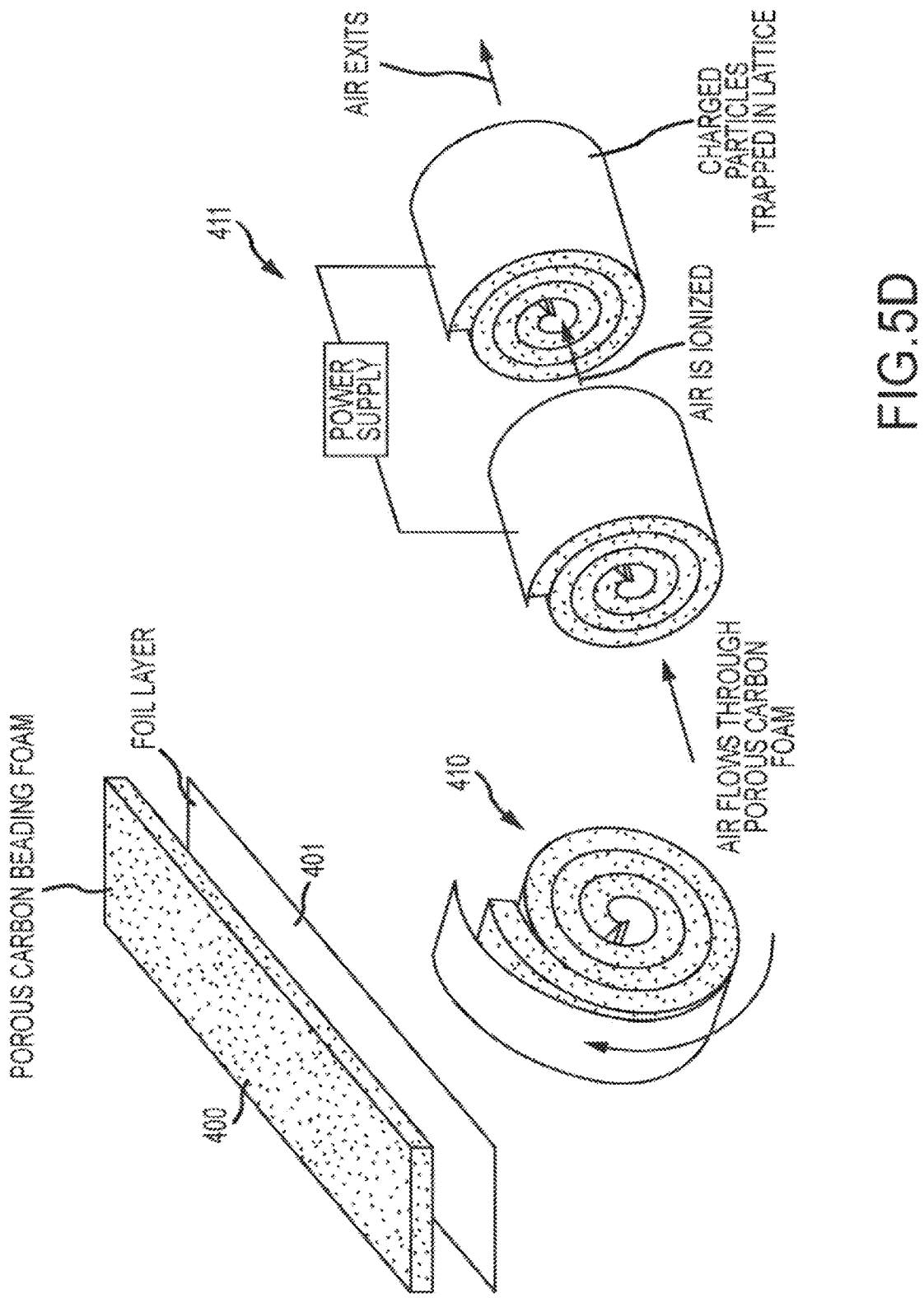

FIG. 5D shows an alternative arrangement of the same spiral concept. It utilizes a very porous carbon impregnated filter foam 400 being cut and laid flat along the surface of the metallic sheet 401 used to construct a plate. This is rolled up into a spiral filter and electrode assembly 410. In this instantiation, there is not the possibility to have alternating high voltage plates (large differentials in voltage) because the carbon impregnated foam is slightly conductive. Thus, the ability to have a repeller plate between layers of the collector plates is negated. However, this design can be used as part of the ionizer and is an option of choice where the finished assembly air filter will be exposed to extremely heavy shock loads and rough use. This may be applicable to wearers such as firemen and construction trades. With reduced efficiency, the units will likely be larger, but that is an acceptable trade-off considering the application will likely involve larger and physically more active wearers. An additional advantage of the sandwiched plate/foam variant is the lack of need for an input filter. The filter operation is accomplished via the foam itself.

Figure 5E:
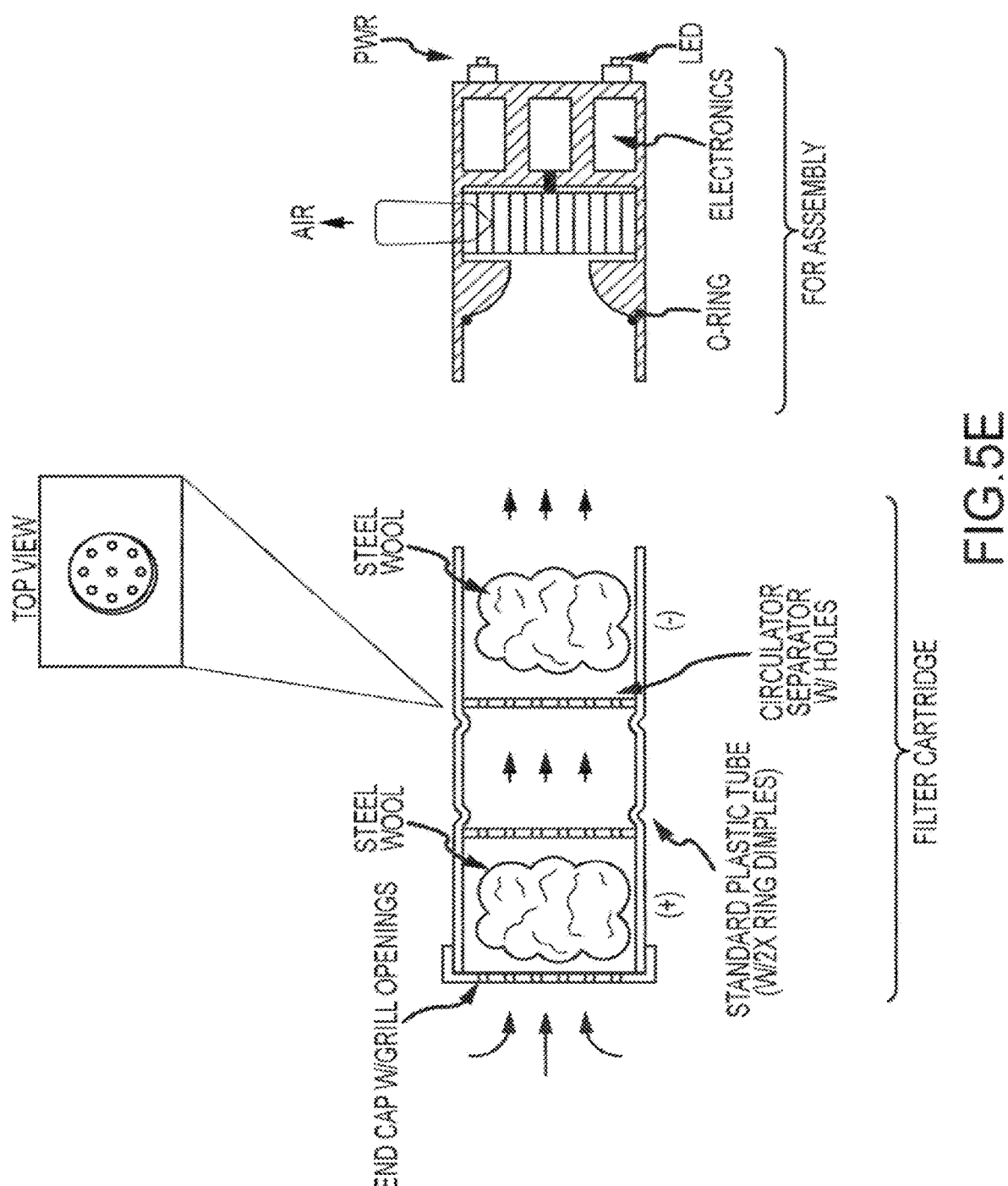

FIG. 5E describes another variant of plate construction where both the ionizer and the collector plates consist of stainless steel wool. Due to localized turbulence of the air as it travels through the steel wool, any particles that are attracted to and attached to the metal of the collector steel wool can be dislodged by chaotic velocities of the air. For this filter type to be effective, the cross-sectional area must be increased significantly for the same volume of air as is applicable in the wire and plate method. This increasing of the area causes the air motion through the filter to be proportionately slowed down. In some manufacturing options, this scheme may be ideal since space will not be of as much concern, such as the filter is included in a backpack, or a belt attached location on the wearer. In these configurations, the advantage of high durability, ease of cleaning, and low-cost rapid manufacturing is likely to be highly desirable.

Figure 5F:
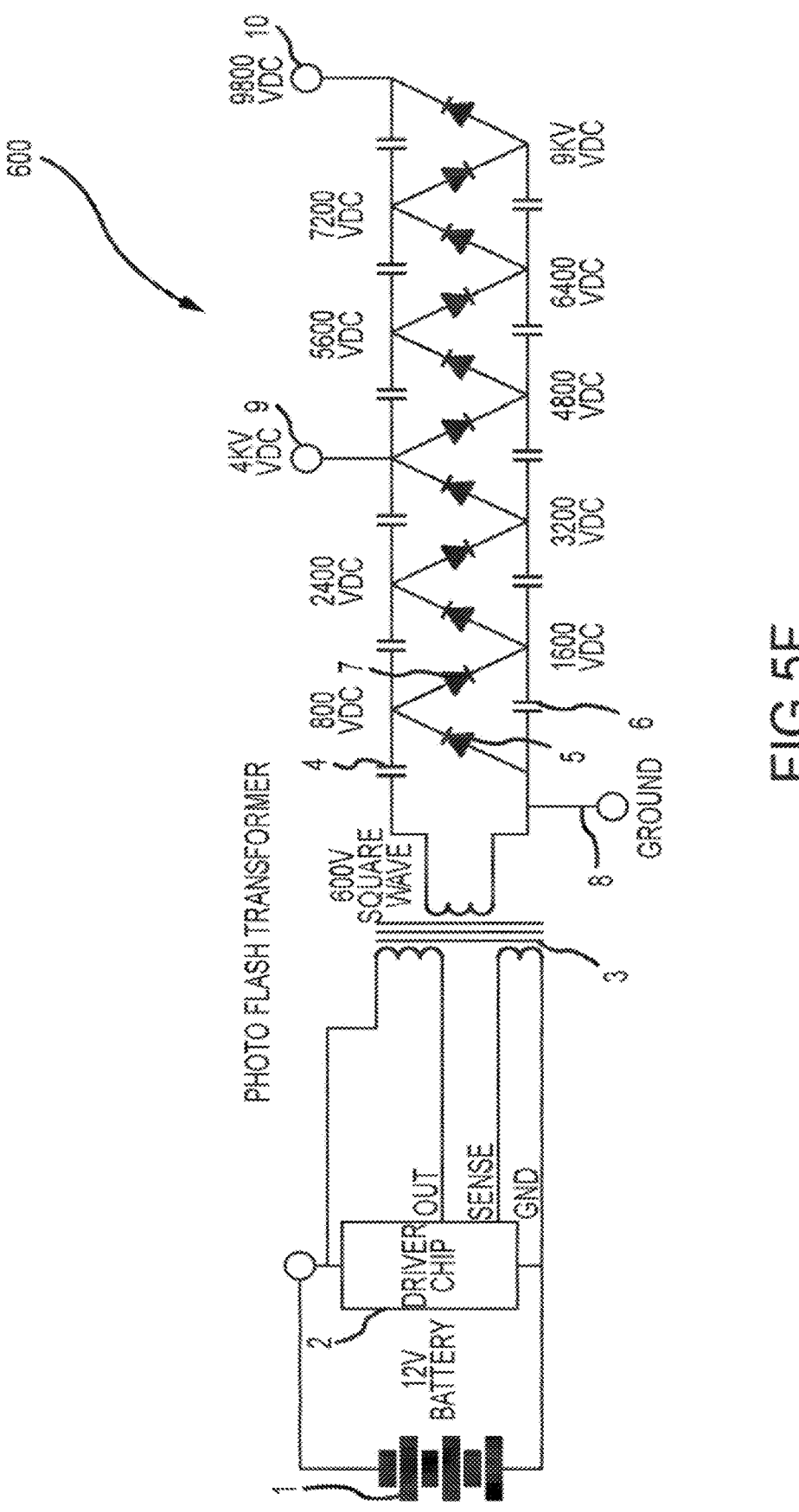

FIG. 5F describes a possible instantiation of a basic power supply circuit associated with this invention. It is comprised of rapidly and easily obtained components. This will allow easier rapid production in the quantities necessary. The battery 14 is connected to a modern switching mode transformer driver chip 19 commonly found in portable electronic device chargers, and thus is commercially available in large numbers and at a low cost. The driver chip sends 12 V switching in a square wave at high frequencies to the transformer 3 which is a photoflash transformer. These are commercially available in large numbers also. The advantage of the photoflash transformer is the output is generally about 800 V AC. The electrostatic filter assembly needs ground, about 4000 VDC and 7 to 9,000 VDC for the repeller plate. This power supply 600 design utilizes a voltage multiplier to step up the 800 V AC transformer 3 output to the desired voltages.

During the negative half cycle of the transformer 3 output, diode 43 is forward biased and conducts charging up the pump capacitor, 42 to the peak value of the input voltage, (800). Because there is no return path for pump capacitor 42 to discharge into, it remains fully charged acting as a storage device in series with the voltage supply. At the same time, diode 47 conducts via diode 43 charging up pump capacitor 42. During the positive half cycle, diode 43 is reverse biased blocking the discharging of pump capacitor 42while diode 47 is forward biased charging up capacitor 42. But because there is a voltage across pump capacitor 42 already equal to the peak input voltage, capacitor 6 charges to twice the peak voltage value of the input signal. On each consecutive cycle of the transformer 3 output switching, the voltage increases 800 Volts along the line of multiplier diode/capacitor pairs. At the 4 KV tap 48 the original 800 V has been rectified and multiplied 5 times. At the 8,800 Volt tap 16 the original 800 Volt AC output of the transformer 3 has been multiplied 11 times. Selection of optimal voltages for various application can be made in 800 Volt increments.

The use of modern ceramic capacitors allows this design to be very compact and robust. Built in current monitoring in the modern switching mode transformer driver chip 19 allows for monitoring for abnormal conditions and rapid shut down of the circuit in the event of an abnormal condition. Conditions such as excessive current (electrical fault) or varying current over time, (possible moisture exposure) or instantaneous peak currents that might indicate the filter is getting loaded up enough that sparks are occurring occasionally.

Due to the small size and high efficiency of this power supply design, it can be encapsulated in epoxy or silicone to improve durability and safety.

Figure 6A:
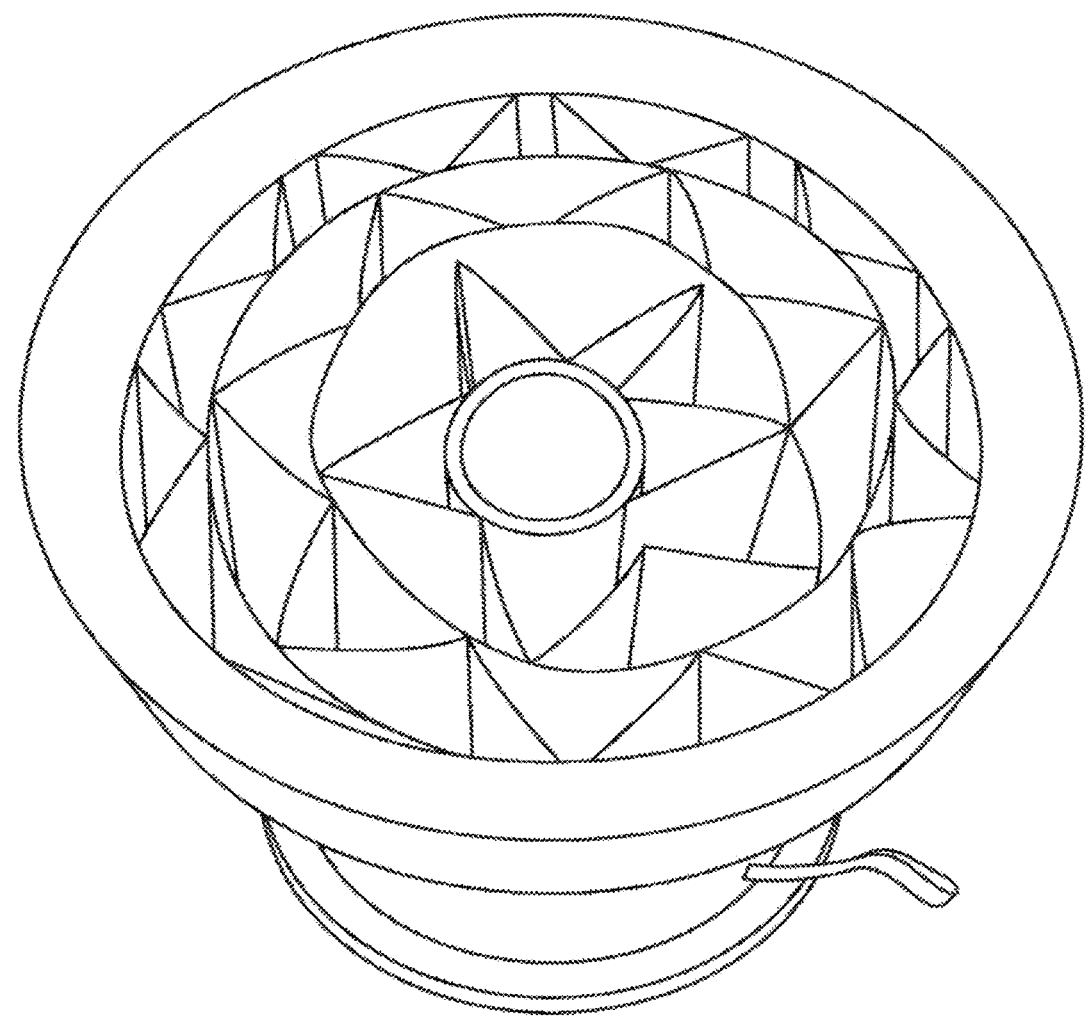
FIGS. 6A-6B are photographs of an electrostatic filter system in accordance with the invention.
Figure 6B:
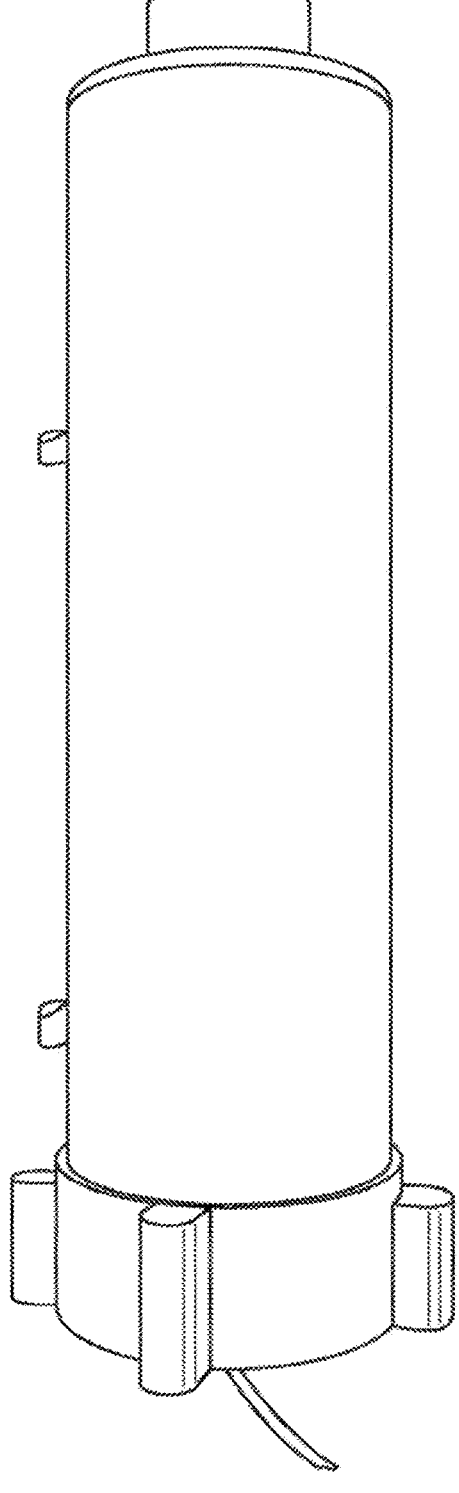

FIGS. 6A-6B are photographs showing an electrostatic filter module in accordance with one instantiation of the invention.

Figure 7:
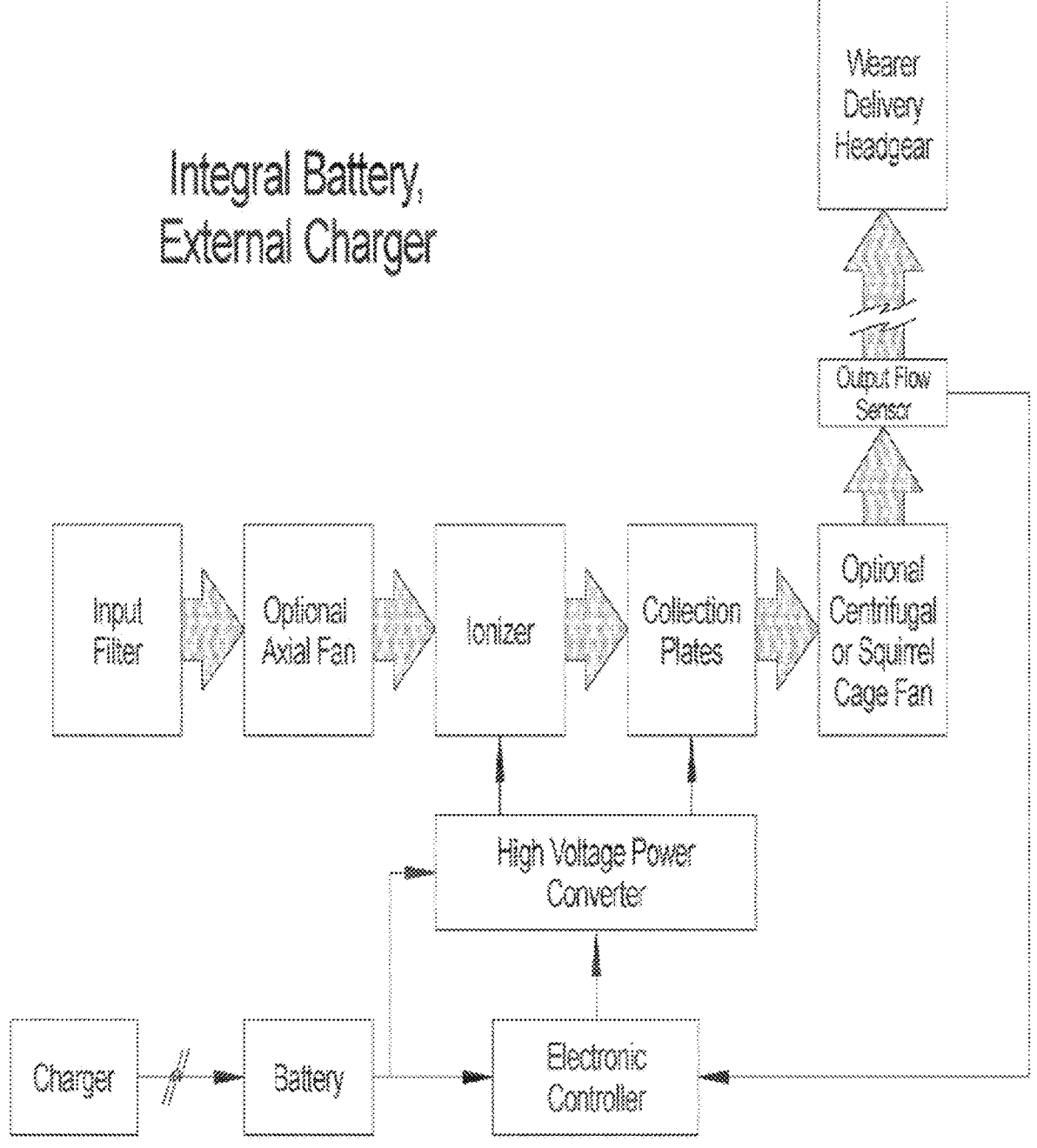
FIGS. 7-7A show a system with integrated and external energy sources in accordance with the present invention.
Figure 7A:
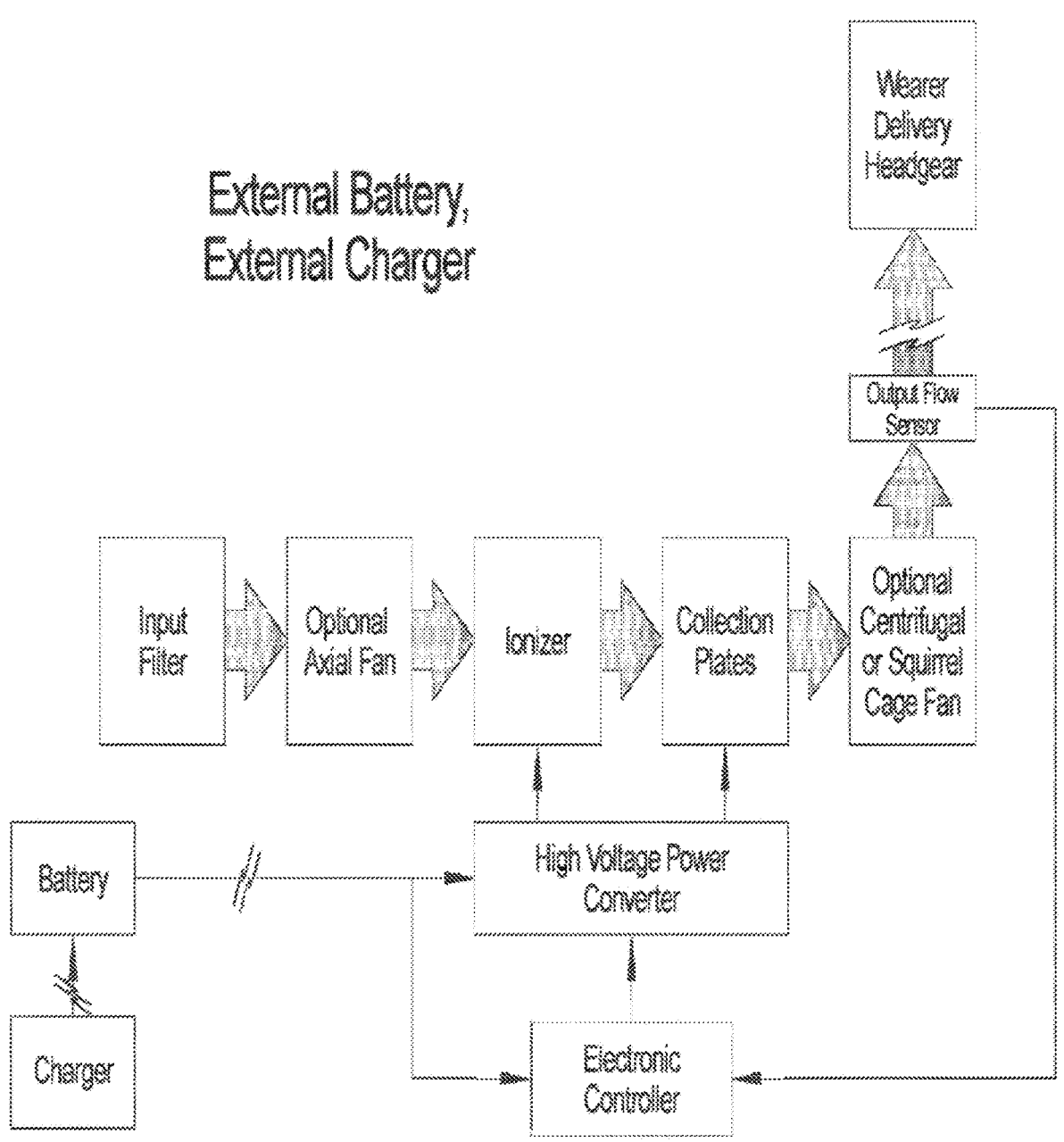

FIGS. 7-7B are schematics showing optional implementations of a system in accordance with the present invention with an integral and an external battery.

Figure 12A:
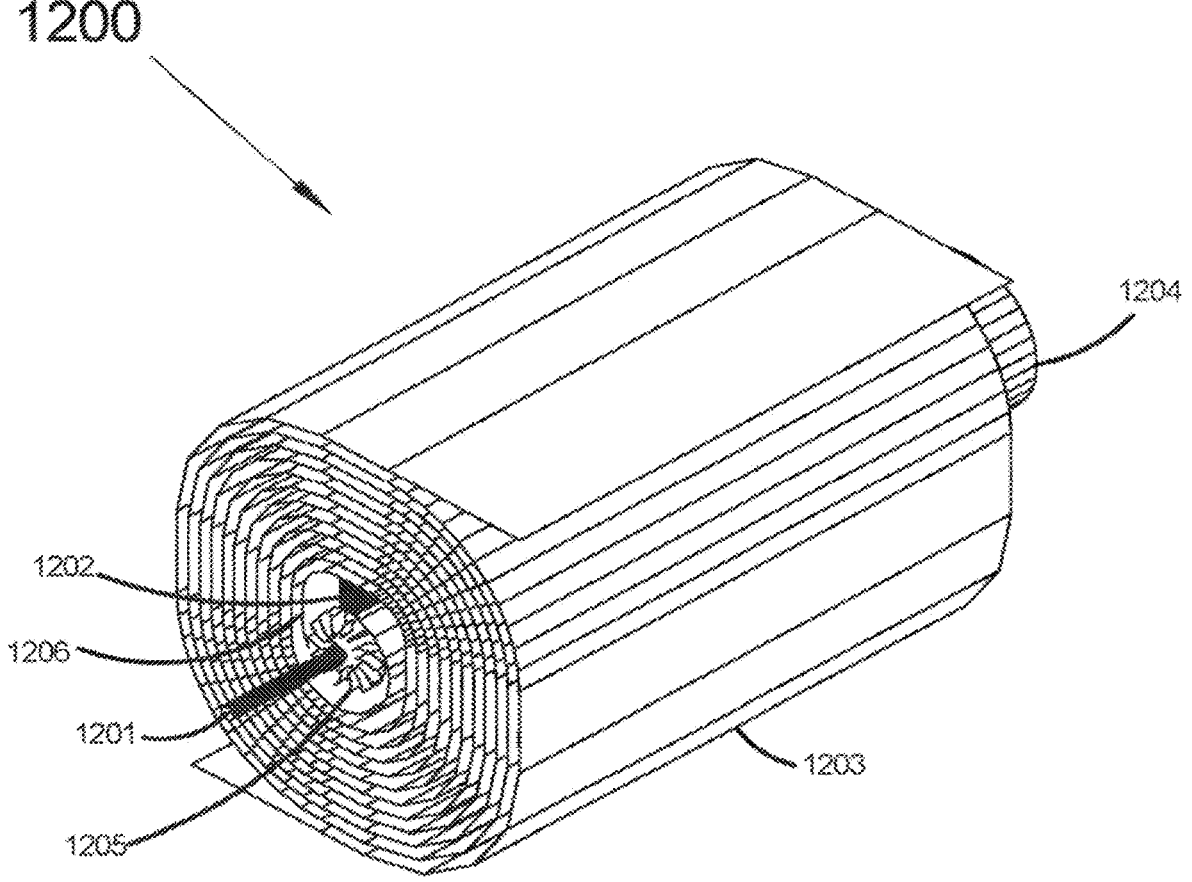
FIGS. 12A-12G show thermal decontamination systems in accordance with the present invention.
Figure 12B:
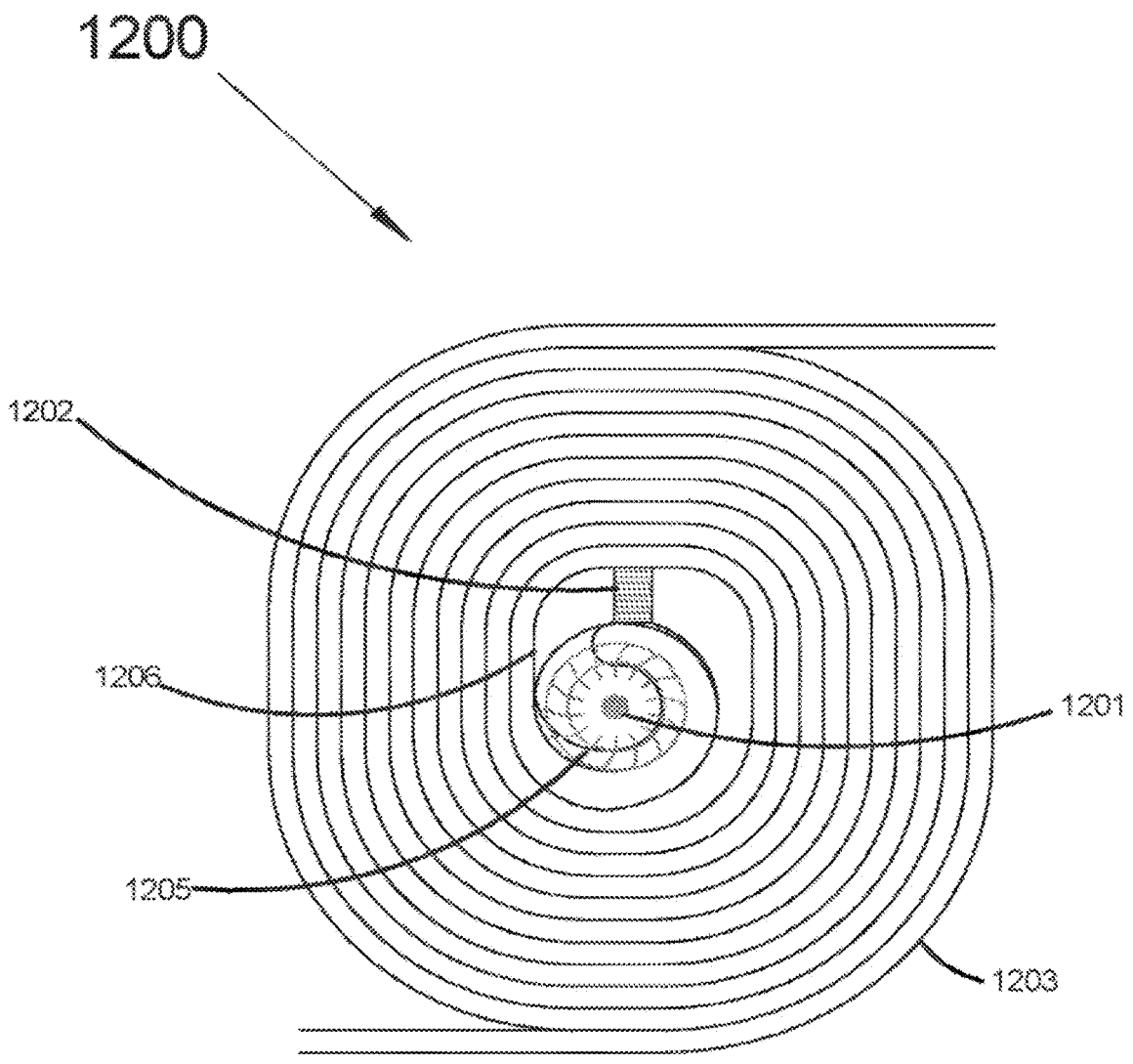
Figure 12C:
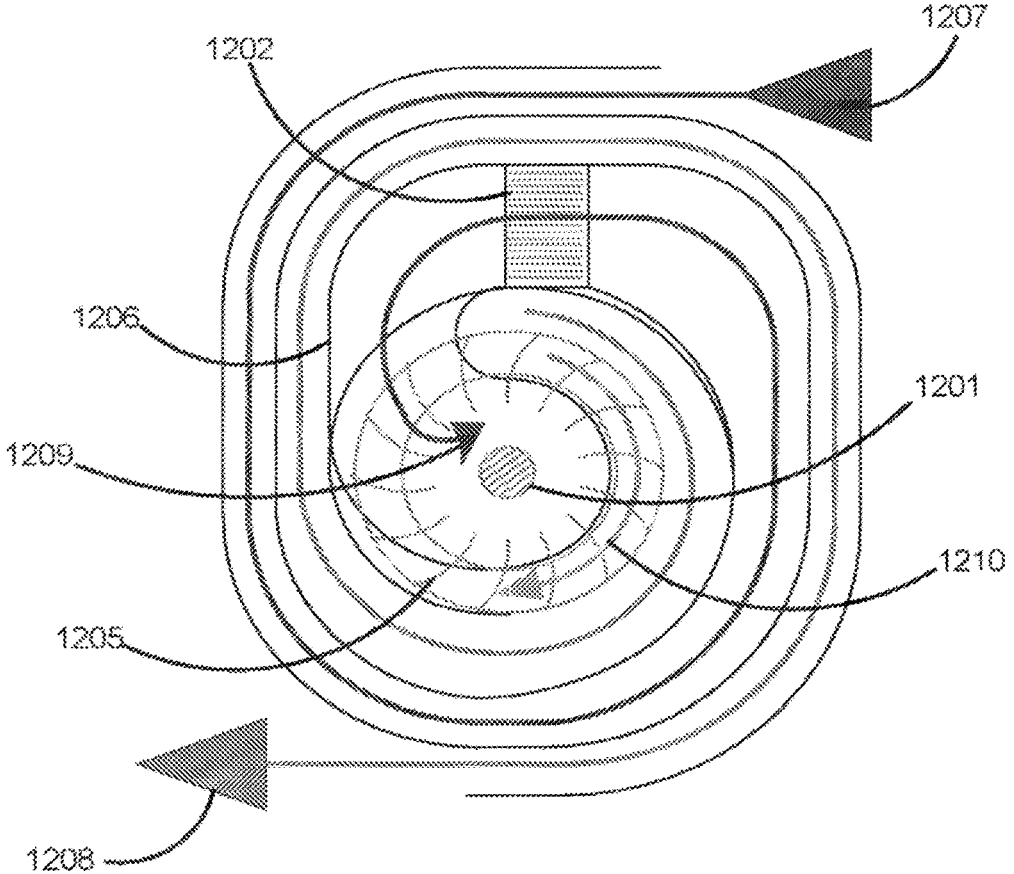
Figure 12D:
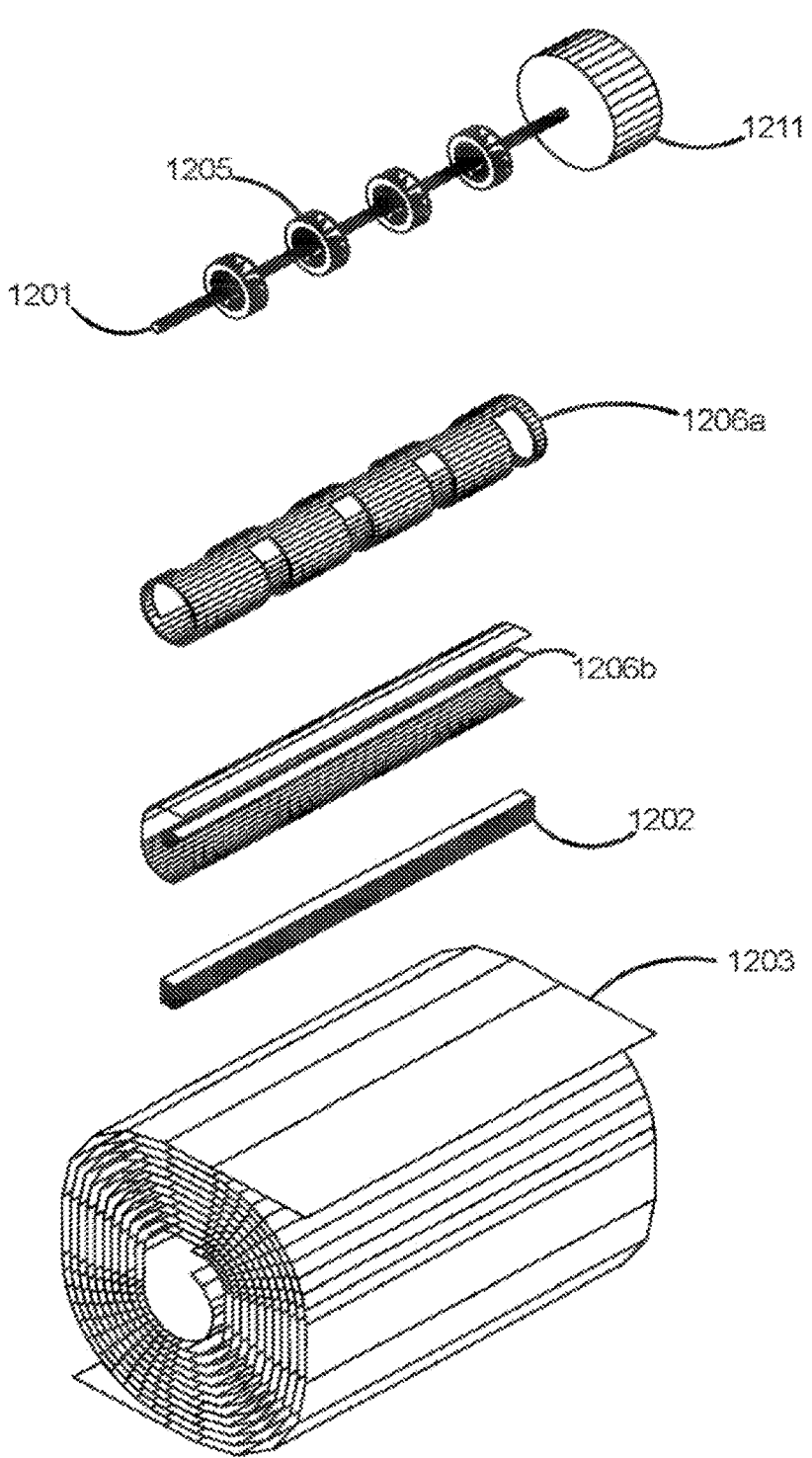
Figure 12E:
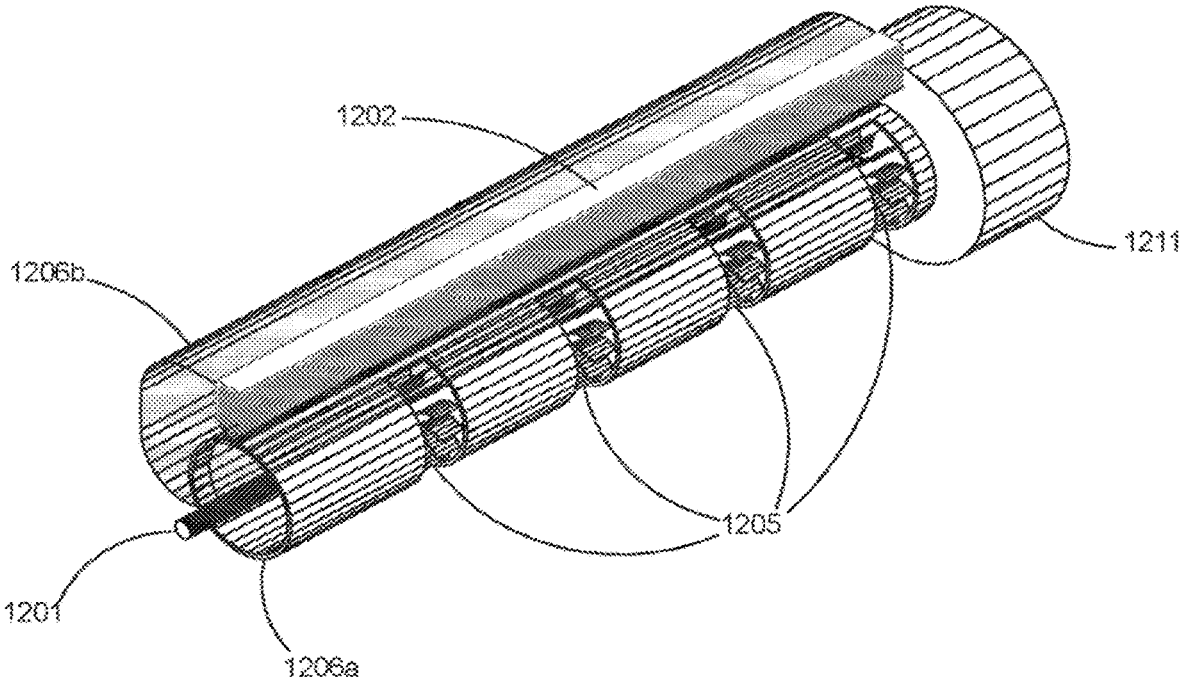
Figure 12F:
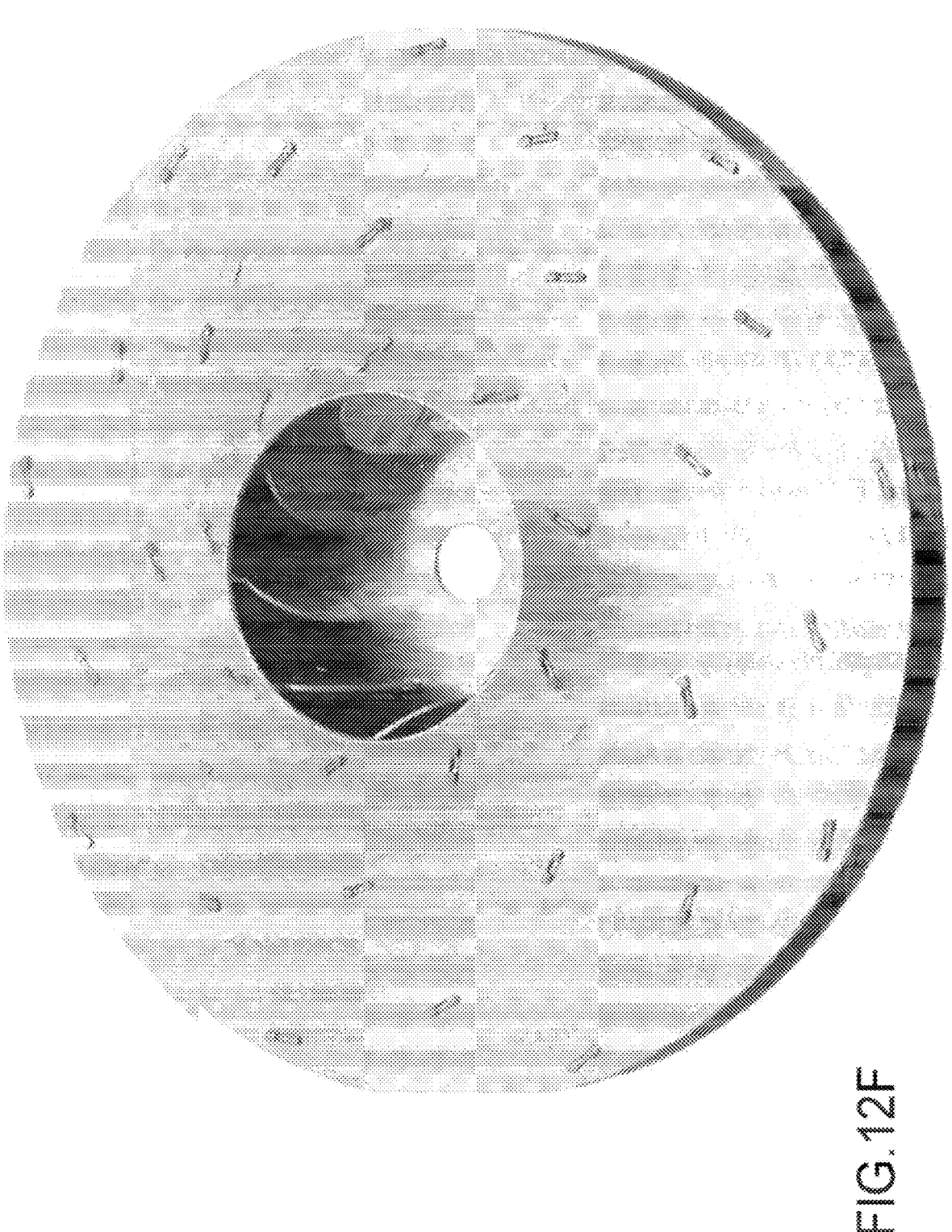
Figure 12G:
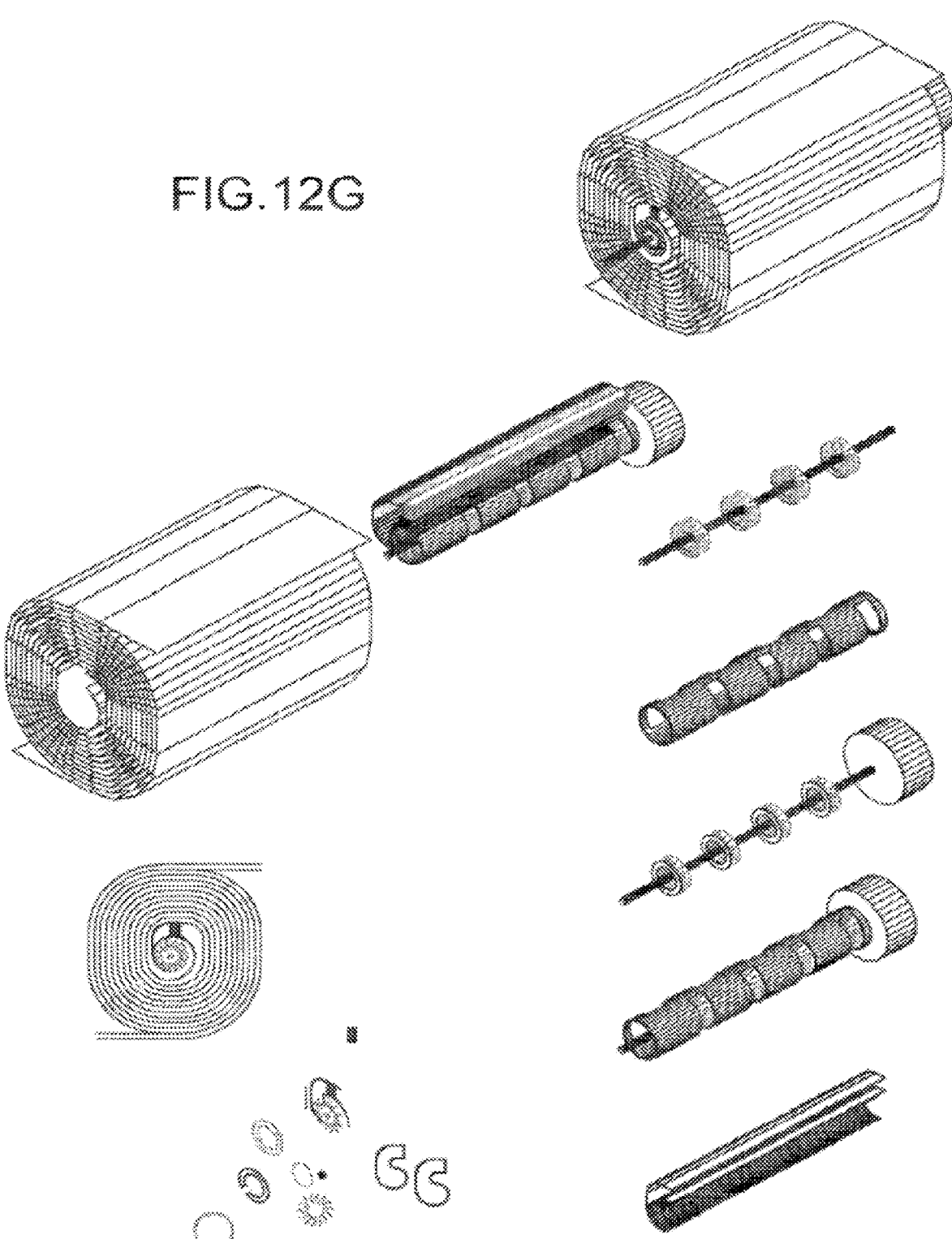
Figure 13A:
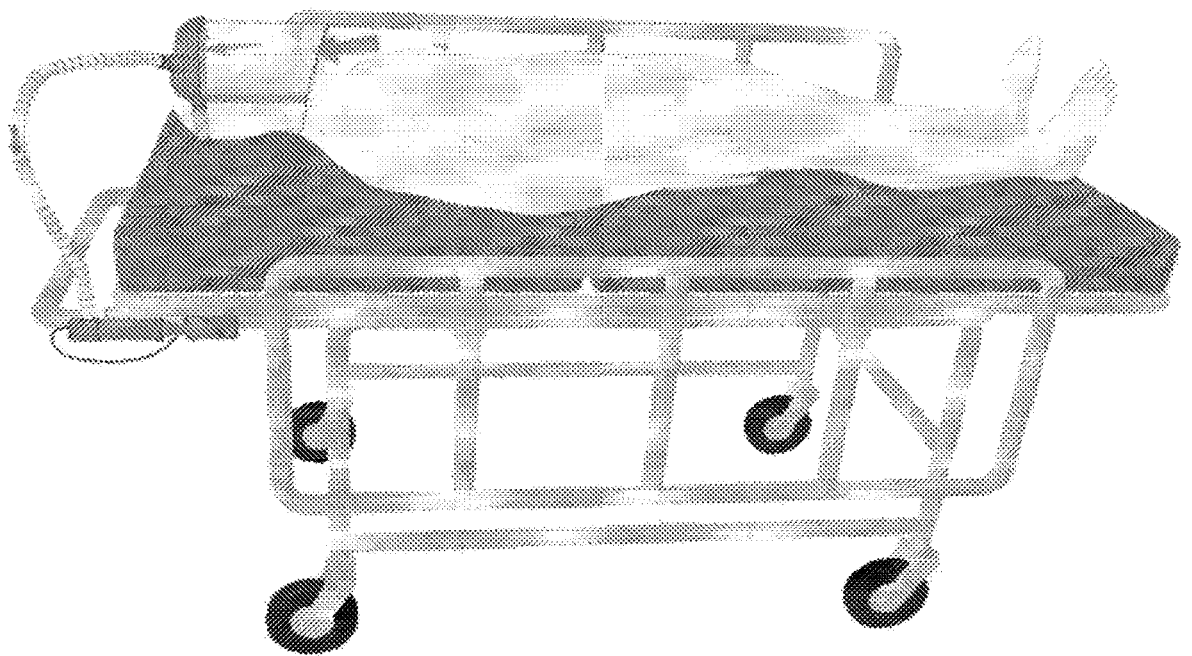
FIGS. 13A-13D show various configurations of an exhale gurney filter system in accordance with the present invention.
Figure 13B:
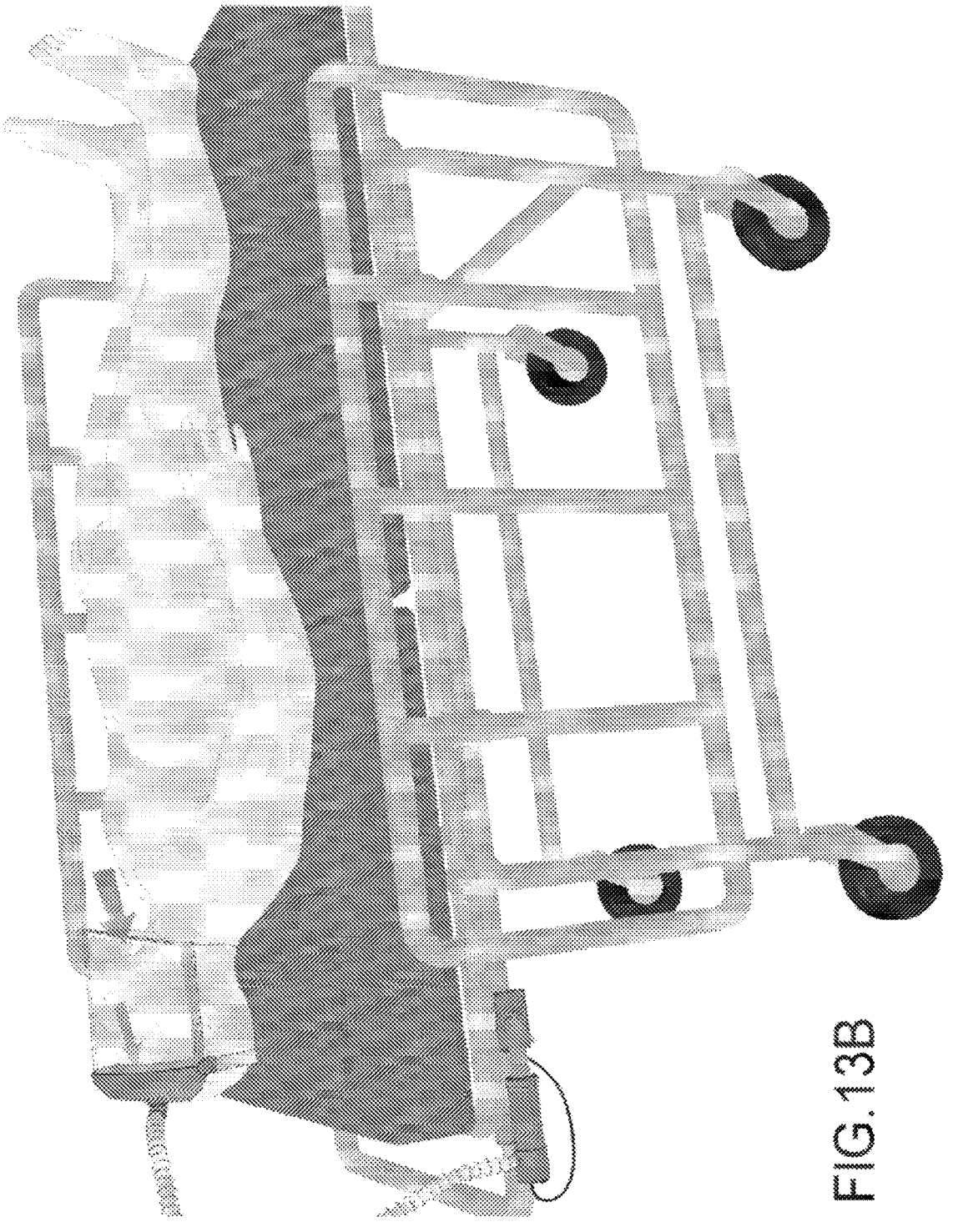
Figure 13C:
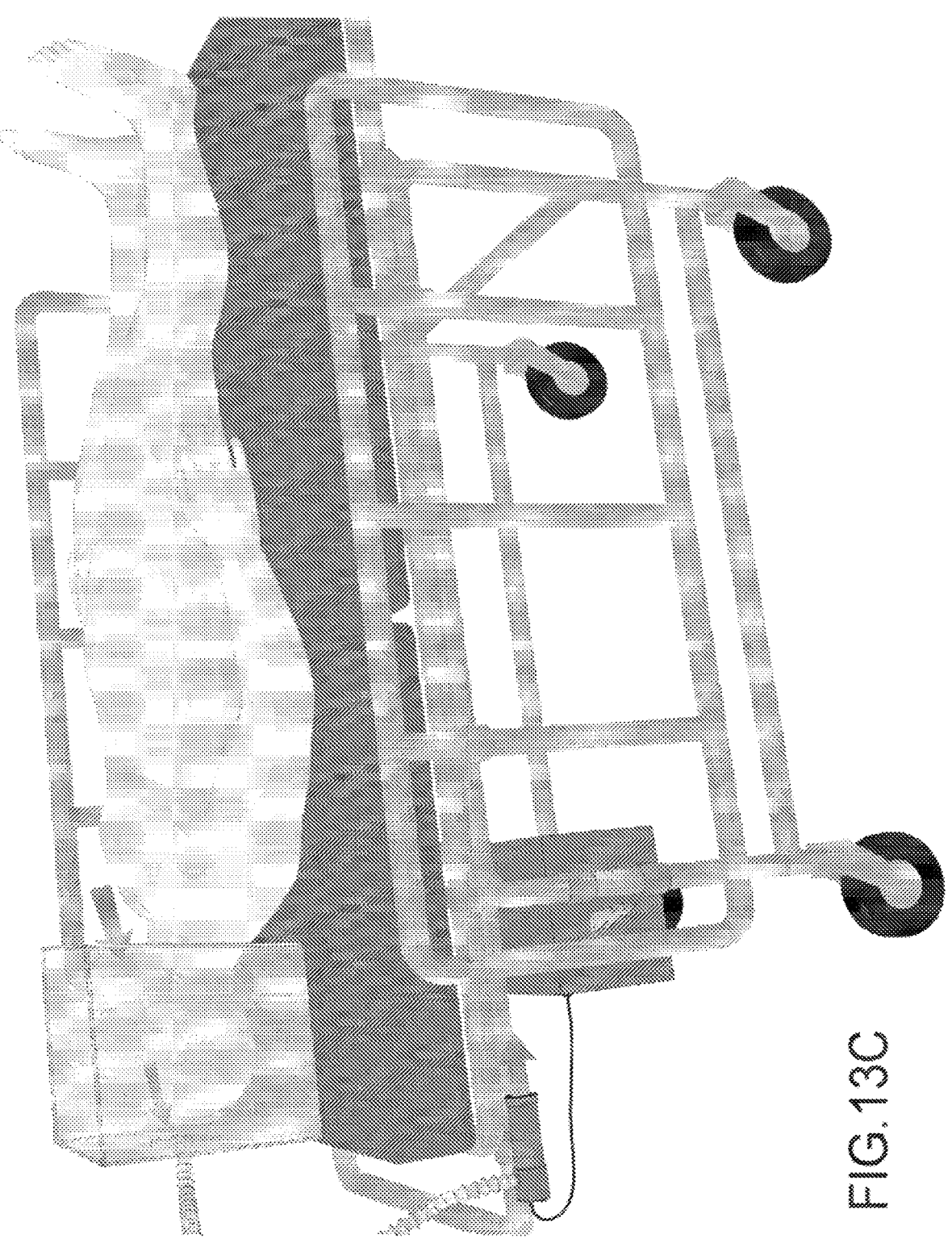
Figure 13D:
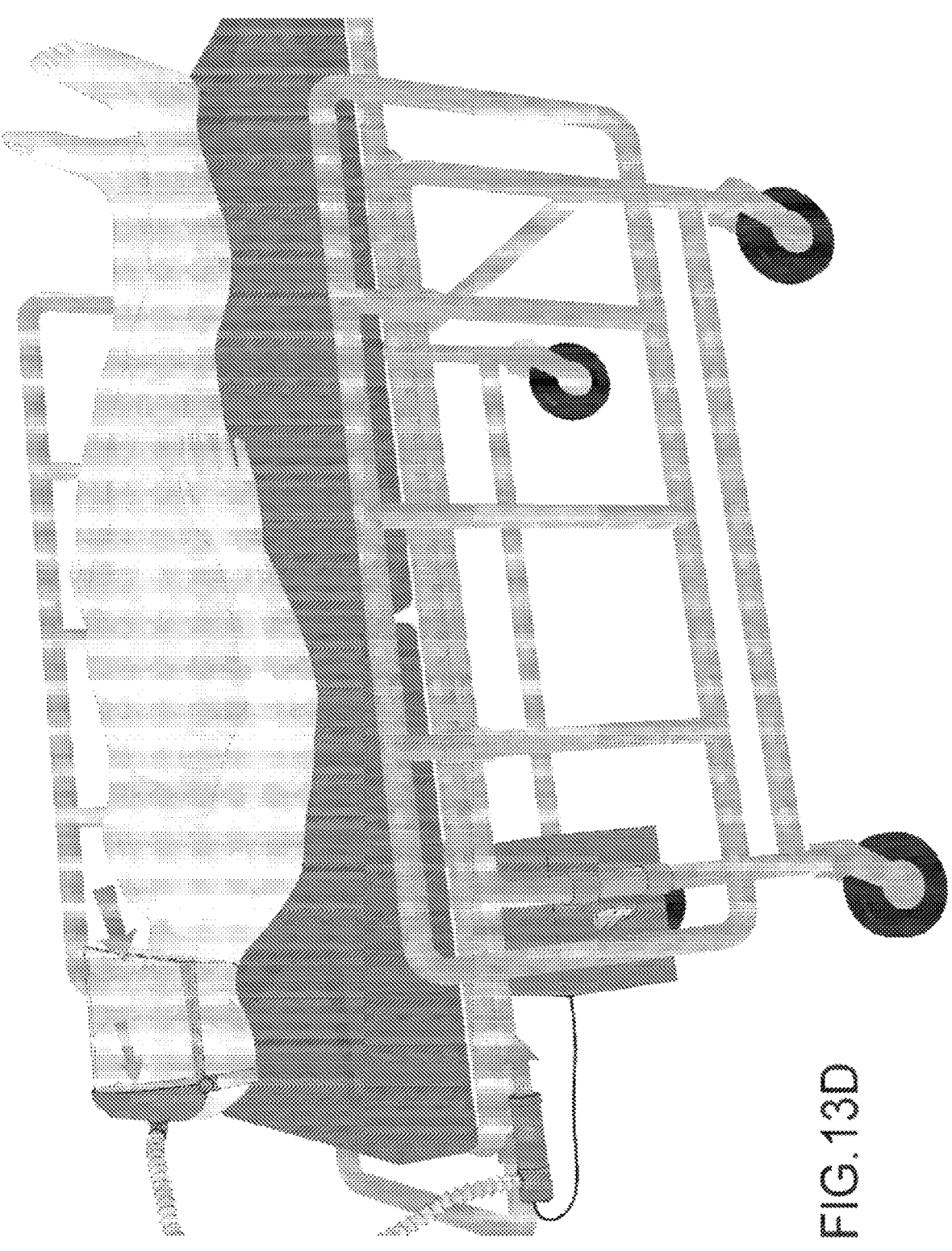
Figure 13E:
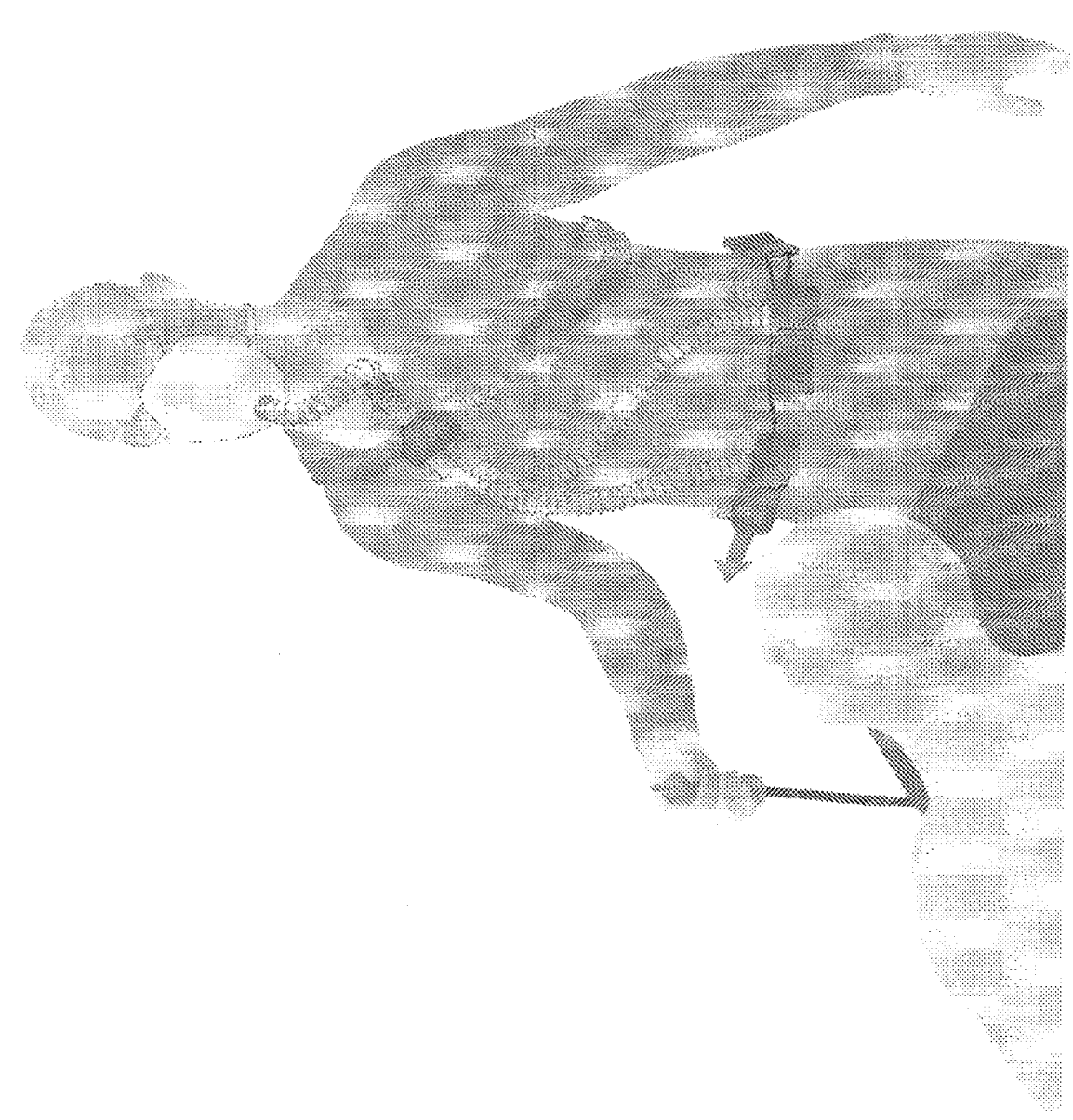
Figure 14A:
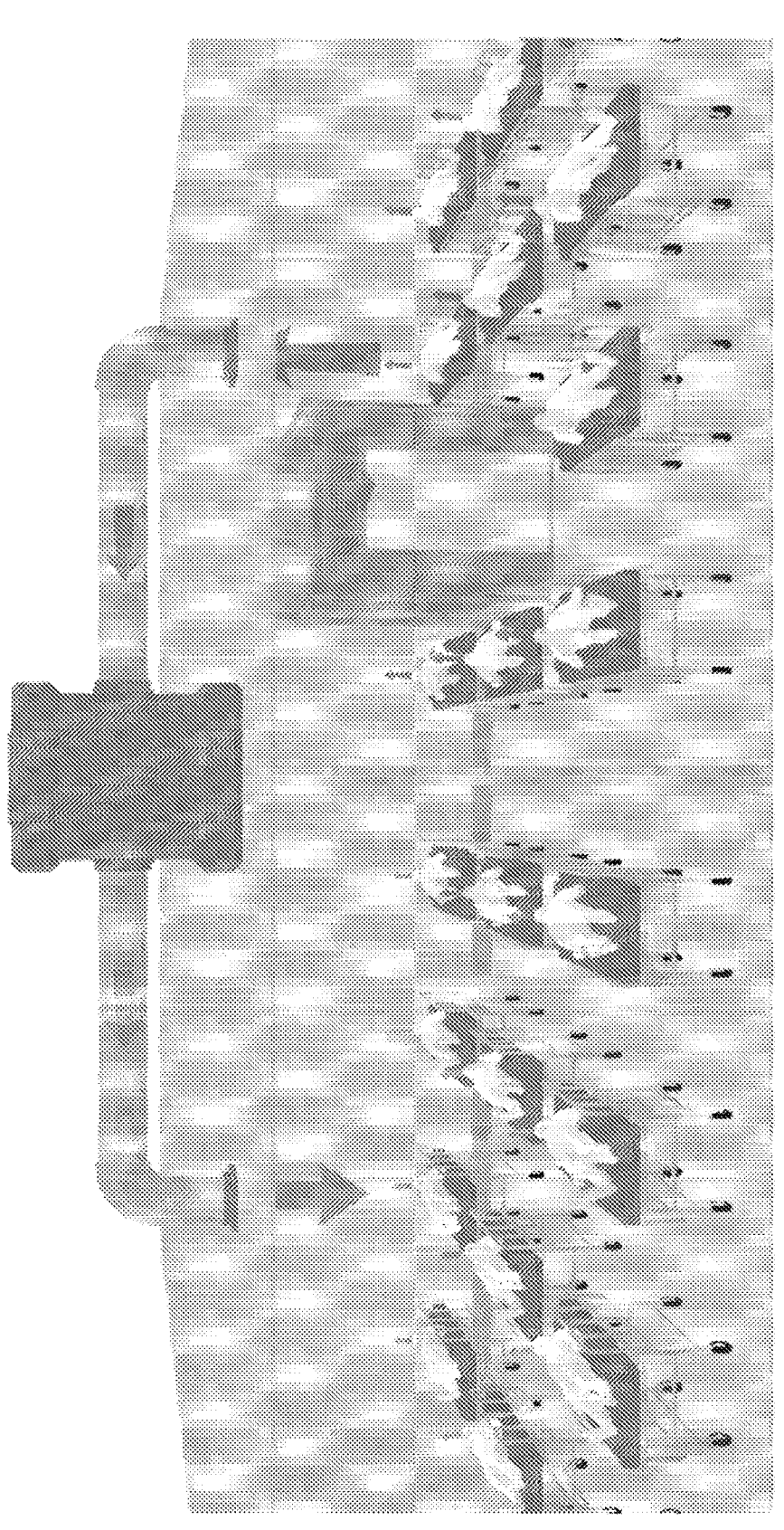
FIGS. 14A-14I show various filter systems for tented spaces in accordance with the present invention.
Figure 14B:
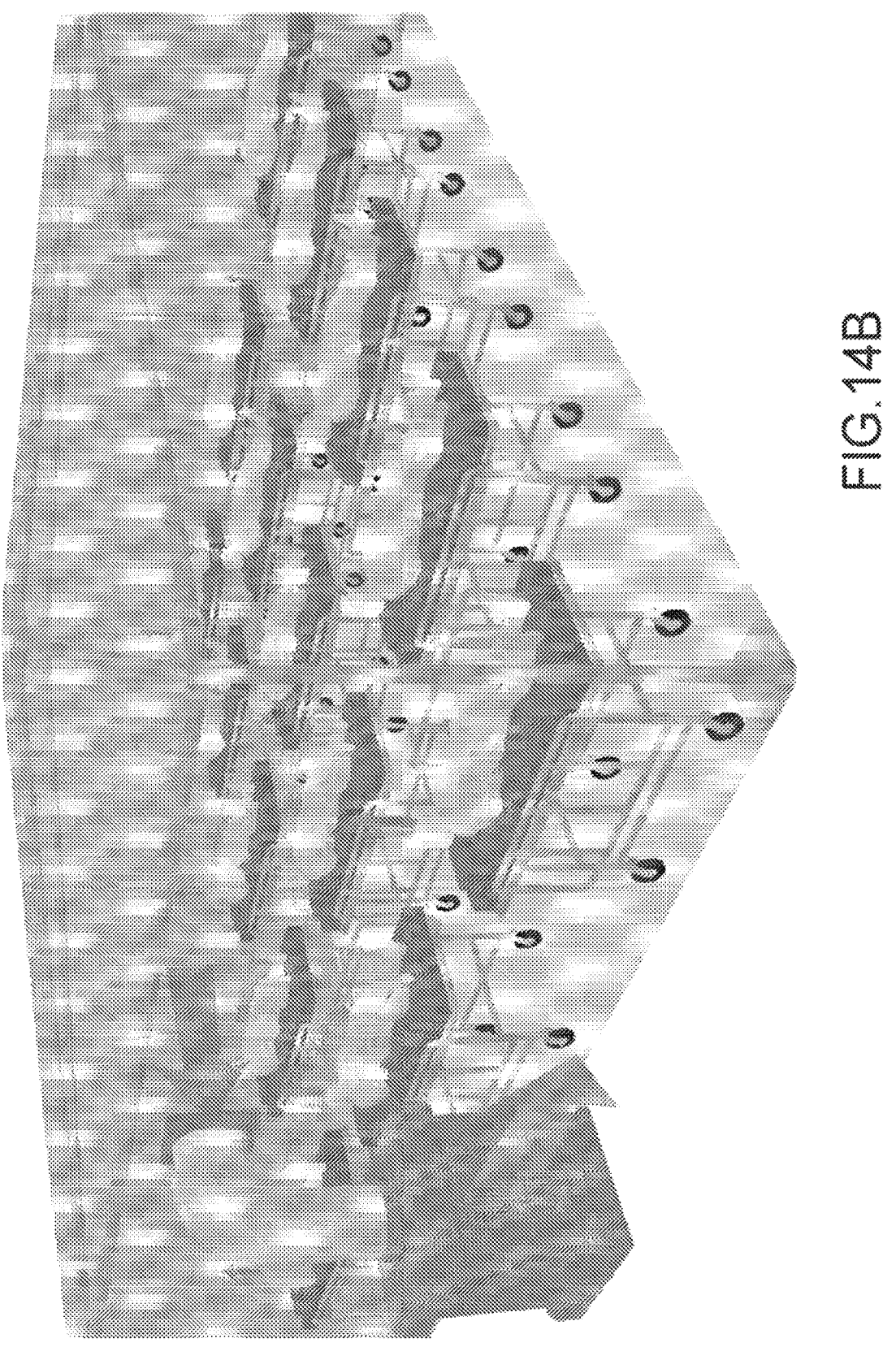
Figure 14C:
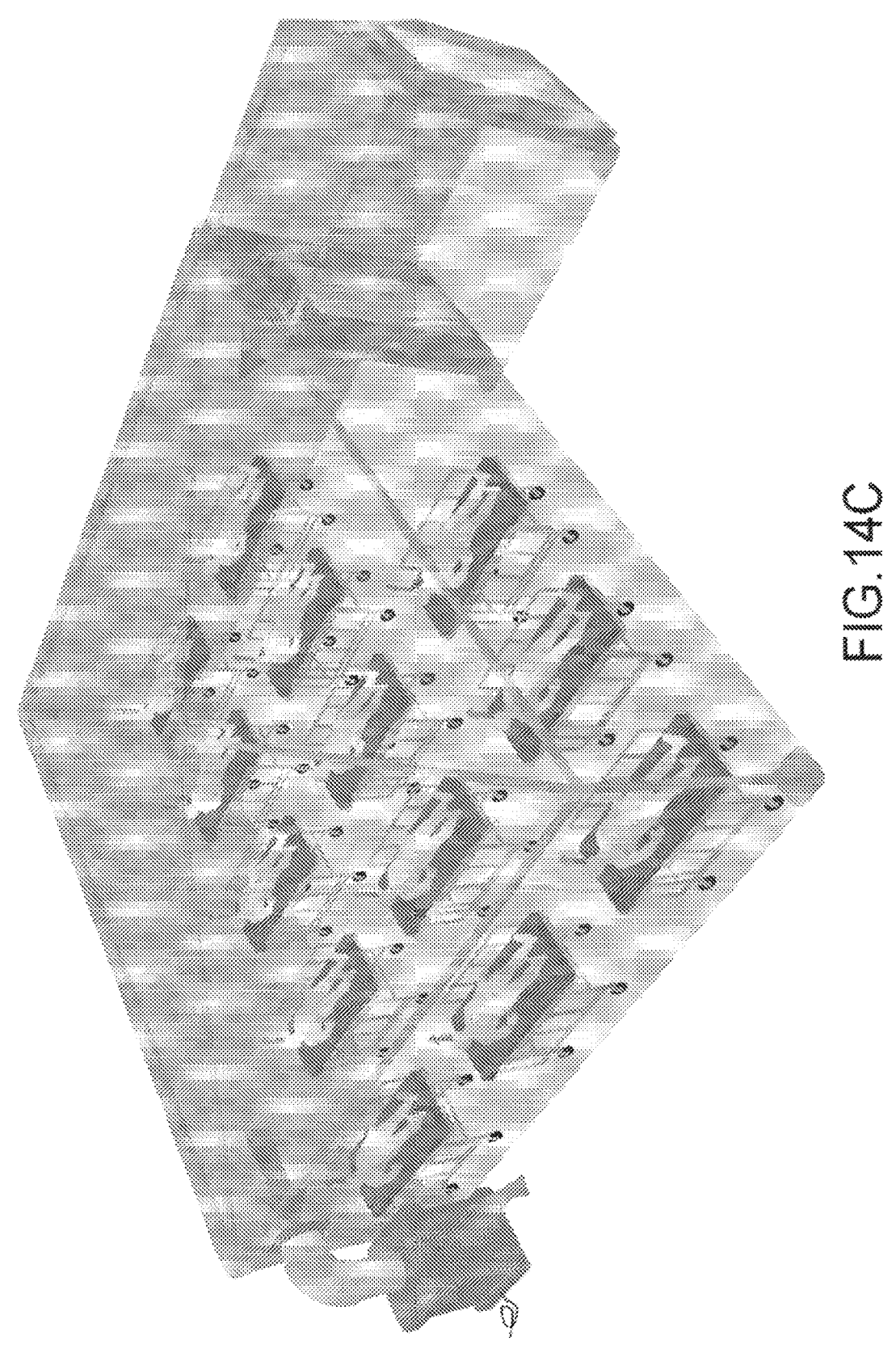
Figure 14D:
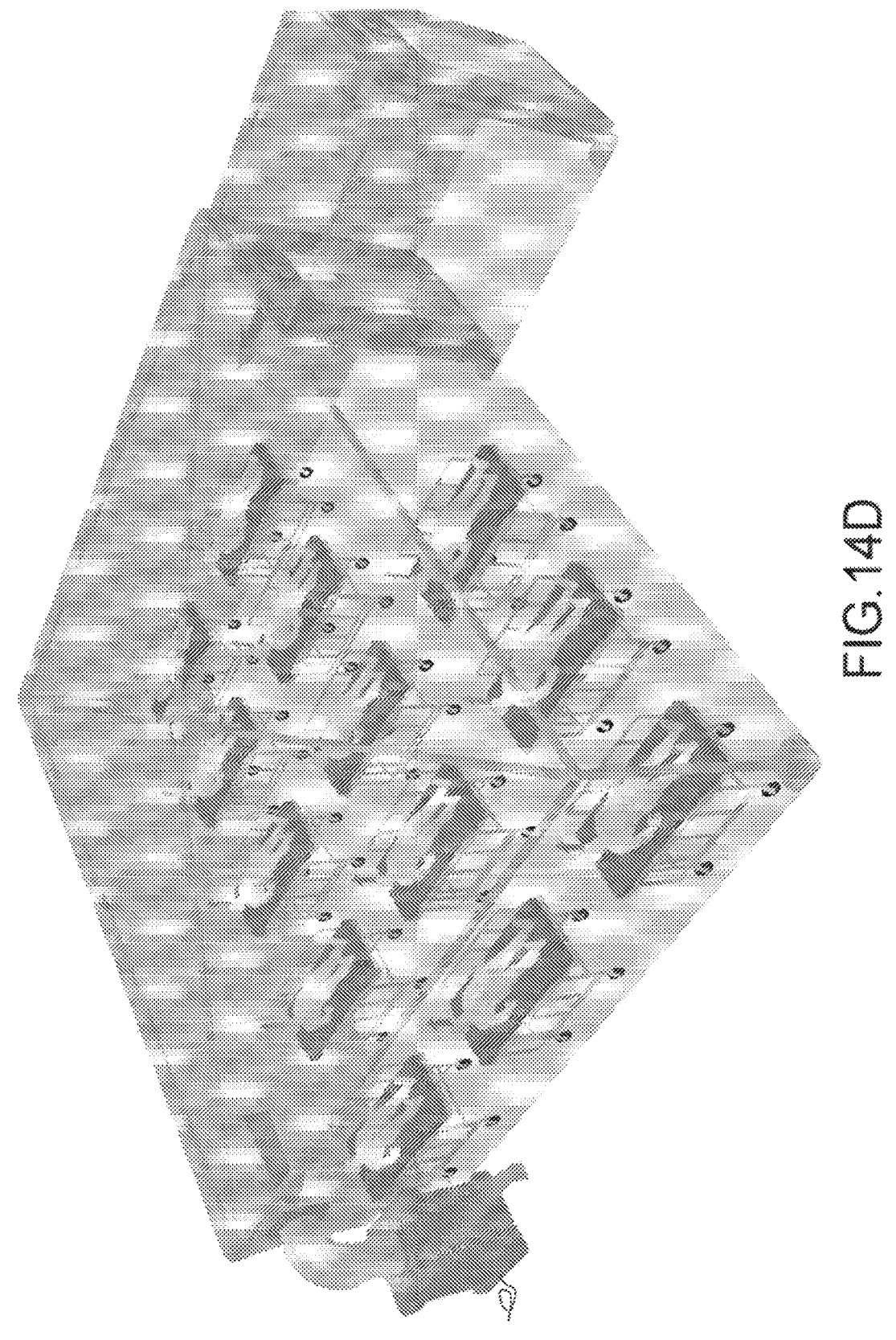
Figure 14E:
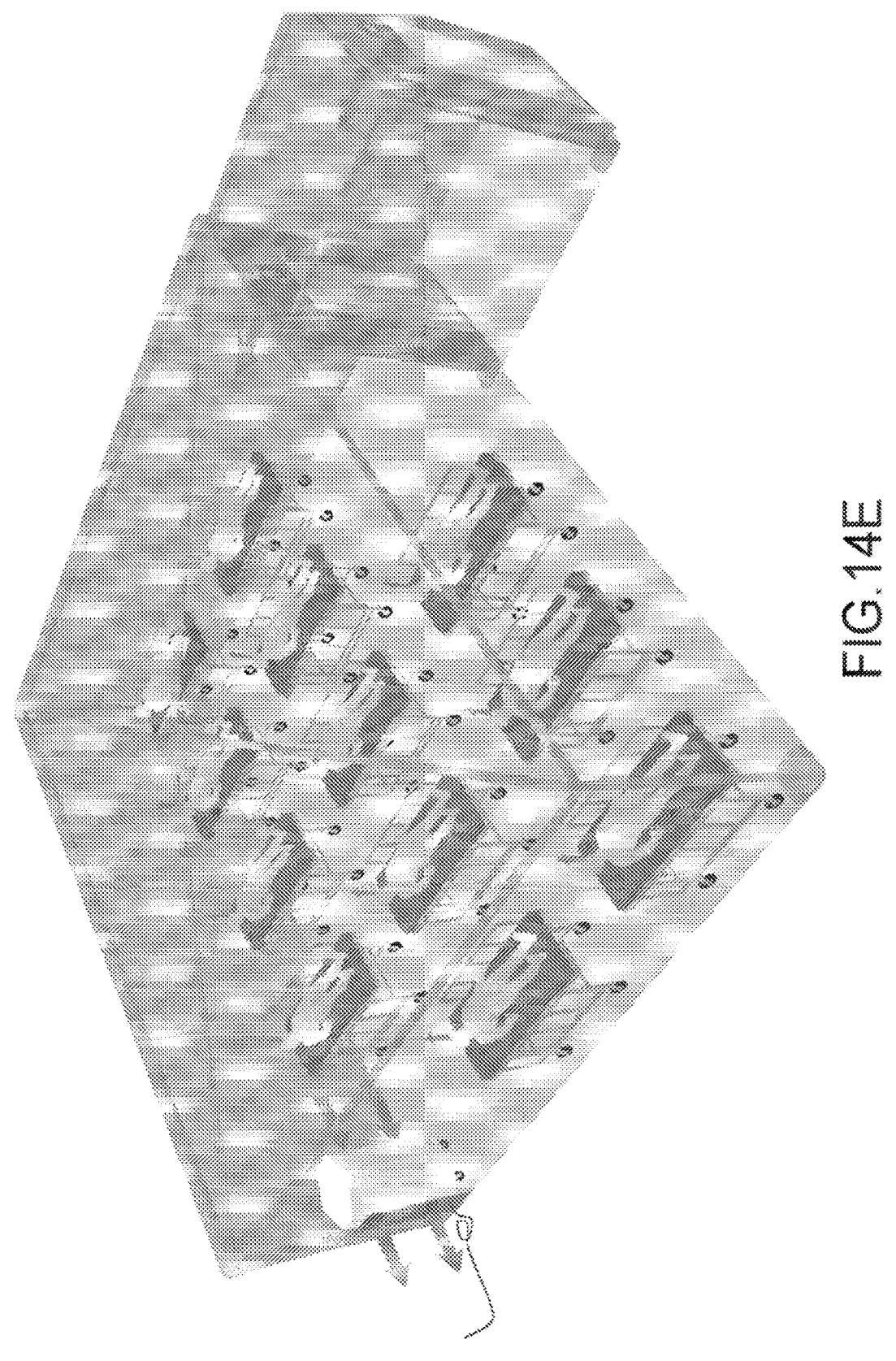
Figure 14F:
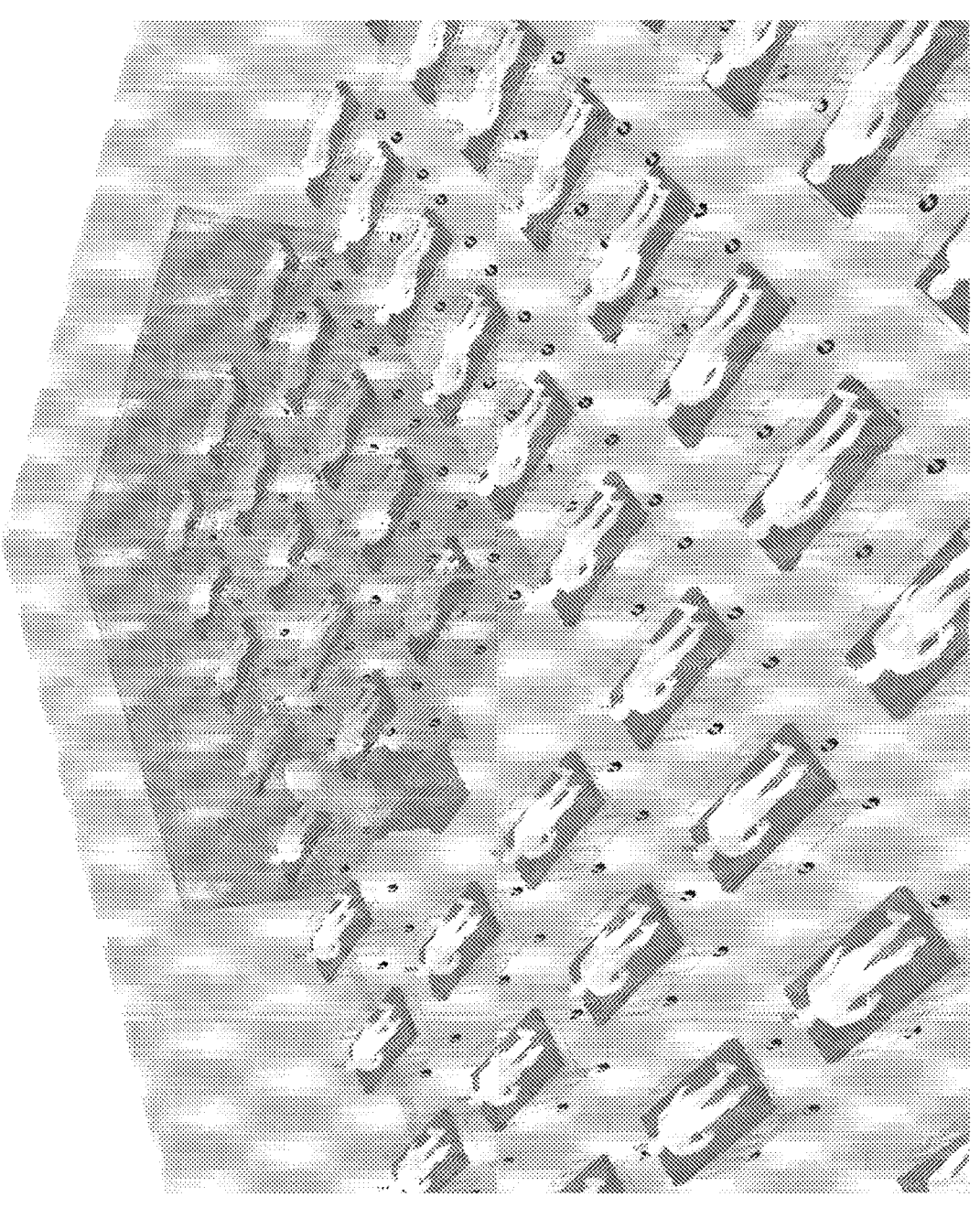
Figure 14G:
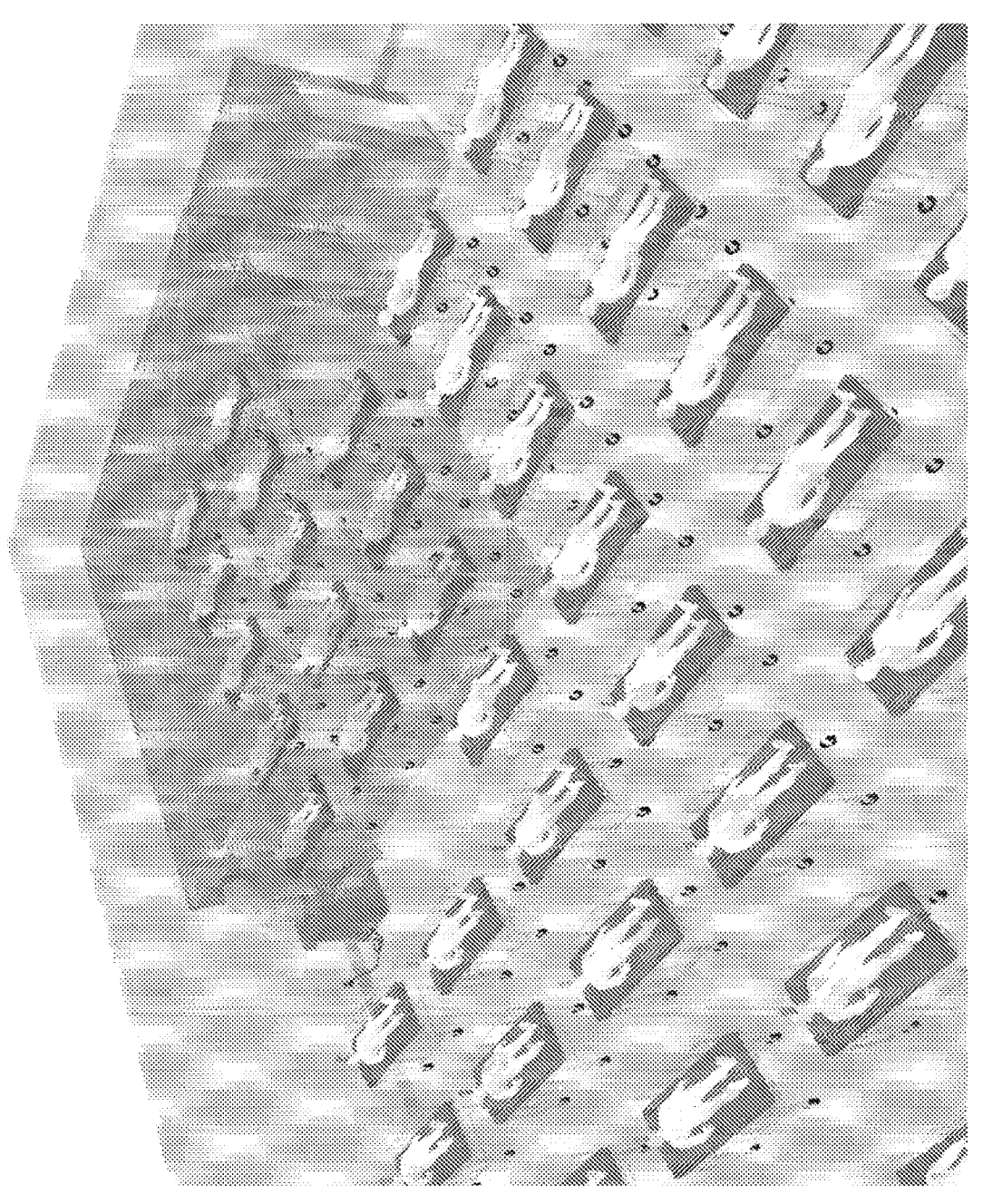
Figure 14H:
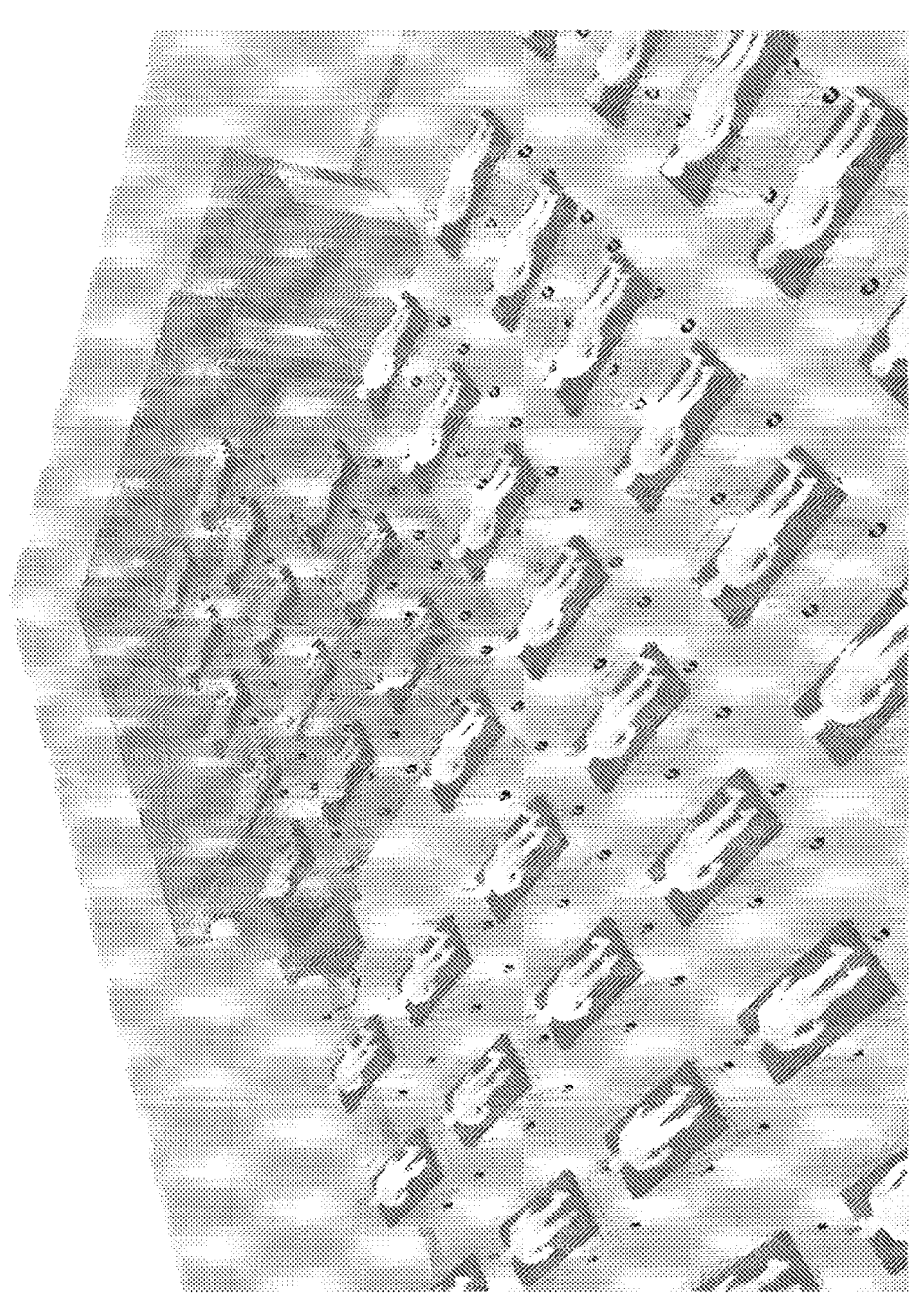
Figure 14I:
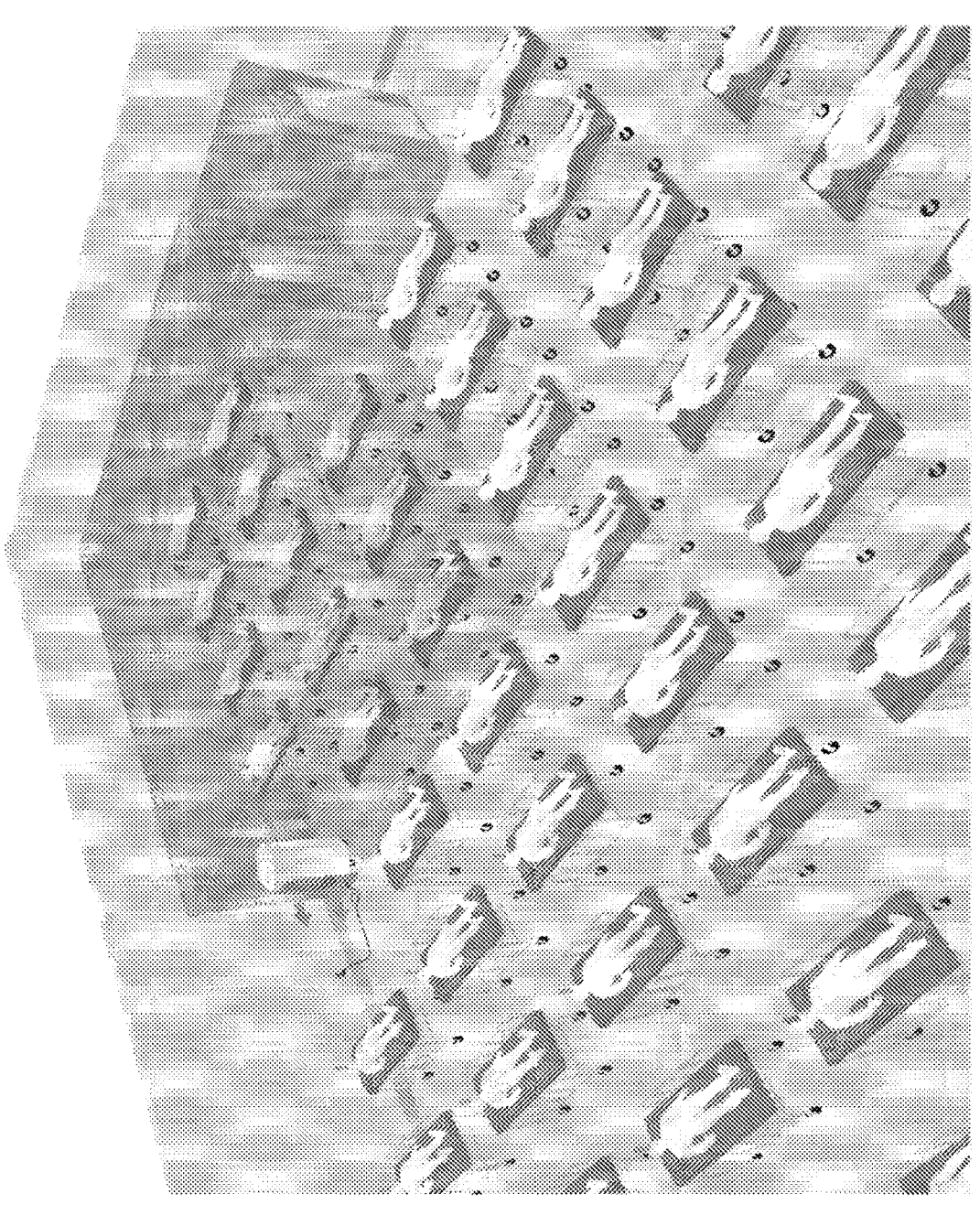

FIGS. 12-12G show an example instantiation of the system in accordance with the present invention in the form of a room air purifier/sterilizer. The apparatus can be used in an interior space (or an exterior space) with or without an isolation tent or chamber as described earlier. It can also be incorporated into an HVAC system. The apparatus consists of an enclosure with provisions for air intake and exhaust. The central volume contains a set of impeller fans with an optional heating element that move the air in the space into and through the enclosure. One possible example impeller fan is shown in FIG. 12F. The fans are arranged on a central shaft that rotates. The size, orientation and characteristics of each individual fan are selected to provide both maximum airflow efficiency and desired thermal heating of the air passing through the apparatus. The arrangement of the fans can be varied as to how many vanes, their geometries, the size, orientation and spacing of each fan relative to each other on the central shaft, the geometry, ducting and control dampers of the enclosure, etc. Control electronics can optionally be incorporated to report on airflow, air intake and exhaust temperature, damper position, motor status, speed and power as desired. The control electronics can drive a local display with a selector mechanism (buttons or touch) and if needed incorporate remote reporting via wired or wireless networking. The fans in some ways act as a centrifugal compressor, similar to the front fan assembly of a turbojet engine. The air can be heated by a combination of fan-driven turbulence and a degree of compression to a desired temperature that is sufficient to kill any pathogens. The optional heating element can be used to achieve sterilization upon startup or higher sterilization air temperatures, as can controlling the intake and exhaust airflow via control dampers, to insure no non-sterilized air is passed through. The advantage of the system is that inexpensive motors can be used to turn the central shaft at the required speeds. Note that if the motor is running the apparatus is functioning and delivering safe purified air. This is intrinsically simpler, easy for users to detect and more reliable than air purifiers that depend on filtration elements that can clog up or malfunction over time.

In FIG. 12A, the assembly 1200 is comprised of 5 main components. The spiral heat exchanger 1203 is essentially the same as described in earlier instantiations. The heating element 1202 is also similar as earlier instantiations. Additional components include a centrifugal fan turbine 1205, of which an arrangement of a plurality fan turbines revolve on an axle shaft 1201 on which the fan turbine(s) are affixed and rotate, the core air director 1206 which separates the incoming air from the spiral exchanger and directs it to the input of the fan turbine(s) 1205. The core air director also redirects the exhaust output of the fan turbine(s) to the exhaust path through the spiral heat exchanger.

FIG. 12B depicts an end on view of the exchanger assembly 1200. The location of the core air director 1206 in relationship to the outlet of the heating element 1202 and the inlet to the fan turbine 1205 is of significance. The path the air must follow is separated from the incoming air coming through the heating element 1202 and the exhaust air path back out through the spiral heat exchanger 1203 must be separated.

FIG. 12C shows and expanded version of the central section of the spiral exchanger. Air that is un-filtered is nearing the core of the spiral heat exchanger and is entering 1207 in a counter-clockwise direction. This could be clockwise if viewed from the opposite end. The air progresses through the final loop of the spiral heat exchanger picking up heat from exhausting air 1208 along this path. It enters the heating element 1202 to potentially add necessary heat to achieve the necessary temperature to kill any virus. This operation is similar to the instantiations described earlier. The air then enters the core air director 1206 and is directed through slots into the center of the fan turbine 1205. The fan turbine 1205 is spinning around the axle shaft 1201 in a counter-clockwise direction 1209 and the air is centrifugally compressed and accelerated simultaneously into the exhaust section of the core air director 1206 where it is directed to the exhaust path of the spiral heat exchanger. Air now is moving in a clockwise direction. It could be moving in a counter-clockwise direction if viewed from the opposite side. The air exhausts 1208 from the spiral heat exchanger after transferring the heat into the incoming air.

The importance of the efficiency of the spiral exchanger is significant. In theory, if the exchanger was 100 percent efficient, the exhaust temperature would be elevated an amount necessary to account for the heat input of the fan turbine. However, the efficiency is less than 100 percent.

Thus, some of the heat generated by the turbulence and compression of the air will not be exchanged. With careful balancing it is expected that the core temperature can be maintained without the use of the heating element 1202 while in operation. During startup, to prevent contaminated air from entering the exhaust path of the spiral heat exchanger, the core will be pre-heated to the desired temperature prior to starting the air motion. After the core temperature reaches the desired temperature, the fan can start.

FIG. 12D shows each of the components of the spiral heat exchanger assembly separated from one another. The main spiral heat exchanger 1203 is very similar to earlier instantiations. The axel shaft 1201 is shown with a plurality of fan turbines 1205. Four fan turbines 1205 are shown in this example, but more or less could be used to achieved the balance between heat input from the turbulence and compression, to the desire to hold a specific temperature. In addition, the flow rate of the air through the assembly can be regulated by the number of fans, their dimensions and the rotational rate. In this example, four fan turbines 1205 are shown for example of plurality. The core air director axial separator 1206 a is shown with four sets of inlet slots, and four sets of exhaust slots. This number of sets of slots correspond to the number of fan turbines of course. A larger, but shorter in circumference slot is shown for the inlet side of the fan turbine, and a narrow and longer in circumference slot is shown for the exhaust of the fan turbines. Since the back side of the fan turbine is a solid disc, each cell of the fan turbine subassembly is isolated from one another. The core air director radial separator 1206 b divides the incoming air to the inlet slots of the core air director axial separator 1206 a. It also directs the air exhausting from the core air director axial separator 1206 a out into the exhaust slot only of the spiral heat exchanger 1203. An electric motor 1211 that is variable speed is used to drive the fan turbine assembly.

FIG. 12E shows the components of the fan assembly integrated together. Each of the fan turbines 1205 can be seen showing in the exhaust slot of the air director axial separator 1206 a. The heating element can also be visualize more clearly in the inlet path through the core air director radial separator 1206 b, and into the inlet slots of the core air director axial separator. The electric motor 1211 can be on either or both ends of the axle shaft 1201. FIG. 12 G Shows the apparatus in an exploded view.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A personal protective equipment (PPE) system, comprising:
   a facemask assembly comprising:
   a head band to allow said facemask assembly to attach to a user's head, wherein said head band surrounds at least a portion of the front of the head and at least a portion of the back of the head, without entirely encompassing the top of the head; and
   a shield, formed from transparent, air impermeable material, configured to extend over a portion of a face of the user including eyes, a nose, and a mouth of the user to define a breathing space over the eyes, nose and mouth of the user within an interior of said facemask assembly and operable to allow input air to flow over eyes, nose and mouth of the user, down the inside of the shield, and out the bottom of the shield; wherein the shield is curved to expose side portions of the user's head;
   a gaiter for extending between one or more ends of said shield and a body of a user, wherein at least one of said shield and said gaiter extend over the nose and mouth of said user to define a breathing space within said interior of said facemask assembly; and
   a positive pressure air supply assembly, including:
   an air inlet;
   a conduit assembly extending between said air inlet and said facemask assembly; and
   at least one air accelerator for forcing air through said conduit assembly from said air inlet to said facemask assembly.

2. The system as set forth in claim 1, wherein said shield is mounted on headgear.

3. The system as set forth in claim 2, wherein said headgear comprises said headband.

4. The system as set forth in claim 2, wherein said headgear comprises a cap.

5. The system as set forth in claim 2, wherein said shield is movable from a first position, wherein said shield extends over said eyes of said user, and a second position wherein said shield is outside of a line of sight of said user.

6. The system as set forth in claim 2, wherein said shield is formed from polycarbonate material.

7. The system is set forth in claim 1, wherein said gaiter is removably attachable to said facemask assembly.

8. The system as set forth in claim 1, wherein said positive pressure air supply assembly is mounted on headgear.

9. The system as set forth in claim 1, wherein said positive pressure air supply assembly is mounted on a body pack and interconnected to said facemask assembly by tubing.

10. The system as set forth in claim 1, wherein said positive pressure air supply assembly comprises at least one filter for removing contaminants from air.

11. The system as set forth in claim 10, wherein said at least one filter comprises an electrostatic filter.

12. The system as set forth in claim 11, wherein said electrostatic filter comprises an electrostatic element formed as a spiral of conductive material.

13. The system as set forth in claim 11, wherein said electrostatic filter further comprises a filter medium.

14. The system as set forth in claim 10, wherein said at least one filter comprises a plurality of filters disposed in series relative to an air flow path.

15. The system as set forth in claim 10, wherein said at least one filter comprises a plurality of filters disposed in parallel to filter separate air flow paths.

16. The system as set forth in claim 15, further comprising a selector device, movable between different positions, that is operative for selecting to use one or more of said plurality of filters.

17. The system as set forth in claim 1, further comprising a port for receiving power from an external source.

18. The system as set forth in claim 1, further comprising mounting structure for receiving a portable power source.

19. The system as set forth in claim 1, further comprising a portable power source.

20. The system as set forth in claim 19, wherein said portable power source is mounted in headgear.

21. The system as set forth in claim 19, wherein said portable power source is mounted in a body pack.

22. The system as set forth in claim 19, wherein said portable power source comprises a rechargeable battery.

23. The system as set forth in claim 19, wherein said portable power source comprises a rechargeable battery pack and a port for recharging said rechargeable battery pack.

24. The system as set forth in claim 1, wherein said at least one air accelerator provides a volumetric airflow sufficient to maintain positive pressure at said facemask assembly throughout a breathing cycle of said user.

25. The system is set forth in claim 1, wherein said at least one air accelerator provides a volumetric airflow rate of at least about 30 L per minute.

26. The system as set forth in claim 1, wherein said at least one air accelerator provides a volumetric airflow rate of at least about 60 L per minute.

27. The system as set forth in claim 1, wherein said at least one air accelerator comprises a fan having a diameter of no more than about 3 inches.

28. The system as set forth in claim 1, wherein said at least one air accelerator comprises a fan having a diameter of no more than about 2 inches.

29. A facemask system, comprising:

a facemask assembly comprising:

a head band to allow said facemask assembly to attach to a user's head, wherein said head band surrounds at least a portion of the front and at least a portion of the back of the head, without entirely encompassing the top of the head;

a shield, formed from transparent, air impermeable material, configured to extend over a portion of a face of the user including eyes, a nose, and mouth of said the user to define a breathing space over the eyes, nose and mouth of the user within an interior of the shield and operable to allow input air to flow over eyes, nose and mouth of the user, down the inside of the shield, and out the bottom of the shield; wherein the shield is curved to expose side portions of the user's head; and a gaiter for extending between one or more ends of said shield and a body of the user, wherein at least one of said shield and said gaiter extend over a nose and a mouth of said user to define a breathing space within an interior of said facemask assembly.

30. An apparatus for use in a personal protective equipment (PPE) system, said system including an assembly comprising a head band to allow said assembly to attach to a user's head, wherein said head band surrounds at least a portion of the front of the head and at least a portion of the back of the head, without entirely encompassing the top of the head, and a shield, formed from transparent, air impermeable material, configured to extend over a portion of a face of the user including the user's eyes, a nose, and a mouth of the user to define a breathing space over the eyes, nose and mouth of the user within an interior of the shield, wherein the shield is curved to expose side portions of the user's head and operable to allow input air to flow over eyes, nose and mouth of the user, down the inside of the shield, and out the bottom of the shield, said apparatus comprising:

a gaiter for extending between one or more ends of said shield and a body of the user, wherein at least one of said shield and said gaiter extend over a nose and a mouth of said user to define a breathing space; and a connector for removably attaching said gaiter to said shield.

31. A personal protective (PPE) system, comprising:

a facemask assembly, comprising:

a head band to allow said facemask assembly to attach to a user's head, wherein said head band surrounds at least a portion of the front of the head and at least a portion of the back of the head, without entirely encompassing the top of the head; and a shield, formed from transparent, air impermeable material, configured to extend over a portion of a face of the user including the user's eyes, a nose, and a mouth of the user to define a breathing space over the eyes, nose, and mouth of the user within an interior of the facemask assembly and operable to allow input air to flow over eyes, nose and mouth of the user, down the inside of the shield, and out the bottom of the shield; wherein the shield is curved to expose side portions of the user's head;

an air inlet for providing air to an interior of said facemask assembly; and a gaiter for extending between one or more ends of said shield and a body of a user, wherein at least one of said shield and said gaiter extend over the nose and mouth of said user to define a breathing space within said interior of said facemask assembly; and a filtered air supply assembly, including:

a filter for removing contaminants from air;

a conduit assembly, extending between said filter and said air inlet of said facemask assembly; and a fan for forcing air through said conduit assembly from said filter of said filtered air supply assembly to said air inlet of said facemask assembly.

* * * * *